United States Patent
Numata et al.

(10) Patent No.: US 11,925,106 B2
(45) Date of Patent: Mar. 5, 2024

(54) CONDENSED CYCLIC COMPOUND, COMPOSITION INCLUDING THE SAME, AND ORGANIC LIGHT-EMITTING DEVICE INCLUDING THE CONDENSED CYCLIC COMPOUND

(71) Applicant: Samsung Electronics Co., Ltd., Suwon-si (KR)

(72) Inventors: Masaki Numata, Kanagawa (JP); Mitsunori Ito, Kanagawa (JP)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 466 days.

(21) Appl. No.: 16/726,410

(22) Filed: Dec. 24, 2019

(65) Prior Publication Data
US 2020/0212307 A1    Jul. 2, 2020

(30) Foreign Application Priority Data

Dec. 28, 2018    (JP) .................................. 2018-248446
Oct. 30, 2019    (KR) ........................ 10-2019-0136946

(51) Int. Cl.
*C07C 13/567*    (2006.01)
*C09K 11/02*    (2006.01)
(Continued)

(52) U.S. Cl.
CPC ......... H10K 85/615 (2023.02); *C07C 13/567* (2013.01); *C09K 11/025* (2013.01);
(Continued)

(58) Field of Classification Search
None
See application file for complete search history.

(56) References Cited

U.S. PATENT DOCUMENTS 7,883,785 B2    2/2011    Stoessel et al.
7,883,786 B2    2/2011    Abe et al.
(Continued)

FOREIGN PATENT DOCUMENTS

CN    102372665 A   *  3/2012   ........... C07D 213/06
CN    106893581 A   *  6/2017   ........... C07D 209/90
(Continued)

OTHER PUBLICATIONS

Machine translation of CN-102372665, translation generated Jul. 2022, 22 pages. (Year: 2022).*
(Continued)

*Primary Examiner* — Robert S Loewe
(74) *Attorney, Agent, or Firm* — CANTOR COLBURN LLP

(57) ABSTRACT

A condensed cyclic compound represented by Formula 1, a composition including the same, and an organic light-emitting device including the condensed cyclic compound:

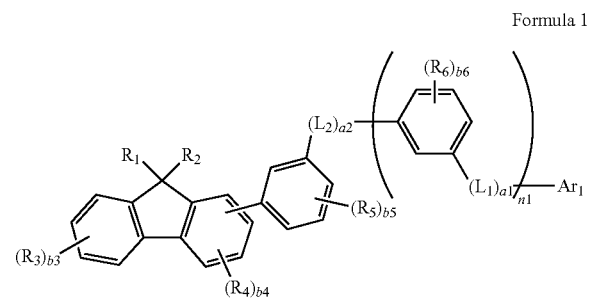

Formula 1 wherein $R_1$-$R_6$, $L_1$-$L_2$, $Ar_1$, n1, a1-a2, and b3-b6 are described in the specification.

19 Claims, 5 Drawing Sheets

(51) Int. Cl.
*H10K 85/60* (2023.01)
*H10K 50/11* (2023.01)
*H10K 71/00* (2023.01)
*H10K 71/12* (2023.01)
*H10K 101/10* (2023.01)
*H10K 101/30* (2023.01)
*H10K 101/40* (2023.01)

(52) U.S. Cl.
CPC .......... *C07C 2603/18* (2017.05); *H10K 50/11* (2023.02); *H10K 71/00* (2023.02); *H10K 71/12* (2023.02); *H10K 2101/10* (2023.02); *H10K 2101/30* (2023.02); *H10K 2101/40* (2023.02)

(56) References Cited

U.S. PATENT DOCUMENTS

| | | | |
|---|---|---|---|
| 8,013,160 | B2 | 9/2011 | Mitsunori et al. |
| 8,158,835 | B2 | 4/2012 | Kamatani et al. |
| 9,680,111 | B2 | 6/2017 | Feldman et al. |
| 2007/0122652 | A1* | 5/2007 | Hashimoto ......... H01L 51/0043 585/27 |
| 2009/0273278 | A1 | 11/2009 | Lee et al. |
| 2014/0117327 | A1* | 5/2014 | Lim .................... C07D 209/86 585/27 |
| 2015/0249221 | A1 | 9/2015 | Zeng et al. |
| 2016/0093808 | A1 | 3/2016 | Adamovich et al. |
| 2016/0141506 | A1 | 5/2016 | Miyashita et al. |
| 2017/0170401 | A1 | 6/2017 | Kim et al. |
| 2017/0179396 | A1* | 6/2017 | Kim ................... H01L 51/0072 |
| 2018/0094000 | A1 | 4/2018 | Hatakeyama et al. |
| 2018/0138420 | A1 | 5/2018 | Tada et al. |
| 2018/0145260 | A1 | 5/2018 | Joosten et al. |
| 2019/0207120 | A1* | 7/2019 | Han ..................... H01L 51/50 |

FOREIGN PATENT DOCUMENTS

| | | | | |
|---|---|---|---|---|
| CN | 107141191 | A | * 9/2017 | ............ C07C 13/72 |
| JP | 2005536565 | A | 12/2005 | |
| JP | 2008255074 | A | 10/2008 | |
| JP | 2008308449 | A | 12/2008 | |
| JP | 2009292807 | A | 12/2009 | |
| JP | 2014509067 | A | 4/2014 | |
| JP | 2016094373 | A | 5/2016 | |
| JP | 2020537647 | A | 12/2020 | |
| KR | 20160050614 | A | 5/2016 | |
| KR | 20160064027 | A | * 6/2017 | ............ C07F 9/6581 |
| KR | 102008896 | B1 | * 8/2019 | ............ C07D 487/14 |
| WO | 2005123634 | A1 | 12/2005 | |
| WO | 2012033061 | A1 | 3/2012 | |
| WO | 2012087955 | A1 | 6/2012 | |
| WO | 2016194604 | A1 | 8/2016 | |
| WO | 2016152418 | A1 | 9/2016 | |
| WO | 2016184540 | A1 | 11/2016 | |
| WO | 2017111389 | A1 | 6/2017 | |
| WO | 2019072928 | A1 | 4/2019 | |
| WO | WO-2019085684 | A1 | * 5/2019 | ............ C07C 253/30 |

OTHER PUBLICATIONS

Machine translation of Chen et al. (CN-107141191), translation generated Oct. 2022, 24 pages. (Year: 2022).*
Machine translation of Chen et al. (WO-2019085684), translation generated Oct. 2022, 20 pages. (Year: 2022).*
Machine translation of KR-20160064027-A, translation generated Jun. 2023, 21 pages. (Year: 2023).*
English Translation of Office Action dated Jan. 24, 2023 issued in corresponding Japanese patent application No. 2018-248446, 8 pgs.
Office Action dated Jan. 24, 2023 issued in corresponding Japanese patent application No. 2018-248446, 8 pgs.

* cited by examiner

FIG. 3
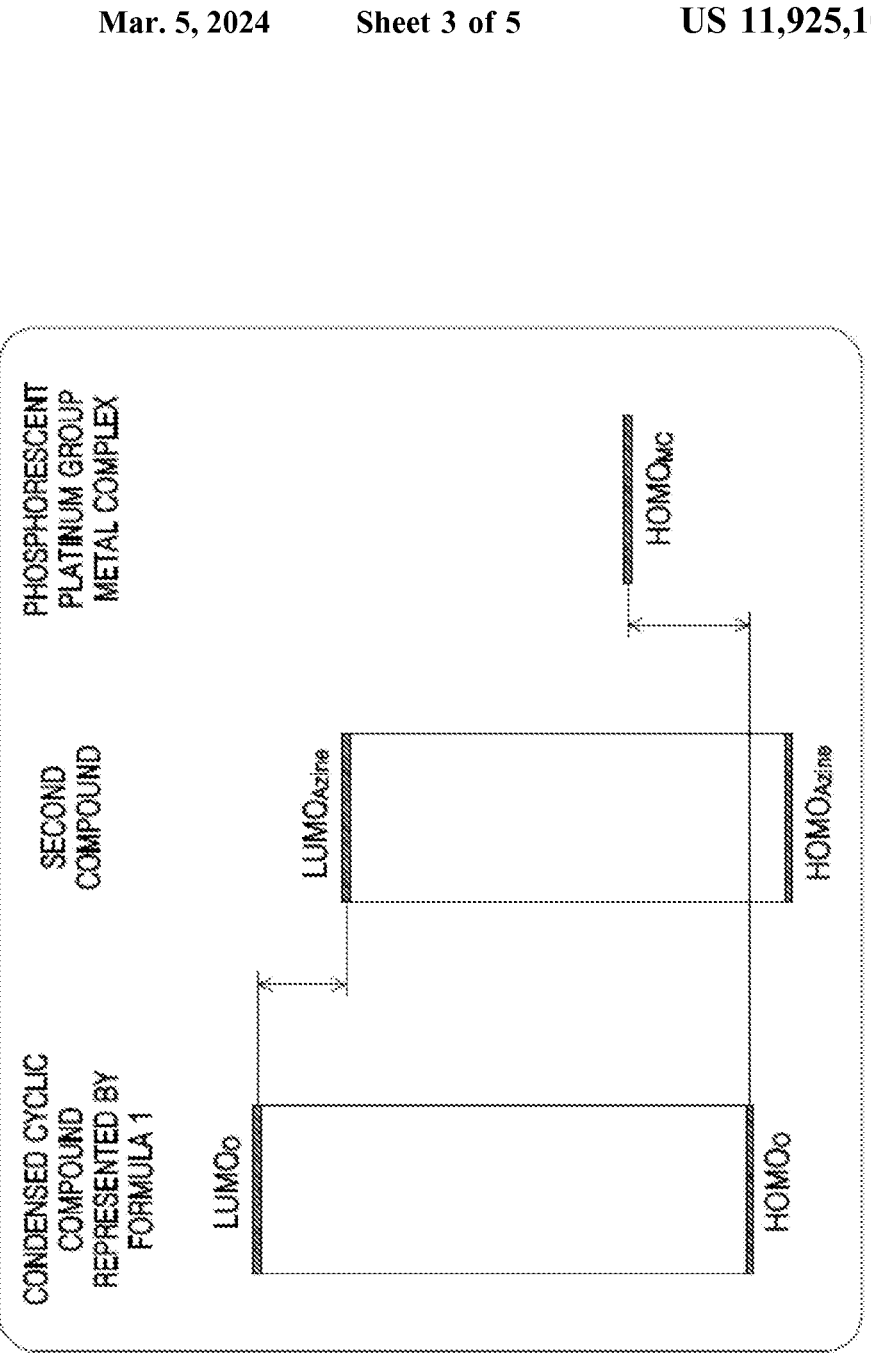
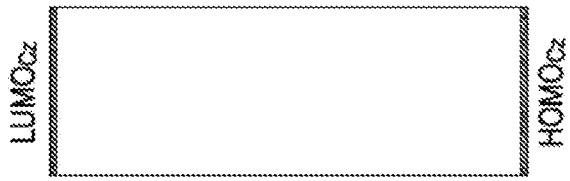

CONDENSED CYCLIC COMPOUND, COMPOSITION INCLUDING THE SAME, AND ORGANIC LIGHT-EMITTING DEVICE INCLUDING THE CONDENSED CYCLIC COMPOUND

CROSS-REFERENCE TO RELATED APPLICATIONS

This application claims priority to and the benefits of Korean Patent Application No. 10-2019-0136946, filed on Oct. 30, 2019, in the Korean Intellectual Property Office, and Japanese Patent Application No. 2018-248446, filed on Dec. 28, 2018, in the Japanese Patent Office, and all the benefits accruing thereform under 35 U.S.C. § 119, the contents of which are incorporated herein in their entirety by reference.

BACKGROUND

1. Field

One or more embodiments relate to a condensed cyclic compound, a material for an organic light-emitting device including the condensed cyclic compound, and an organic light-emitting device including the material.

2. Description of Related Art

Organic light-emitting devices are self-emission devices that produce full-color images, and also have wide viewing angles, high contrast ratios, short response times, as well as excellent characteristics in terms of brightness, driving voltage, and response speed.

In an example, an organic light-emitting device includes an anode, a cathode, and an organic layer that is disposed between the anode and the cathode and includes an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. The holes and the electrons, which are carriers, recombine in the emission layer to produce excitons. These excitons transition from an excited state to a ground state, thereby generating light.

SUMMARY

One or more embodiments include a condensed cyclic compound, a composition including the same, and an organic light-emitting device using the condensed cyclic compound.

In manufacturing an organic light-emitting device, it is common to form an organic film constituting the organic light-emitting device by a dry film-forming method such as a vapor deposition method. However, when a film is formed by a dry film-forming method, such as a vapor deposition method, relatively long time and high costs are needed. Therefore, instead of such a dry film-forming method, wet film-forming methods, such as a solution coating method (henceforth a coating method), which may reduce the amount of time and the costs, are considered for use in the manufacturing process.

However, when wet film-forming methods are applied to conventional compounds, due to the low solubility of the compounds, the pot life (lifespan in solution) of the solution is short. After the film formation, aggregation of organic molecules may occur in an emission layer. Therefore, an organic light-emitting device formed by the coating method may not have sufficient current efficiency and light-emission lifespan.

Organic light-emitting devices using such compounds have low efficiency and short lifespans.

Accordingly, the present disclosure aims at providing of a compound having high solubility and providing a long solution pot life and an organic light emitting device having high efficiency and a long lifespan.

In detail, an organic light-emitting device including the condensed cyclic compound may have high luminescent efficiency and a long lifespan. In addition, the condensed cyclic compound may have a low glass transition temperature and thus have high solubility, thereby increasing the pot life of the solution including the compound, and thus may be suitable for use in a solution coating method.

Additional aspects will be set forth in part in the description which follows and, in part, will be apparent from the description, or may be learned by practice of the presented embodiments of the disclosure.

According to one aspect, there is provided a condensed cyclic compound represented by Formula 1:

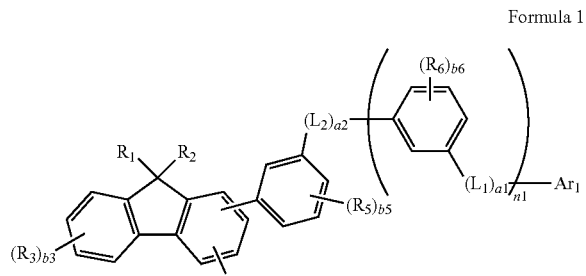

Formula 1

Formula 2

$$*{-}(L_{11})_{a11}{-}Ar_{11},$$

wherein, in Formula 1 and Formula 2, $L_1$, $L_2$, and $L_{11}$ may each independently be a single bond, a substituted or unsubstituted $C_5$-$C_{60}$ carbocyclic group, or a substituted or unsubstituted $C_1$-$C_{60}$ heterocyclic group, a1, a2 and a11 may each independently be an integer from 1 to 5, $Ar_1$ and $Ar_{11}$ may each independently be a substituted or unsubstituted $C_5$-$C_{60}$ carbocyclic group, $R_1$ to $R_6$ may each independently be a group represented by Formula 2, hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_7$-$C_{60}$ arylalkyl group, a substituted or unsubstituted $C_7$-$C_{60}$ arylalkyloxy group, a substituted or unsubstituted $C_7$-$C_{60}$ arylalkylthio group, a substituted or unsubstituted $C_8$-$C_{60}$ arylalkenyl group, a substituted or unsubstituted $C_8$-$C_{60}$ arylalkynyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkyl heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), or —N($Q_1$)($Q_2$), b3, b5, and b6 may each independently be an integer from 0 to 4, b2 may be an integer from 0 to 3, two adjacent groups of $R_1$, $R_2$, $R_3$(s) in the number of b3, $R_4$(s) in the number of b4, $R_5$(s) in the number of b5, and $R_6$(s) in the number of b6 may be optionally linked to form a substituted or unsubstituted $C_5$-$C_{30}$ carbocyclic group or a substituted or unsubstituted $C_1$-$C_{30}$ heterocyclic group, n1 may be an integer from 1 to 5, when a1 and a2 are each 1, $L_1$ and $L_2$ are each a single bond, and n1 is 1, $Ar_1$ is not a fluorene group, at least one substituent of the substituted $C_5$-$C_{60}$ carbocyclic group, the substituted $C_1$-$C_{60}$ heterocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_7$-$C_{60}$ alkylaryl group, the substituted $C_7$-$C_{60}$ arylalkyl group, the substituted $C_7$-$C_{60}$ arylalkyloxy group, the substituted $C_7$-$C_{60}$ arylalkylthio group, the $C_8$-$C_{60}$ arylalkenyl group, the $C_8$-$C_{60}$ arylalkynyl group, the substituted $C_6$-$C_{60}$ aryloxy group, the substituted $C_6$-$C_{60}$ arylthio group, the substituted $C_1$-$C_{60}$ heteroaryl group, the substituted $C_2$-$C_{60}$ alkylheteroaryl group, the substituted $C_1$-$C_{60}$ heteroaryloxy group, the substituted $C_1$-$C_{60}$ heteroarylthio group, the substituted monovalent non-aromatic condensed polycyclic group, and the substituted monovalent non-aromatic condensed heteropolycyclic group may be:

deuterium, —F, —Cl, —Br, —I, -$CD_3$, -$CD_2H$, -$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, -$CD_3$, -$CD_2H$, -$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, Si($Q_{11}$)($Q_{12}$)($Q_{13}$), —N($Q_{11}$)($Q_{12}$), —C(=O)($Q_{11}$), or any combination thereof;

a $C_3$-$C_{10}$ cycloalkyl group, a $C_1$-$C_{10}$ heterocycloalkyl group, a $C_3$-$C_{10}$ cycloalkenyl group, or a $C_1$-$C_{10}$ heterocycloalkenyl group;

a $C_3$-$C_{10}$ cycloalkyl group, a $C_1$-$C_{10}$ heterocycloalkyl group, a $C_3$-$C_{10}$ cycloalkenyl group, or a $C_1$-$C_{10}$ heterocycloalkenyl group, each substituted with at least one deuterium, —F, —Cl, —Br, —I, -$CD_3$, -$CD_2H$, -$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, —Si($Q_{21}$)($Q_{22}$)($Q_{23}$), —N($Q_{21}$)($Q_{22}$), —C(=O)($Q_{21}$), or any combination thereof; or —Si($Q_{31}$)($Q_{32}$)($Q_{33}$), —N($Q_{31}$)($Q_{32}$), or —C(=O)($Q_{31}$), wherein $Q_1$ to $Q_3$, $Q_{11}$ to $Q_{13}$, $Q_{21}$ to $Q_{23}$, and $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and

* indicates a binding site to a neighboring atom.

Another aspect provides a composition including at least one condensed cyclic compound represented by Formula 1.

Another aspect provides an organic light-emitting device including: a first electrode; a second electrode; and an organic layer placed between the first electrode and the second electrode and including an emission layer, and the organic light-emitting device includes at least one condensed cyclic compound represented by Formula 1.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 3 shows a diagram illustrating an exemplary energy level relationship among a condensed cyclic compound represented by Formula 1, a second compound including an azine group, and a phosphorescent platinum group metal complex in a composition according to an embodiment;

DETAILED DESCRIPTION

Figure 1:
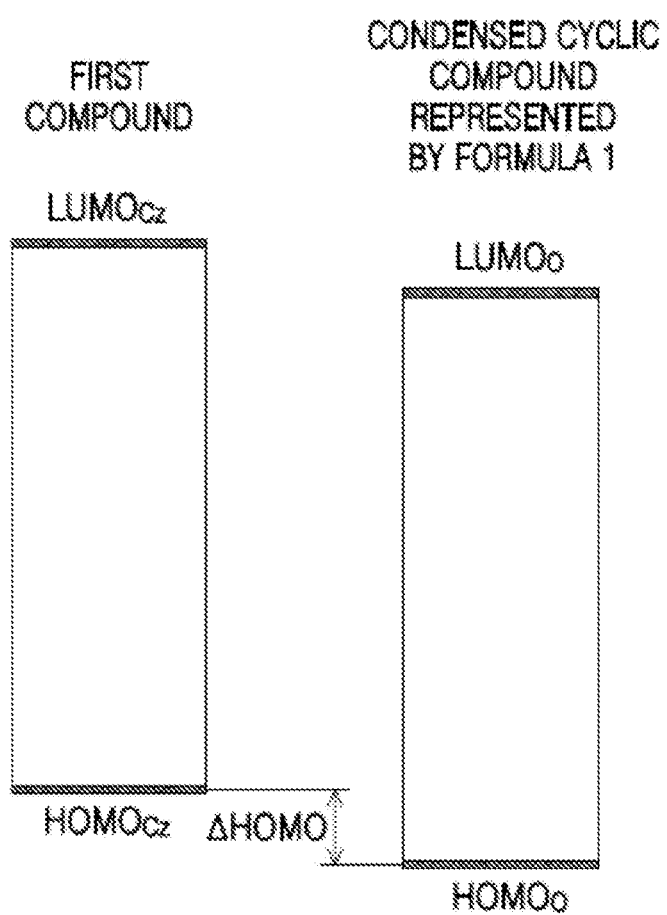
FIG. 1 shows a diagram illustrating an exemplary energy level relationship between a condensed cyclic compound represented by Formula 1 and a first compound including a carbazole group in a composition according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Unless otherwise defined in the present specification, the handling and the measurement of physical properties are carried out under conditions of room temperature (about 20° C. to about 25° C.) and/or the relative humidity of about 40% RH to about 50% RH. In addition, throughout the present specification, the "compound for an organic light-emitting device" may be referred to as the "compound," the "material for an organic light-emitting device" may be referred to as the "material," and the "composition for an organic light-emitting device" may simply be called the "composition."

Condensed Cyclic Compound

A condensed cyclic compound represented by Formula 1 according to an embodiment of the present disclosure will be described in detail as follows:

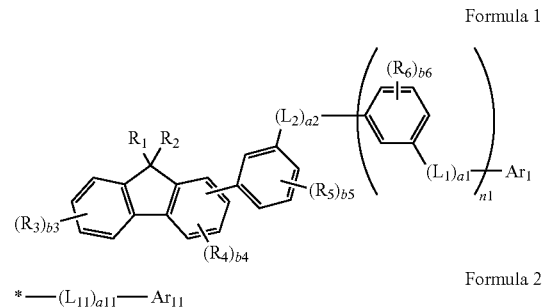

Formula 1

Formula 2

$*—(L_{11})_{a11}—Ar_{11}$

In Formulae 1 and 2, $L_1$, $L_2$, and $L_{11}$ may each independently be a single bond, a substituted or unsubstituted $C_5$-$C_{60}$ carbocyclic group, or a substituted or unsubstituted $C_1$-$C_{60}$ heterocyclic group.

For example, $L_1$, $L_2$, and $L_{11}$ may each independently be:
a single bond, a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphenyl group, a hexaphenyl group, a hexacene group, a rubicene group, a trinaphthalene group, a heptaphenyl group, a pyranthrene group, a pyridine group, a pyrazine group, a pyridazine group, a pyrimidine group, a triazine group, a quinoline group, an isoquinoline group, a quinoxaline group, a quinazoline group, a naphthyridine group, an acridine group, a phenazine group, a benzoquinoline group, a benzoisoquinoline group, a phenanthridine group, a phenanthroline group, a benzoquinone group, a coumarin group, an anthraquinone group, a fluorenone group, a furan group, a thiene group, a silole group, a benzofuran group, a benzothien group, a benzosilole group, a dibenzofuran group, a dibenzothiophene group, a dibenzosilole group, a pyrrole group, an indole group, an isoindole group, a carbazole group, a benzocarbazole group, a dibenzocarbazole group, an imidazole group, a benzimidazole group, a pyrazole group, a triazole group, a tetrazole group, an indazole group, an oxazole group, an isoxazole group, a benzoxazole group, a benzisoxazole group, a thiazole group, an isothiazole group, a benzothiazole group, a benzisothiazole group, an imidazopyridine group, an imidazopyrimidine group, an imidazophenanthridine group, a benzimidazophenanthridine group, an azadibenzofuran group, an azacarbazole group, an azadibenzothien group, a diazadibenzofuran group, a diazacarbazole group, a diazadibenzothien group, a xanthonene group, or a thioxanthone group; or a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphenyl group, a hexaphenyl group, a hexacene group, a rubicene group, a trinaphthalene group, a heptaphenyl group, a pyranthrene group, a pyridine group, a pyrazine group, a pyridazine group, a pyrimidine group, a triazine group, a quinoline group, an isoquinoline group, a quinoxaline group, a quinazoline group, a naphthyridine group, an acridine group, a phenazine group, a benzoquinoline group, a benzoisoquinoline group, a phenanthridine group, a phenanthroline group, a benzoquinone group, a coumarin group, an anthraquinone group, a fluorenone group, a furan group, a thiene group, a silole group, a benzofuran group, a benzothien group, a benzosilole group, a dibenzofuran group, a dibenzothiophene group, a dibenzosilole group, a pyrrole group, an indole group, an isoindole group, a carbazole group, a benzocarbazole group, a dibenzocarbazole group, an imidazole group, a benzimidazole group, a pyrazole group, a triazole group, a tetrazole group, an indazole group, an oxazole group, an isoxazole group, a benzoxazole group, a benzisoxazole group, a thiazole group, an isothiazole group, a benzothiazole group, a benzisothiazole group, an imidazopyridine group, an imidazopyrimidine group, an imidazophenanthridine group, a benzimidazophenanthridine group, an azadibenzofuran group, an azacarbazole group, an azadibenzothien group, a diazadibenzofuran group, a diazacarbazole group, a diazadibenzothien group, a xanthonene group, or a thioxanthone group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazacarbazolyl group, a diazadibenzothienyl group, a xanthonenyl group, a thioxanthonyl group, or any combination thereof.

For example, $L_1$, $L_2$, and $L_{11}$ may each independently be:

a single bond, a benzene group, a biphenyl group, a terphenyl group, or a tetraphenyl group; or a benzene group, a biphenyl group, a terphenyl group, or a tetraphenyl group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a biphenyl group, a terphenyl group, or any combination thereof.

For example, L₁, L₂, and L₁₁ may each independently be a single bond or a group represented by Formulae 3-1 to 3-7 below:

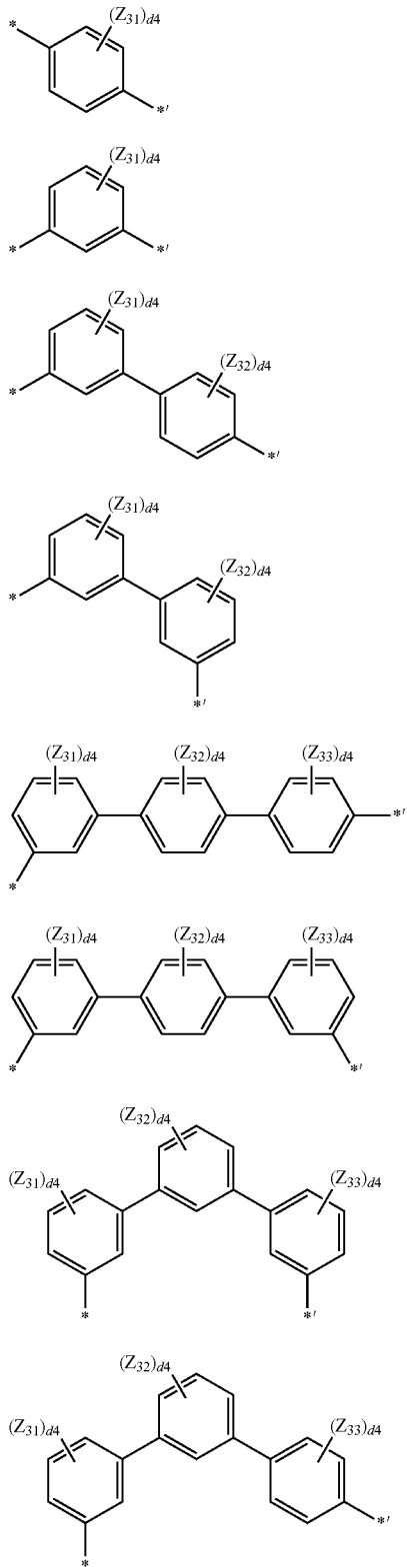

In Formulae 3-1 to 3-7, $Z_{31}$ to $Z_{33}$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, or —Si($Q_{31}$)($Q_{32}$)($Q_{33}$), d4 may be an integer from 0 to 4, $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and

* and *' each indicate a binding site to a neighboring atom.

The designations a1, a2, and a11 in Formulae 1 and 2 may each independently be an integer from 1 to 5. a1 represents the number of groups represented by L₁, and when a1 is 2 or more, L₁(s) in the number of a1 may be identical to or different from each other, a2 represents the number of groups represented by L₂, and when a2 is 2 or more, L₂(s) in the number of a2 may be identical to or different from each other, and a11 represents the number of groups represented by L₁₁, and when a11 is 2 or more, L₁₁(s) in the number of a11 may be identical to or different from each other.

For example, a1, a2, and a11 may each be an integer from 1 to 2, but embodiments of the present disclosure are not limited thereto.

In Formulae 1 and 2, Ar₁ and Ar₁₁ may each independently be a substituted or unsubstituted $C_5$-$C_{60}$ carbocyclic group, wherein Ar₁ is not a triphenylene group or a fluorene group connected at the $9^{th}$ position.

For example, Ar₁ and Ar₁₁ may each independently be:

a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, or a pyranthrenyl group; or a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, or a pyranthrenyl group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, or any combination thereof.

For example, $Ar_1$ and $Ar_{11}$ may each independently be:
a phenyl group, a naphthyl group, a fluorenyl group, a spiro-bifluorenyl group, a biphenyl group, a terphenyl group, or a tetraphenyl group; or
a phenyl group, a naphthyl group, a fluorenyl group, a spiro-bifluorenyl group, a biphenyl group, a terphenyl group, or a tetraphenyl group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a biphenyl group, a terphenyl group, or any combination thereof.

For example, $Ar_1$ and $Ar_{11}$ may each independently be a group represented by Formulae 4-1 to 4-9 below:

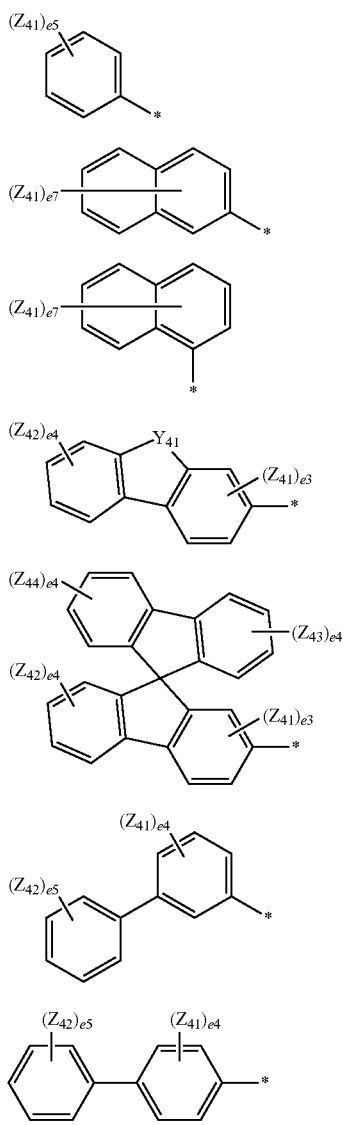

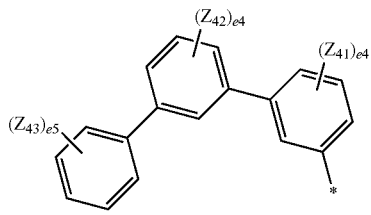

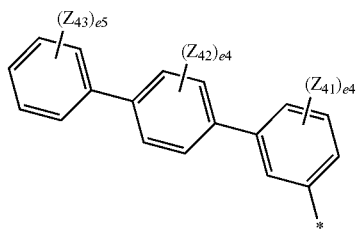

In Formulae 4-1 to 4-9,
$Y_{41}$ may be $C(Z_{45})(Z_{46})$,
$Z_{41}$ to $Z_{46}$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a phenyl group, or —$Si(Q_{31})(Q_{32})(Q_{33})$,
e3 may be an integer from 0 to 3,
e4 may be an integer from 0 to 4,
e5 may be an integer from 0 to 5,
e7 may be an integer from 0 to 7,
$Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and
* indicates a binding site to a neighboring atom.

For example, a moiety represented by

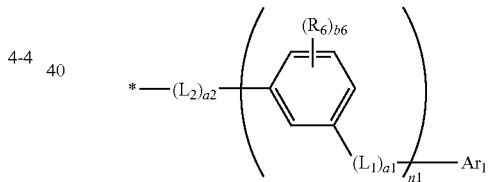

may be a group represented by one of Formulae 5-1 to 5-22 below, but embodiments of the present disclosure are not limited thereto:

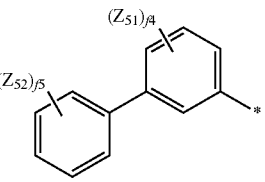

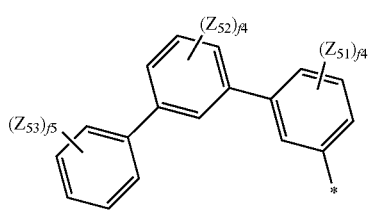

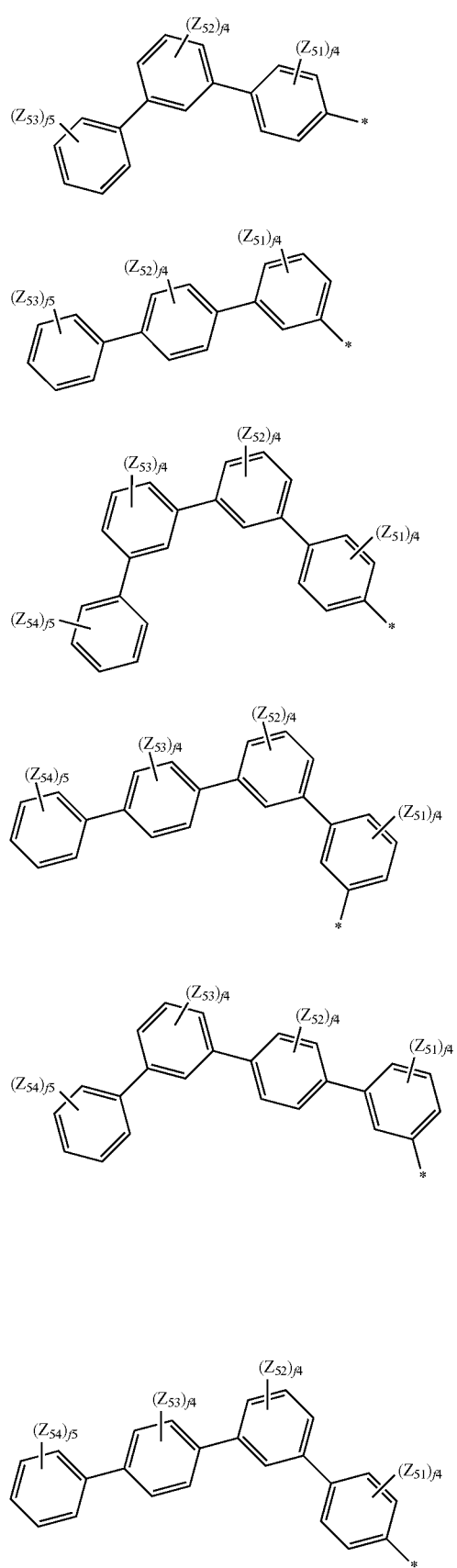
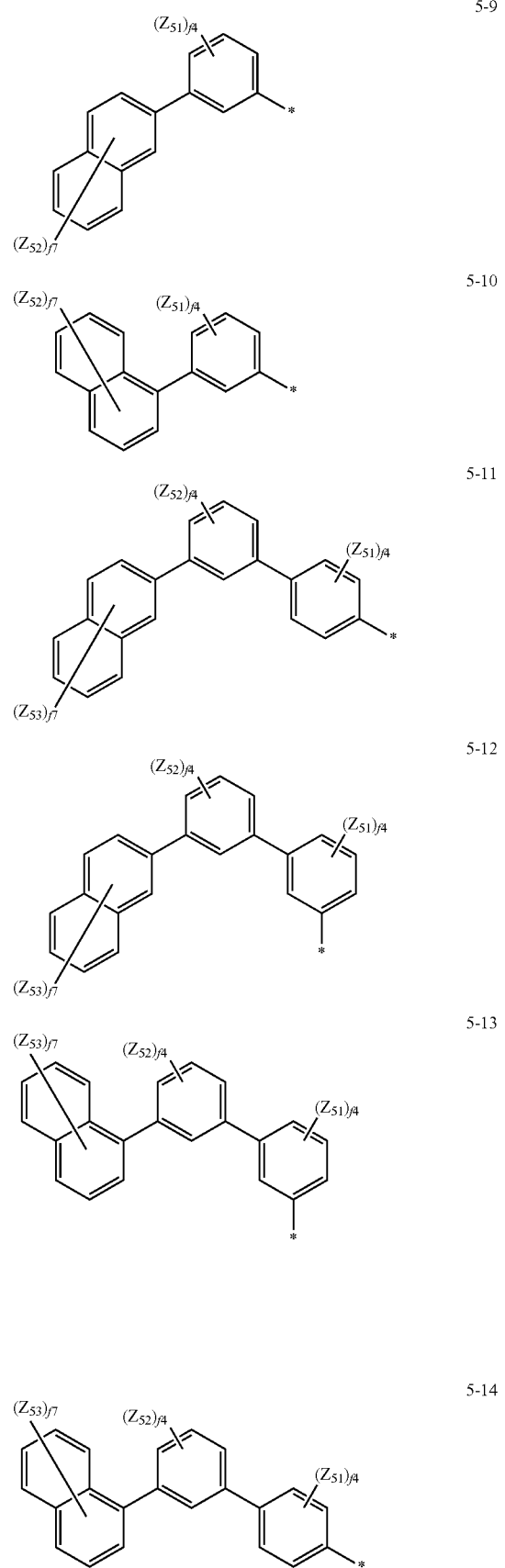

-continued 5-15
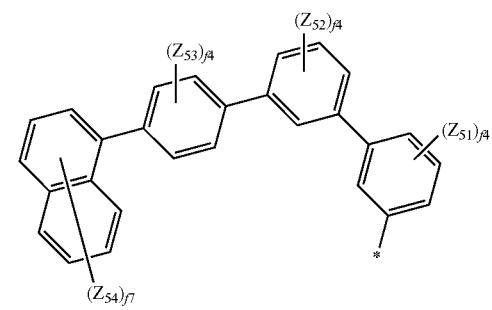

5-16
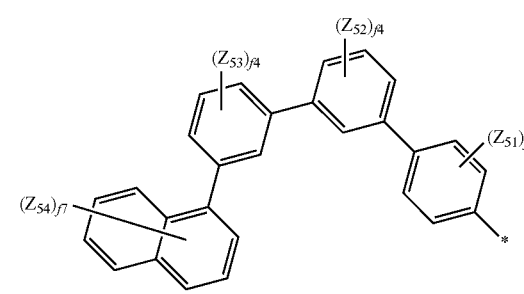

5-17
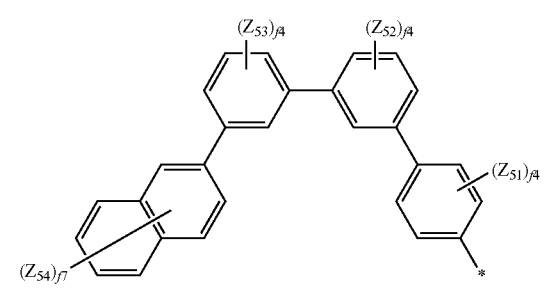

5-18
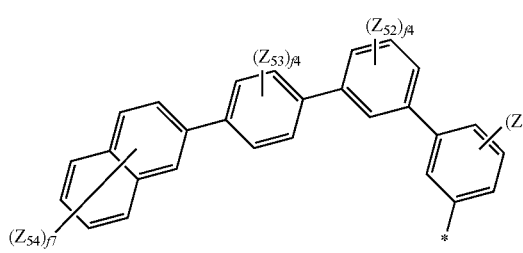

5-19
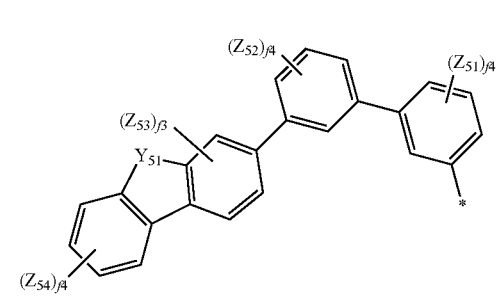

-continued 5-20
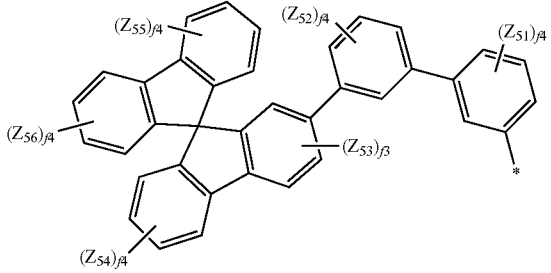

5-21
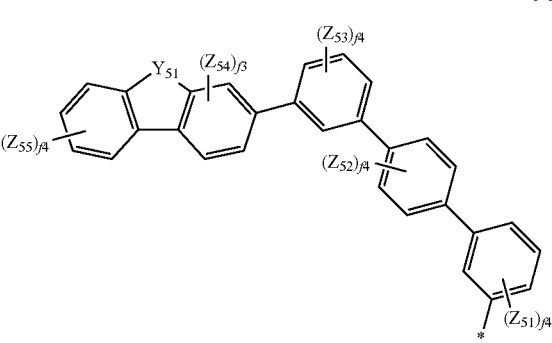

5-22
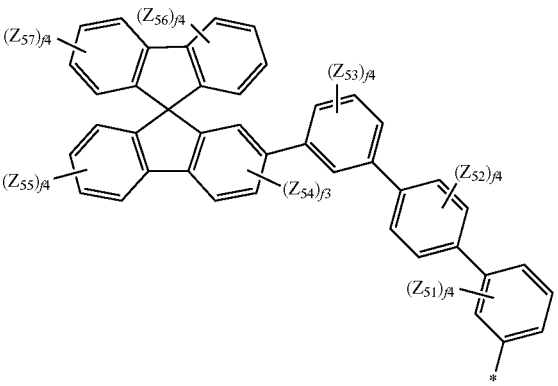

In Formulae 5-1 to 5-22,
$Y_{51}$ may be $C(Z_{58})(Z_{59})$,
$Z_{51}$ to $Z_{59}$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a phenyl group, or —Si($Q_{31}$)($Q_{32}$)($Q_{33}$),
f3 may be an integer from 0 to 3,
f4 may be an integer from 0 to 4,
f5 may be an integer from 0 to 5,
f7 may be an integer from 0 to 7,
$Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group, and
* indicates a binding site to a neighboring atom.

In Formulae 1 and 2, $R_1$ to $R_6$ may each independently be a group represented by Formula 2, hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_7$-$C_{60}$ arylalkyl group, a substituted or unsubstituted $C_7$-$C_{60}$ arylalkyloxy group, a substituted or unsubstituted $C_7$-$C_{60}$ arylalkylthio group, a substituted or unsubstituted $C_8$-$C_{60}$ arylalkenyl group, a substituted or unsubstituted $C_8$-$C_{60}$ arylalkynyl group, a substituted or unsubstituted $C_1$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), or —N($Q_1$)($Q_2$), b3, b5, and b6 may each independently be an integer from 0 to 4, b2 may be an integer from 0 to 3, any two adjacent groups among $R_1$, $R_2$, $R_3$(s) in the number of b3, $R_4$(s) in the number of b4, $R_5$(s) in the number of b5, and $R_6$(s) in the number of b6 may optionally be linked to each other to form a substituted or unsubstituted $C_5$-$C_{30}$ carbocyclic group or a substituted or unsubstituted $C_1$-$C_{30}$ heterocyclic group.

For example, $R_1$ to $R_6$ may each independently be: hydrogen, deuterium, —F, —Cl, —Br, —I, a cyano group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, or a naphthyl group, each substituted with at least one deuterium, —F, —Cl, —Br, —I, a cyano group, a phenyl group, a biphenyl group, a terphenyl group, or any combination thereof.

For example, $R_1$ and $R_2$ may each independently be: hydrogen, a $C_1$-$C_{20}$ alkyl group, a phenyl group, a naphthyl group, $C_1$-$C_{20}$ alkyl group, a phenyl group, or a naphthyl group, each substituted with at least one deuterium, —F, —Cl, —Br, —I, a cyano group, a phenyl group, a biphenyl group, a terphenyl group, or any combination thereof.

For example, $R_3$ to $R_6$ may each independently be hydrogen, a $C_1$-$C_{20}$ alkyl group, or a phenyl group.

For example, when any two adjacent groups among $R_1$, $R_2$, $R_3$(s) in the number of b3, $R_4$(s) in the number of b4, $R_5$(s) in the number of b5, and $R_6$(s) in the number of b6 may optionally be linked to each other to form a $C_5$-$C_{30}$ carbocyclic group or a $C_1$-$C_{30}$ heterocyclic group, the $C_5$-$C_{30}$ carbocyclic group or the $C_1$-$C_{30}$ heterocyclic group does not include any substituent other than hydrogen.

In Formulae 1 and 2, n1 may be an integer from 1 to 5.

For example, n1 may be 1 or 2.

In one or more embodiments, the group represented by Formula 1 may be represented by Formula 1A below:

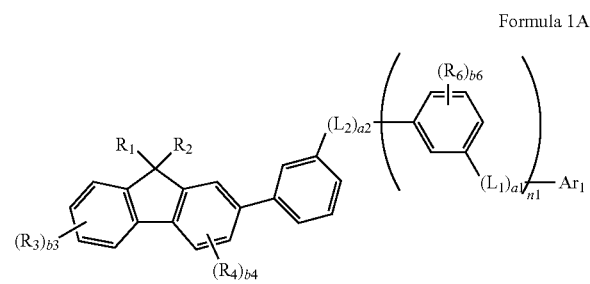

Formula 1A

In Formula 1A, $L_1$, $L_2$, a1, a2, $Ar_1$, $R_1$ to $R_6$, b3 to b6, and n1 may each be understood by referring to descriptions thereof provided herein.

In one or more embodiments, the condensed cyclic compound represented by Formula 1 may be a group represented by one of Formulae 1-1 to 1-8 below:

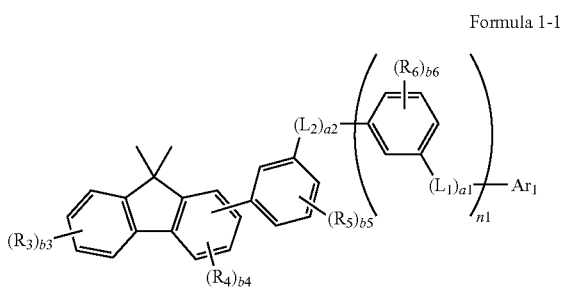

Formula 1-1

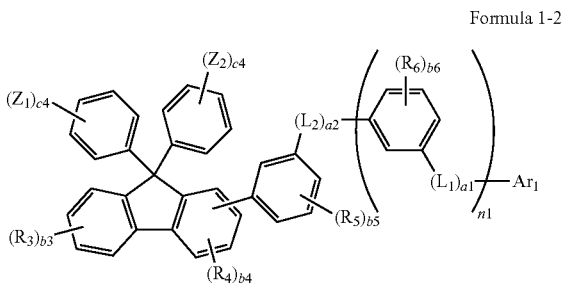

Formula 1-2

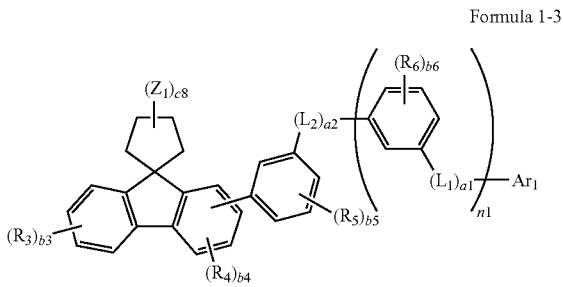

Formula 1-3

-continued

Formula 1-4
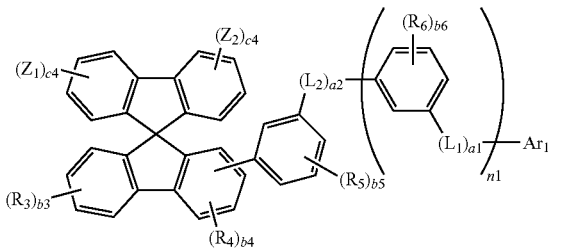

Formula 1-5
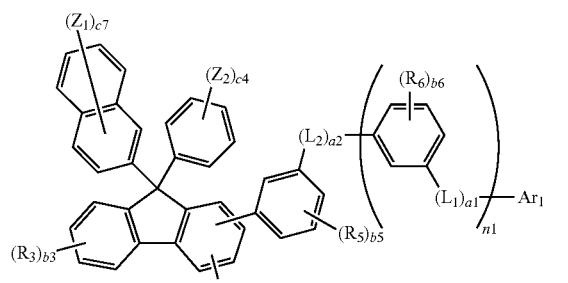

Formula 1-6
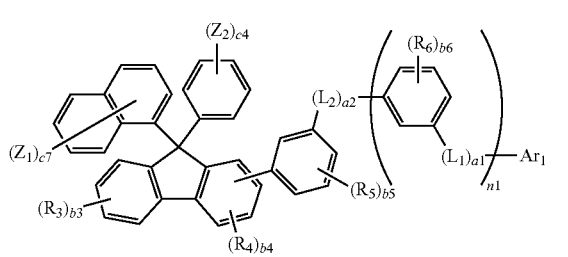

Formula 1-7
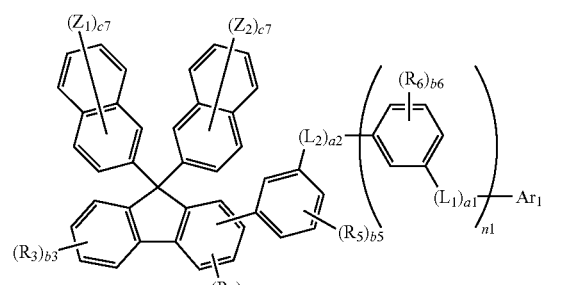

Formula 1-8
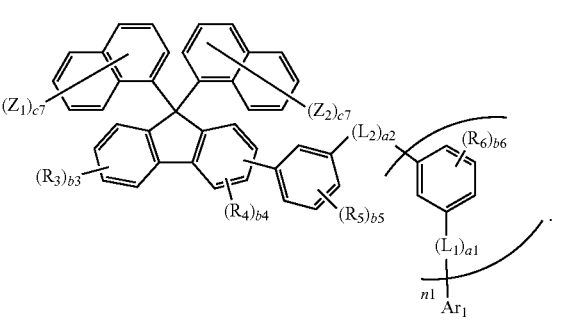

In Formulae 1-1 to 1-8, $L_1$, $L_2$, a1, a2, $Ar_1$, $R_3$ to $R_6$, b3 to b6, and n1 may each be understood by referring to descriptions thereof provided herein, $Z_1$ and $Z_2$ may each independently be hydrogen, deuterium, —F, —Cl, —Br, —I, a hydroxyl group, a cyano group, a $C_1$-$C_{20}$ alkyl group, a $C_1$-$C_{20}$ alkoxy group, a phenyl group, or —Si($Q_{31}$)($Q_{32}$)($Q_{33}$), c4 may be an integer from 0 to 4, c7 may be an integer from 0 to 7, c8 may be an integer from 0 to 8, and $Q_{31}$ to $Q_{33}$ may each independently be hydrogen, deuterium, a $C_1$-$C_{20}$ alkyl group, a $C_1$-$C_{20}$ alkoxy group, a phenyl group, or a biphenyl group.

For example, the condensed cyclic compound represented by Formula 1 may not include an ortho-phenyl group, but embodiments of the present disclosure are not limited thereto.

For example, the condensed cyclic compound represented by Formula 1 may include m-phenyl moieties in the number of 6 or less.

For example, the condensed cyclic compound represented by Formula 1 may not include a hetero atom, but embodiments of the present disclosure are not limited thereto.

For example, the condensed cyclic compound represented by Formula 1 may have an asymmetric structure with respect to a fluorene group, but embodiments of the present disclosure are not limited thereto.

For example, the glass transition temperature ($T_g$) of the condensed cyclic compound represented by Formula 1 may be 140° C. or less. For example, $T_g$ of the condensed cyclic compound is not particularly limited, but may be 130° C. or less, 60° C. or more, and 100° C. or more.

In one or more embodiments, the condensed cyclic compound represented by Formula 1 may be of Compounds 1 to 60 below, but embodiments of the present disclosure are not limited thereto:

1

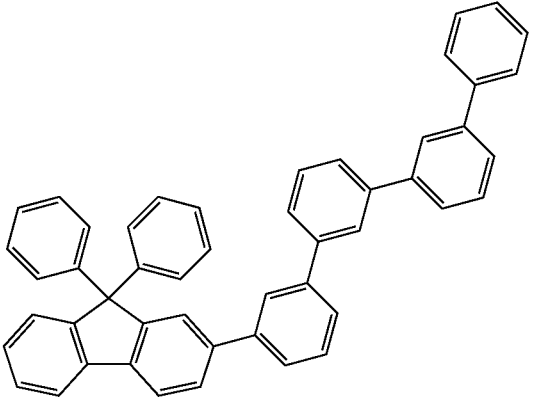

2

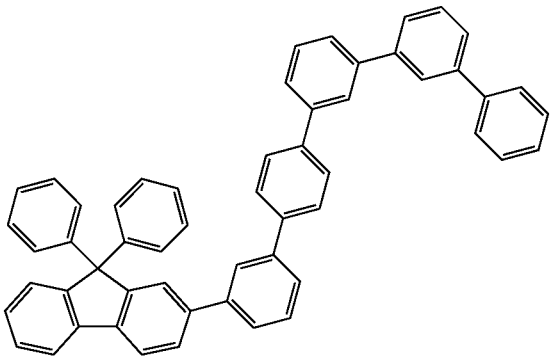

3
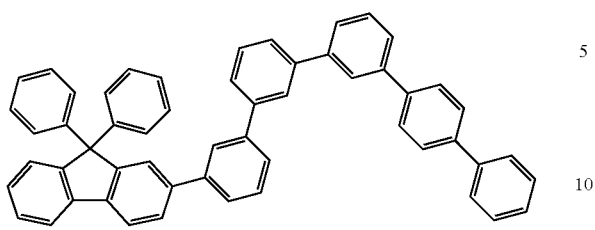
4
5
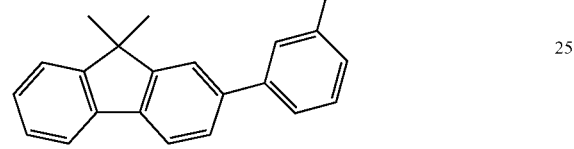
6
7
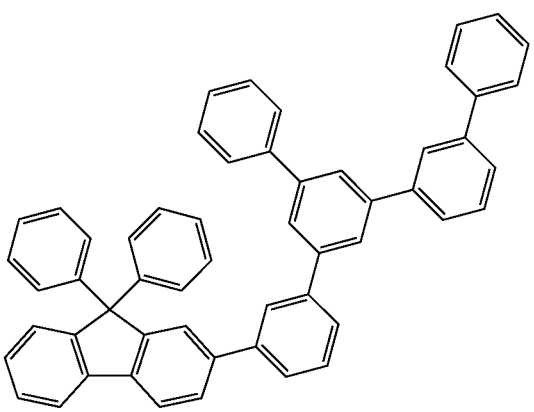
8
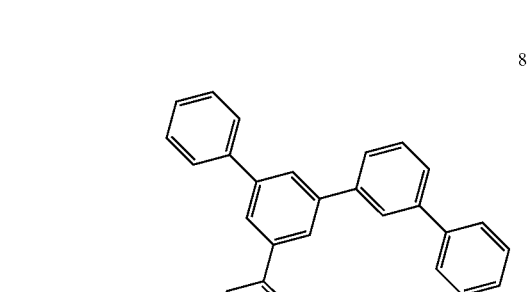
9
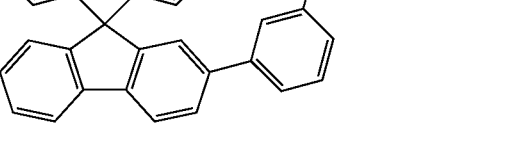

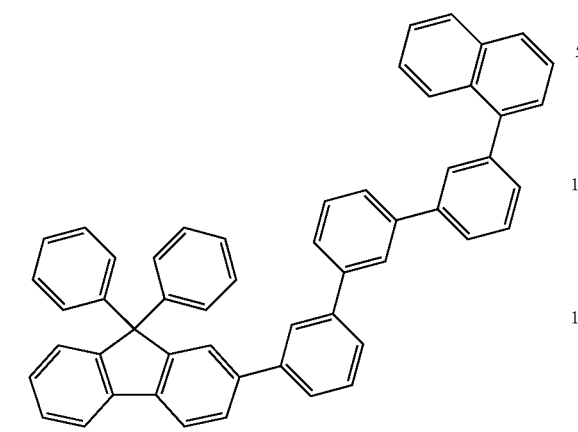
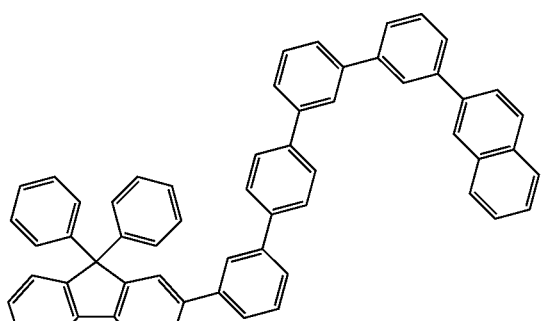
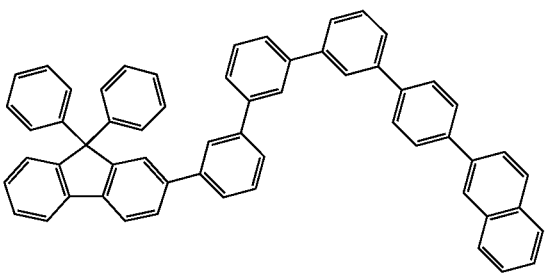
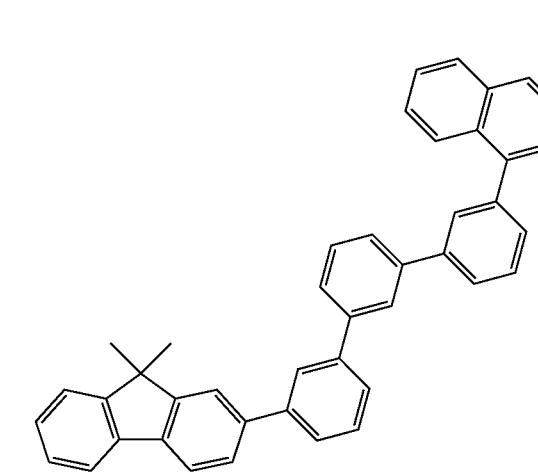
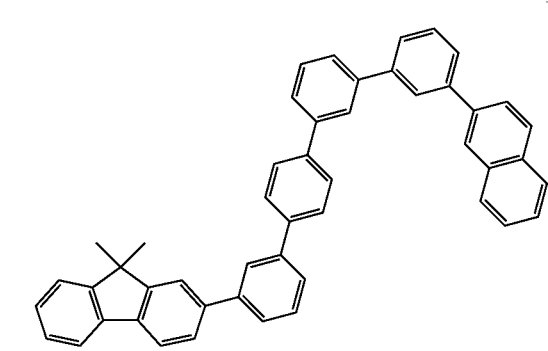

-continued
18
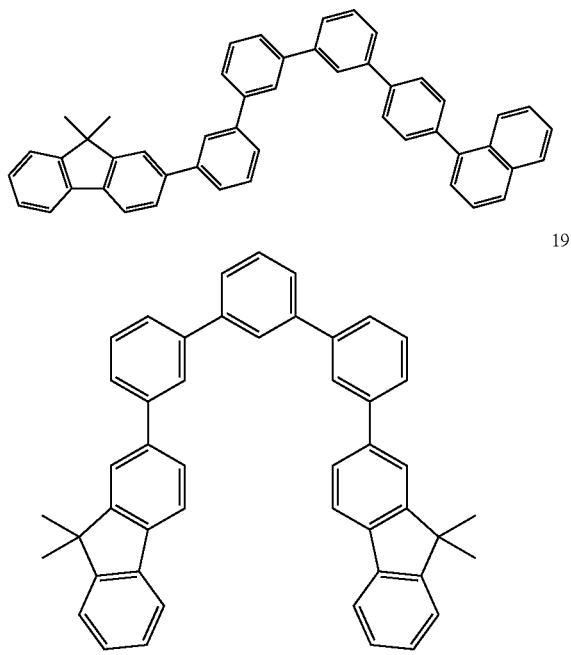
19
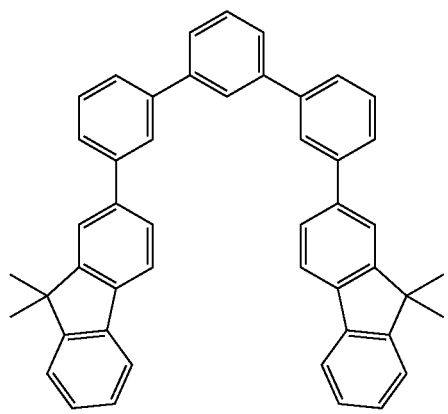
20
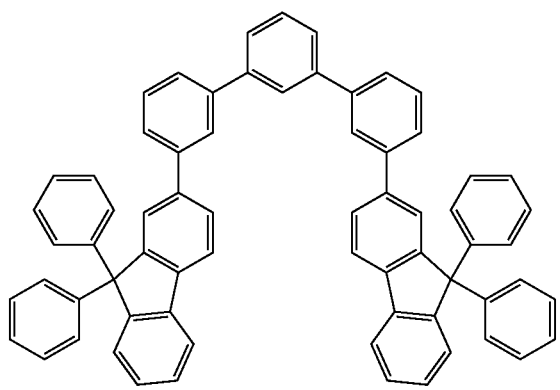
21
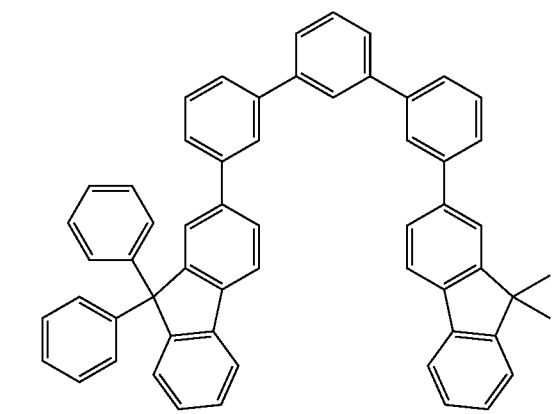
-continued
22
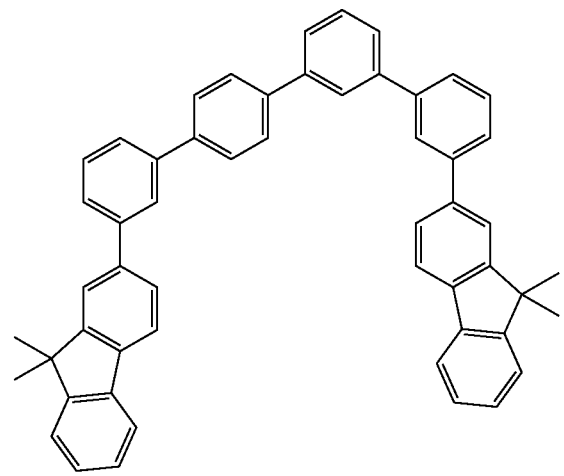
23
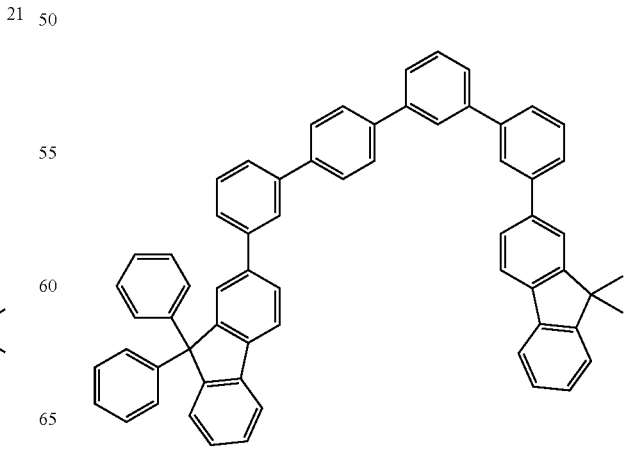
24

25
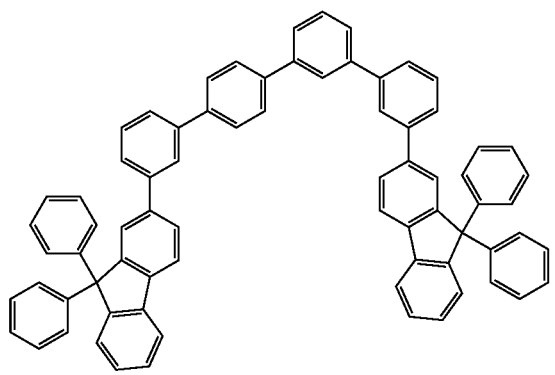
26
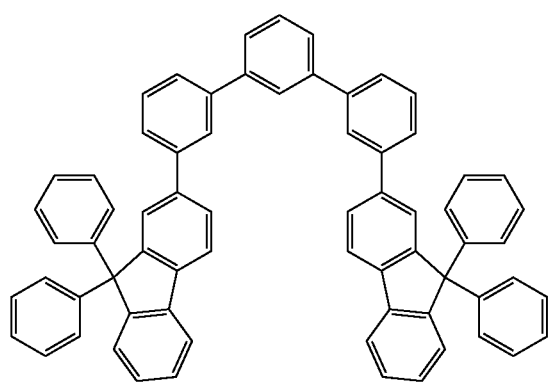
27
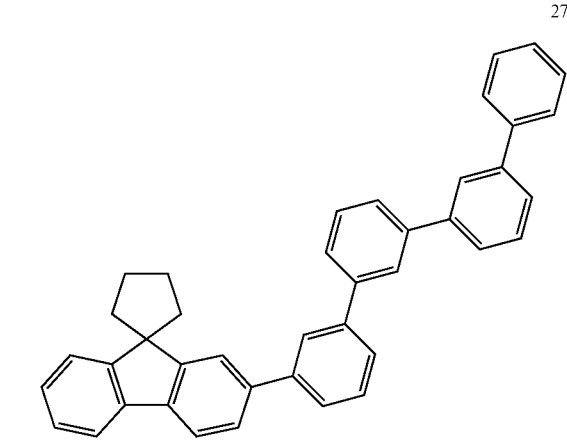
28
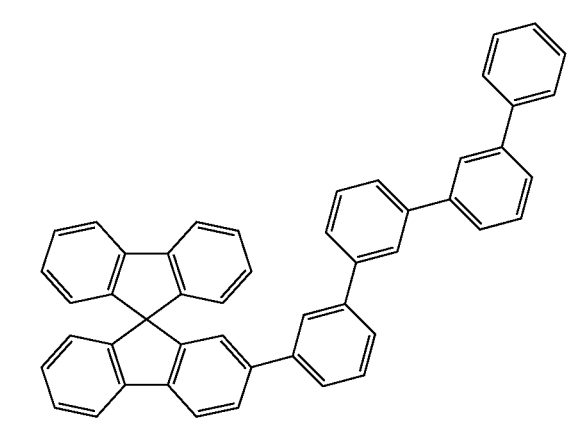
29
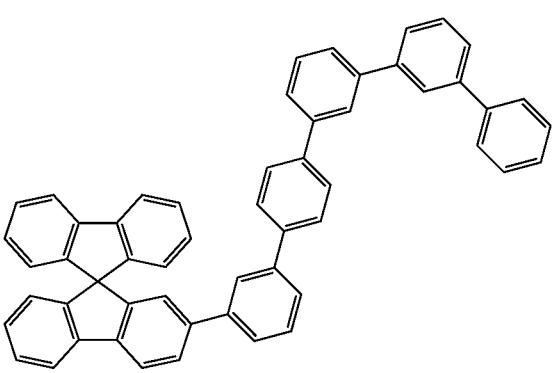
30
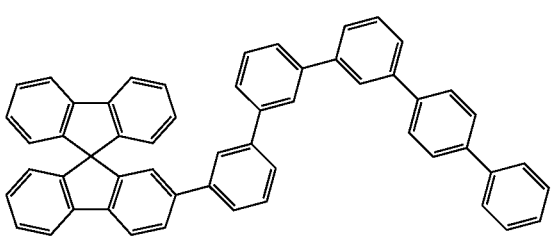
31
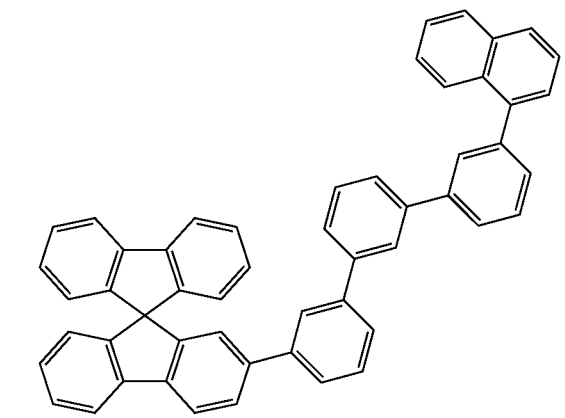
32
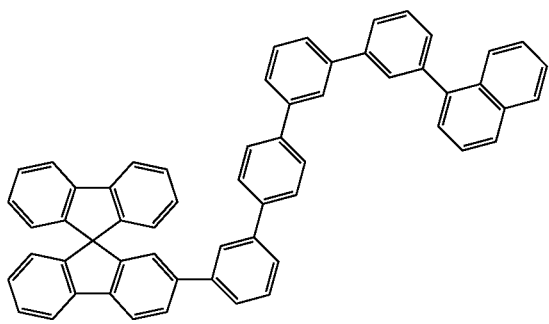

33
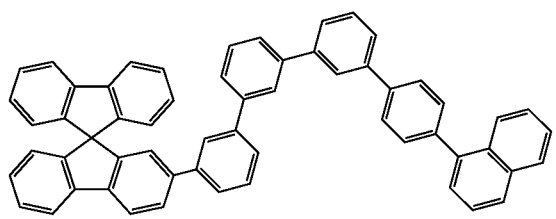
34
35
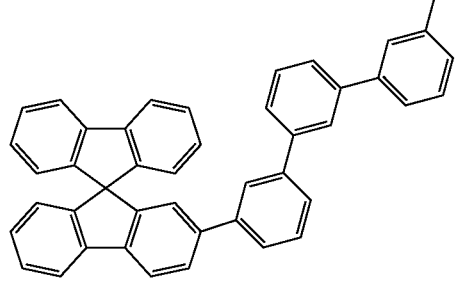
36
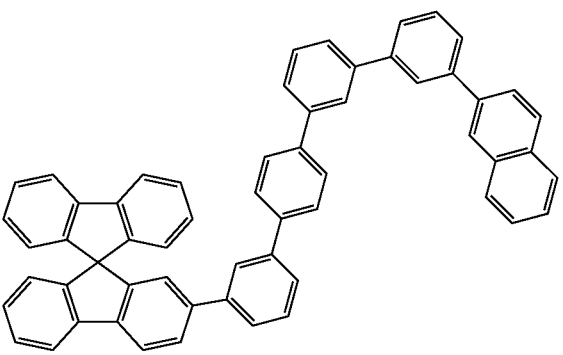
37
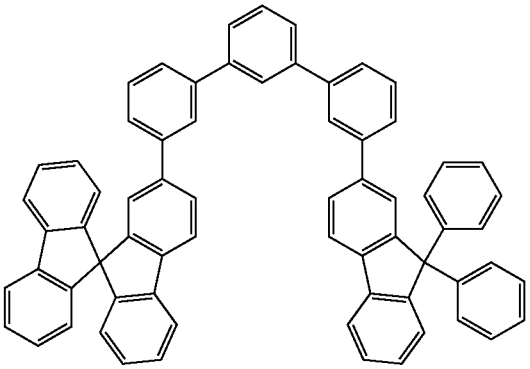
38
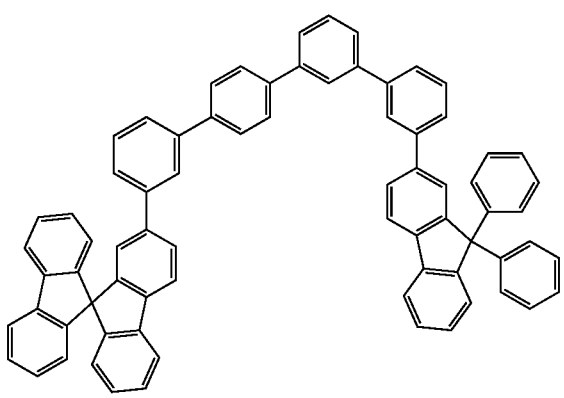
39
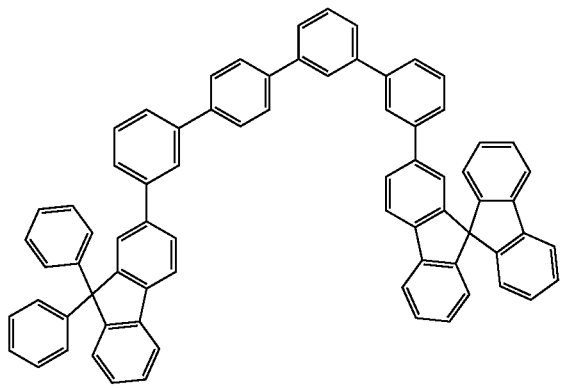
40
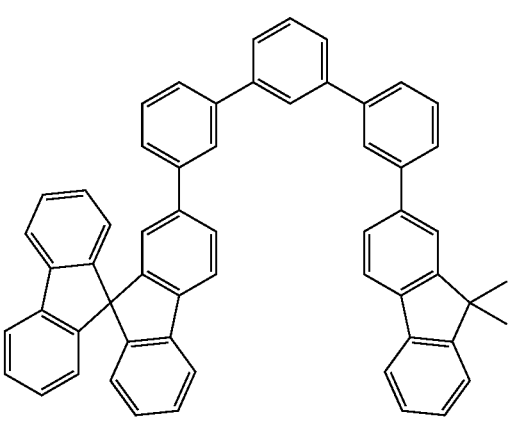

41
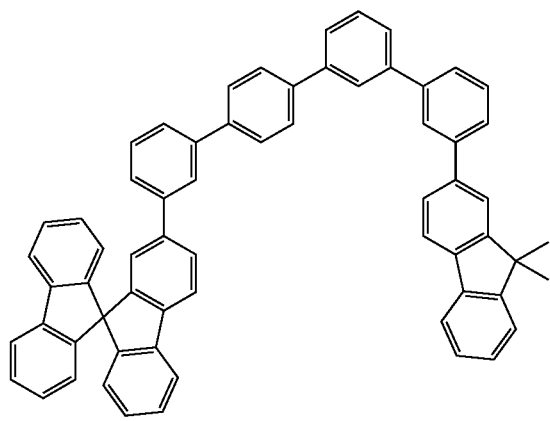
42
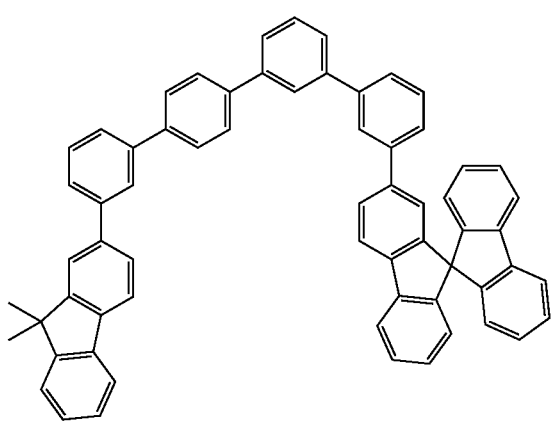
43
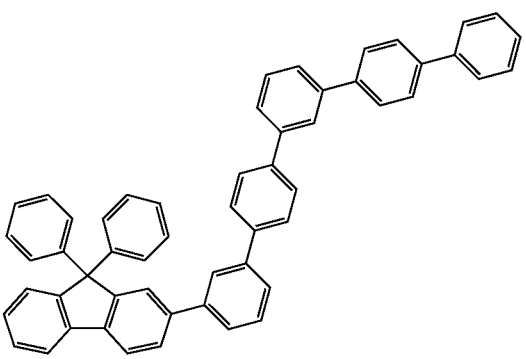
44
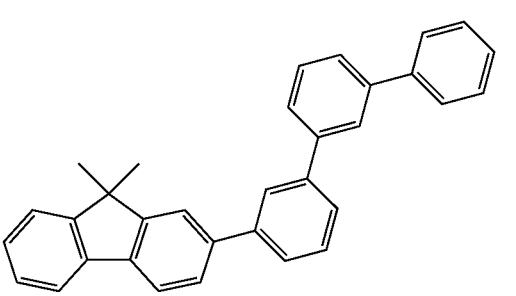
45
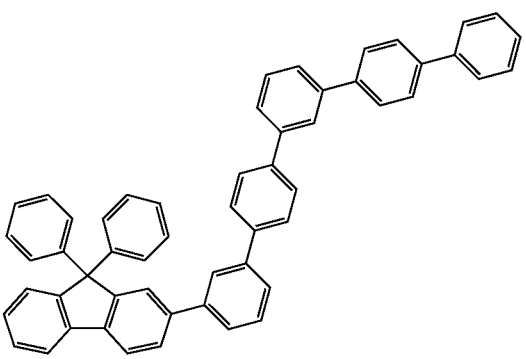
46
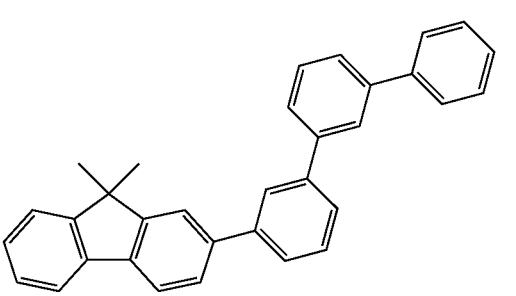
47
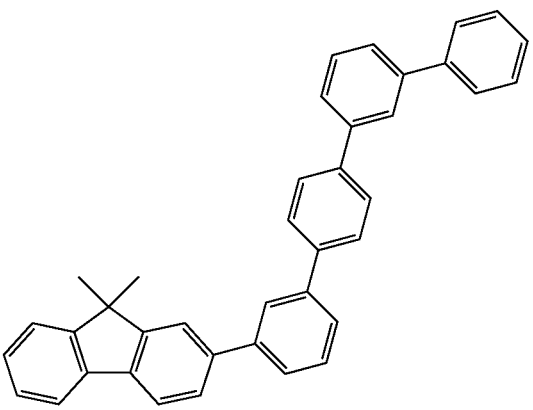
48
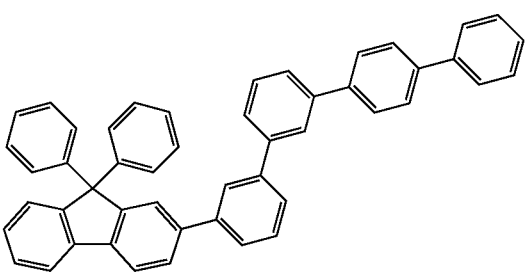

49
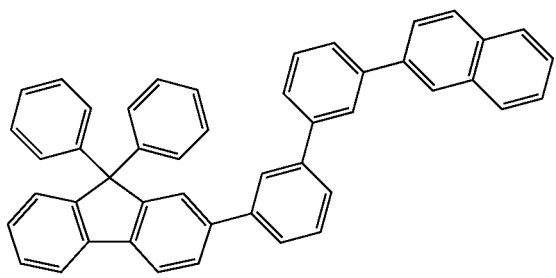
50
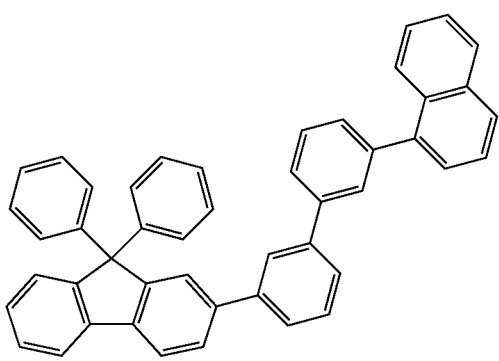
51
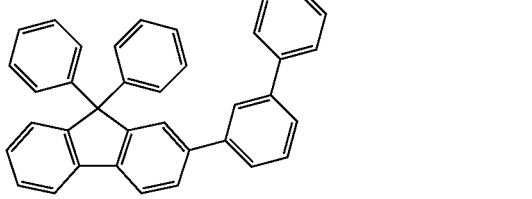
52
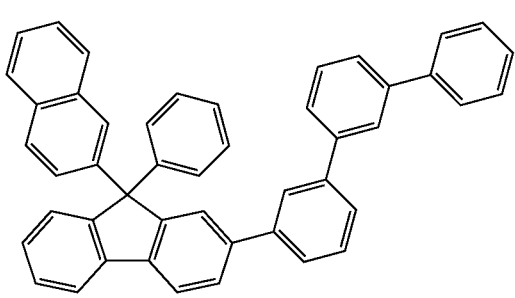
53
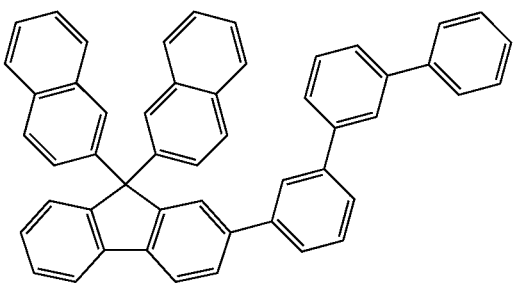
54
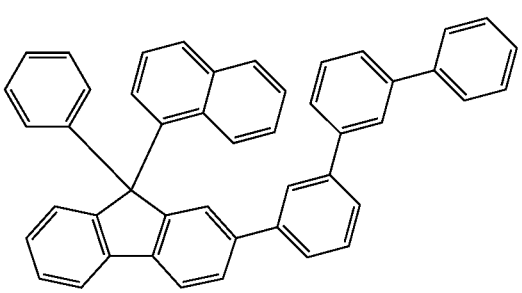
55
56
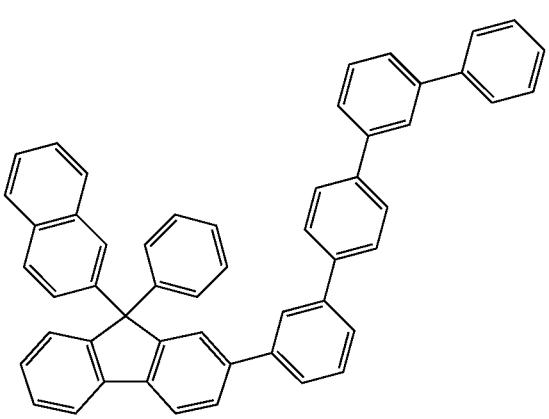

-continued

57

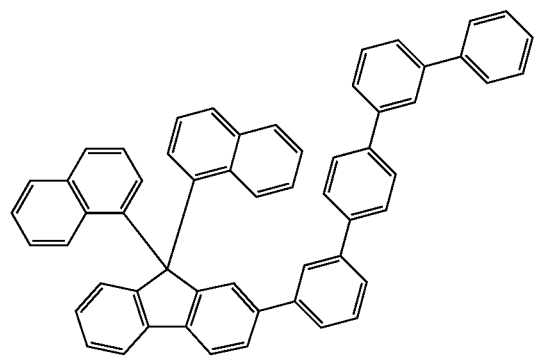

58

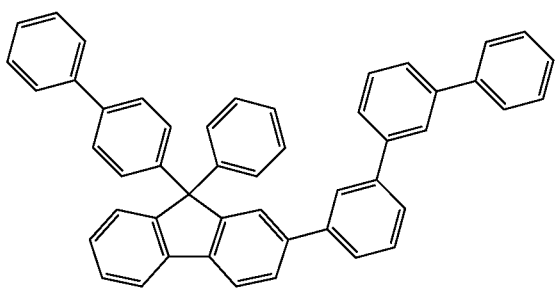

59

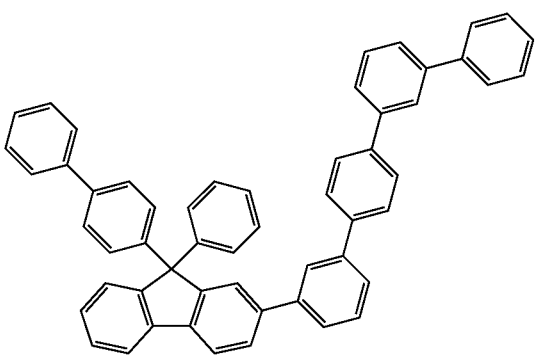

60

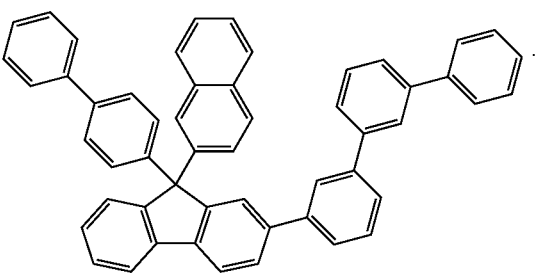

For example, the condensed cyclic compound may be Compound 43 or 44, but embodiments of the present disclosure are not limited thereto.

Thus, the condensed cyclic compound has the balance between the highest occupied molecular orbital (HOMO) level and the lowest unoccupied molecular orbital (LUMO) level and the balance of the carrier mobility between electrons and holes. As a result, since, with respect to the layer including the condensed cyclic compound, a portion in which charges recombine and a portion in which excitons are generated are dispersed, and loads are dispersed, the lifespan of the organic light-emitting device is improved.

In addition, due to the inclusion of a phenyl group or a naphthyl group as $Ar_1$, the condensed cyclic compound has low glass transition temperature ($T_g$) and high triplet excitation energy. Accordingly, luminescent efficiency and light-emission lifespan thereof are improved and the removal of volatile impurities in the drying process may be promoted.

$T_g$ may be for example, from about 50° C. to about 120° C., for example, about 60° C. to about 110° C., or for example, about 60° C. to about 100° C.

The triplet excitation energy may be, for example, about 2.4 eV or more, for example, about 2.5 eV or more, or for example, about 2.6 eV or more.

In addition, regarding the condensed cyclic compound, when a1 and a2 are each 1, $L_1$ and $L_2$ are each a single bond, and n1 is 1, $Ar_1$ is not a fluorene group, Therefore, although the available conformation number is relatively reduced, condensed cyclic groups with large π-planes interact less, leading to a decrease in the aggregation of molecules, a longer pot life of the solution, or a lower glass transition temperature. Accordingly, the removal of volatile impurities in the drying process is promoted, and the light-emission lifespan is prolonged.

In addition, the condensed cyclic compound does not include a fluorene group linked at the $9^{th}$ position as $Ar_1$. Here, the $9^{th}$ position refers to a portion indicated by a dotted line in the following fluorene group.

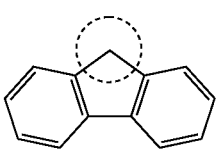 [SMILES: c1ccc2c(c1)Cc1ccccc1-2]

Since the fluorene group linked at the $9^{th}$ position does not have a π conjugate effect, an electron conduction level close to the LUMO or the LUMO is not formed, and only a glass transition temperature may be increased. That is, when the fluorene group linked at the $9^{th}$ position is included, it is difficult to remove the volatile impurities and a light-emission lifespan may be reduced.

The condensed cyclic compound includes two or more meta phenyl moieties. As a result, the number of conformations that a molecule can have is increased, and the aggregation by the interaction between molecules may be further reduced.

For example, the condensed cyclic compound represented by Formula 1 may include m-phenyl moieties in the number of 6 or less. Thus, the glass transition temperature is adjusted not to be lower than a certain level.

The condensed cyclic compound represented by Formula 1 may not optionally include a heteroatom. When the condensed cyclic compound contains a heteroatom, at least one of the HOMO and LUMO energy levels changes, and thus, the injectability or transportability of holes or electrons is likely to be enhanced, resulting in focusing of a load at the interface between an emission layer and a layer adjacent thereto and a shorter light-emission lifespan.

The condensed cyclic compound represented by Formula 1 may not optionally include o-terphenyl group. Due to the absence of the group, a light-emission lifespan may be increased.

The condensed cyclic compound represented by Formula 1 may be used in an organic layer between a pair of electrodes of an organic light-emitting device. For example, the condensed cyclic compound represented by Formula 1 may be included in an emission layer, and may be suitable as a host.

The condensed cyclic compound represented by Formula 1 may provide high luminescent efficiency and luminance lifespan. The reason for this is considered to be that the condensed cyclic compound represented by Formula 1 has a low glass transition temperature, a low LUMO level, and good balance of carrier mobility between electrons and holes.

In addition, the condensed cyclic compound represented by Formula 1 is difficult to precipitate in the solution, and the pot life of the solution is enhanced. Thus, even when a wet film-forming method is used, the condensed cyclic compound may provide an organic light-emitting device having high luminescent efficiency and light-emission lifespan.

The condensed cyclic compound represented by Formula 1 may be synthesized by using a known organic synthetic method. For example, the condensed cyclic compound represented by Formula 1 may be synthesized by Suzuki-Miyaura coupling reactions. A synthesis method for the condensed cyclic compound represented by Formula 1 would be apparent to those of ordinary skill in the art by referring to the following examples.

Composition

Hereinafter, a composition according to an embodiment will be described in detail as follows.

The composition may include at least one of the condensed cyclic compound represented by Formula 1.

The condensed cyclic compound represented by Formula 1 may be used in an organic layer between a pair of electrodes of an organic light-emitting device. For example, the condensed cyclic compound represented by Formula 1 may be included in an emission layer, and may be suitable as a host.

The condensed cyclic compound may provide high luminance efficiency and luminance lifespan. The reason for this is considered to be that the condensed cyclic compound represented by Formula 1 has a low glass transition temperature, a low LUMO level, and good balance of carrier mobility between electrons and holes.

In addition, the condensed cyclic compound is difficult to precipitate in the solution, and the pot life of the solution is long. Thus, even when a wet film-forming method is used, the condensed cyclic compound may provide an organic light-emitting device having high luminescent efficiency and light-emission lifespan of the organic light-emitting device.

For example, the composition may further include a first compound containing a carbazole-based moiety.

For example, the composition may further include a second compound containing an azine-based moiety.

For example, the composition may further include a luminescent material.

For example, the composition may further include one or more of a first compound including a carbazole-based moiety, a second compound including an azine-based moiety, and a luminescent material.

For example, the amount of the condensed cyclic compound in the composition may be from about 5 wt % to about 95 wt %, for example, about 10 wt % to about 90 wt %, for example, about 20 wt % to about 80 wt %, based on the total weight of the composition.

Within these ranges, the solubility of the condensed cyclic compound is further improved, and precipitation thereof is less likely to occur in the solution, resulting in a longer pot life of the solution. Further, the luminescent efficiency and light-emission lifespan of organic light-emitting devices are improved.

Hereinafter, the luminescent material, and the first compound and the second compound will be described in detail.

The first compound includes a carbazole-based moiety as described above. That is, the composition according to an embodiment of the present disclosure may contain a carbazole-based moiety to further increase the effect of inhibiting aggregation of molecules, and also to improve the balance of carrier mobility between electrons and holes. Thus, the solubility of the composition is further increased, and precipitation hardly occurs in the solution, and thus, the pot life of the solution may be prolonged. Further, the luminescent efficiency and light-emission lifespan of organic light-emitting devices are improved.

For example, the composition may further include a first compound represented by Formula 9 and a second compound represented by Formula 10:

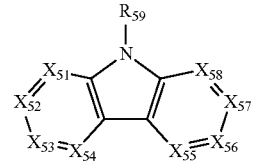

Formula 9

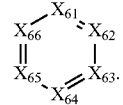

Formula 10>

In Formulae 9 and 10, $X_{51}$ may be N or $C(R_{51})$; $X_{52}$ may be N or $C(R_{52})$; $X_{53}$ may be N or $C(R_{53})$; $X_{54}$ may be N or $C(R_{54})$; $X_{55}$ may be N or $C(R_{55})$; $X_{56}$ may be N or $C(R_{56})$; $X_{57}$ may be N or $C(R_{57})$; $X_{58}$ may be N or $C(R_{58})$;

$X_{61}$ may be N or $C(R_{61})$; $X_{62}$ may be N or $C(R_{62})$; $X_{63}$ may be N or $C(R_{63})$; $X_{64}$ may be N or $C(R_{64})$; $X_{65}$ may be N or $C(R_{65})$; and $X_{66}$ may be N or $C(R_{66})$, and at least one of $X_{61}$ to $X_{66}$ may be N;

$R_{51}$ to $R_{58}$ and $R_{61}$ to $R_{66}$ may each independently be hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, $R_{59}$ may be a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and at least one $R_{61}$ to $R_{66}$ may be a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group.

For example, any two adjacent groups among $R_{51}$ to $R_{58}$ and $R_{61}$ to $R_{66}$ in Formulae 9 and 10 may optionally be linked to each other to form a ring, but embodiments of the present disclosure are not limited thereto.

The first compound represented by Formula 9 may be, for example, represented by Formula 9-1 below:

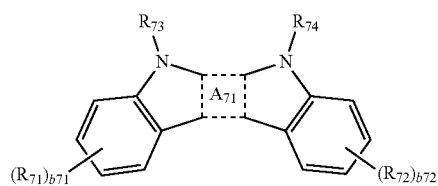

Formula 9-1

In Formula 9-1, ring $A_{71}$ may be a substituted or unsubstituted $C_6$-$C_{60}$ carbocyclic group or a substituted or unsubstituted $C_1$-$C_{60}$ heterocyclic group, $R_{71}$ to $R_{74}$ may each independently be hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and b71 and b72 may each independently be an integer from 0 to 4.

The first compound represented by Formula 9 may be, for example, represented by Formula 9-2 below:

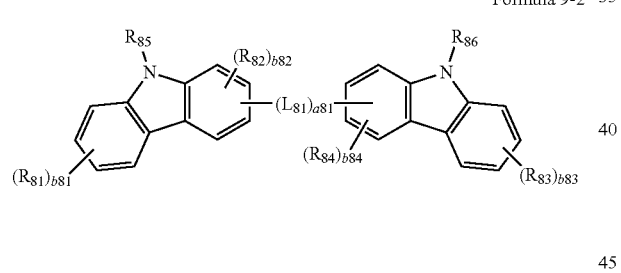

Formula 9-2

In Formula 9-2, $L_{81}$ may be a single bond, a substituted or unsubstituted $C_6$-$C_{60}$ aryl group, a substituted or unsubstituted $C_1$-$C_{60}$ heteroaryl group, a substituted or unsubstituted divalent non-aromatic condensed polycyclic group, or a substituted or unsubstituted divalent non-aromatic condensed heteropolycyclic group, a81 may be an integer from 1 to 5, $R_{81}$ to $R_{86}$ may each independently be hydrogen, deuterium, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, or a substituted or unsubstituted monovalent non-aromatic condensed heteropolycyclic group, b81 and b83 may each independently be an integer from 0 to 4, and b82 and b84 may each independently be an integer from 0 to 4.

For example, the first compound may be compounds represented by Formulae H1-1 to H1-13, H2-1 to H2-34, and H3-1 to H3-3 below:

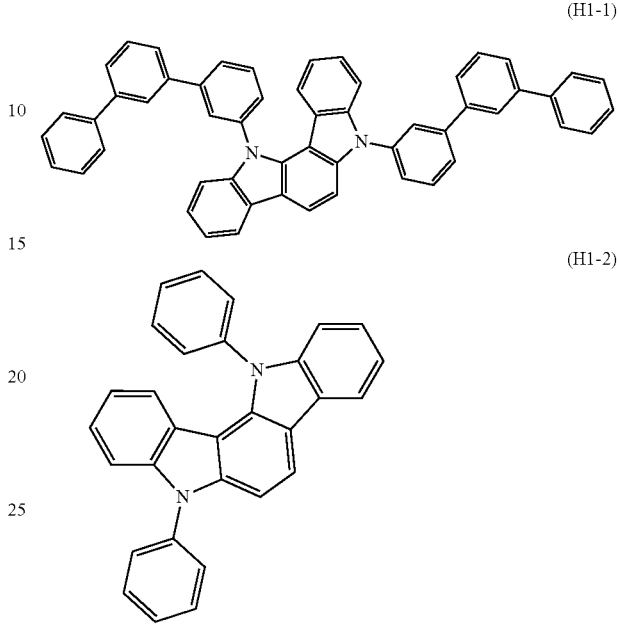

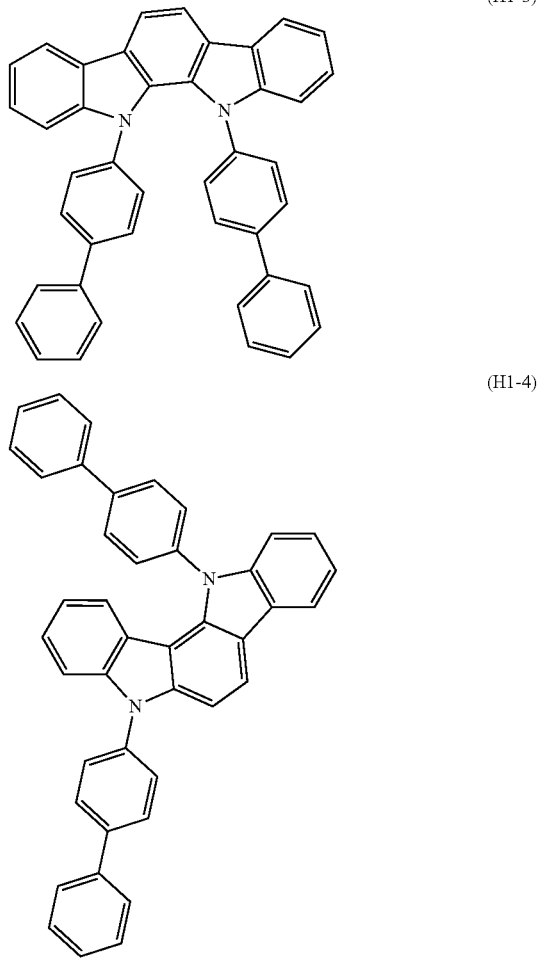

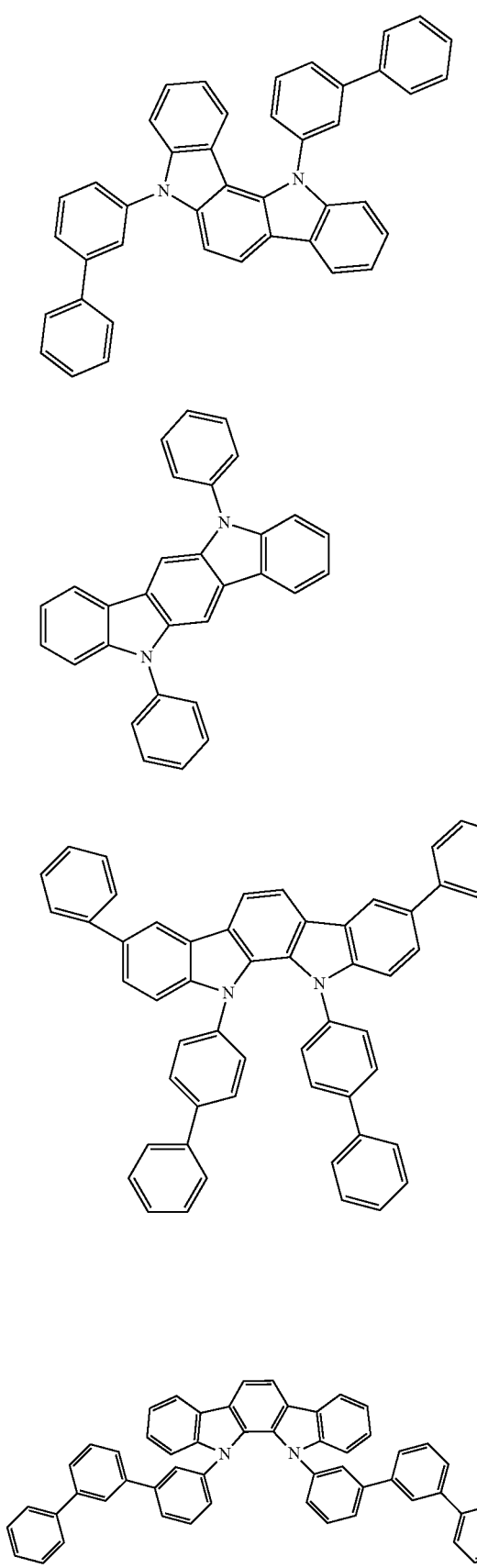

(H1-12)
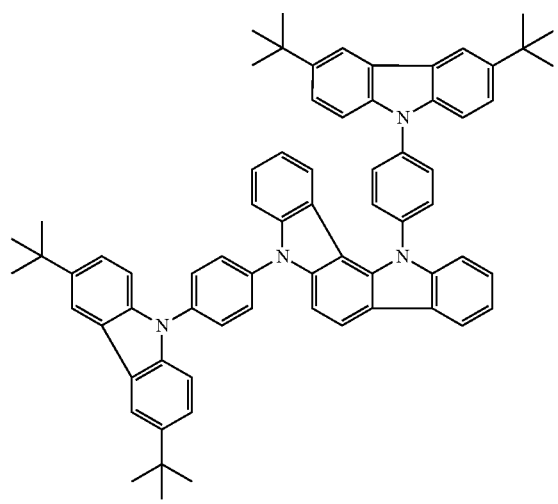
(H1-13)
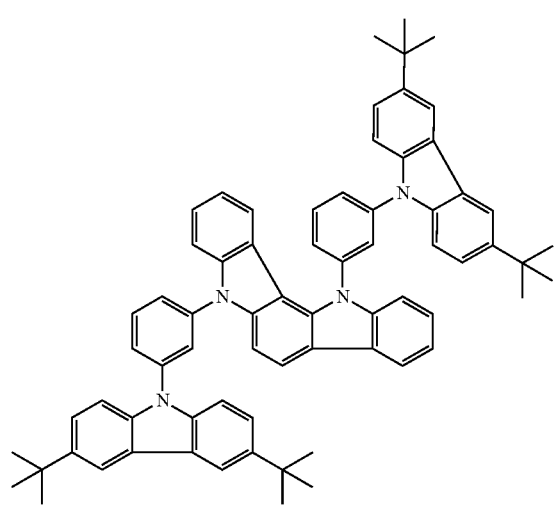
(H2-1)
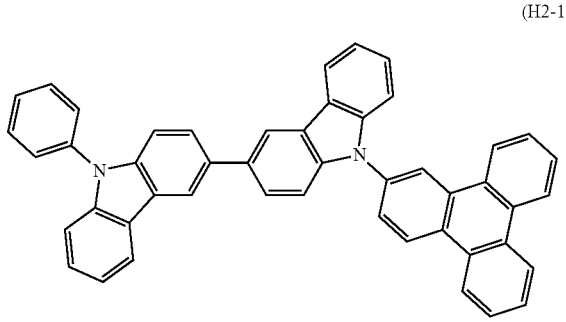
(H2-2)
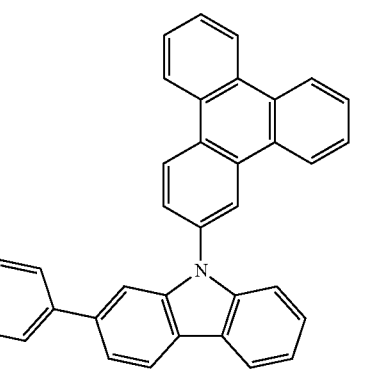
(H2-3)
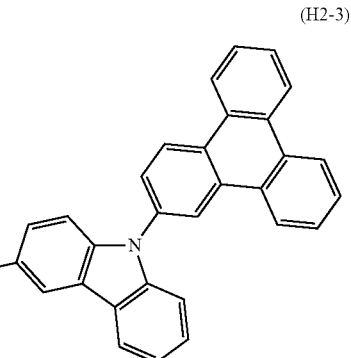
(H2-4)
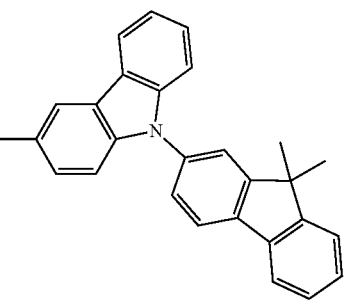
(H2-5)
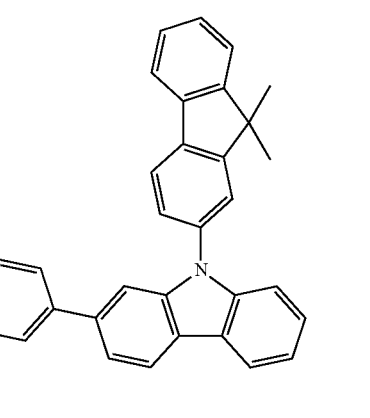

(H2-6)
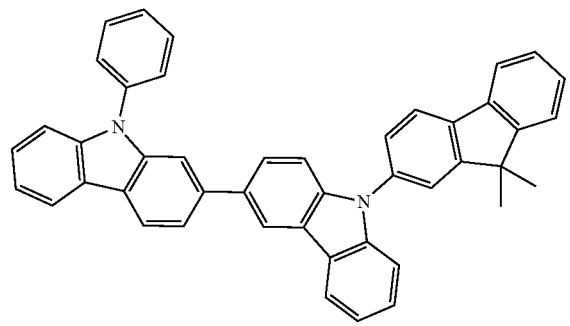
(H2-7)
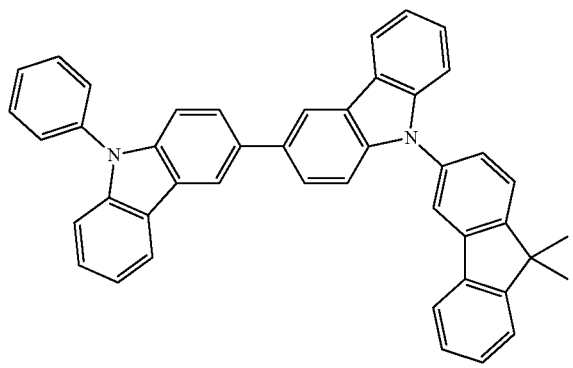
(H2-8)
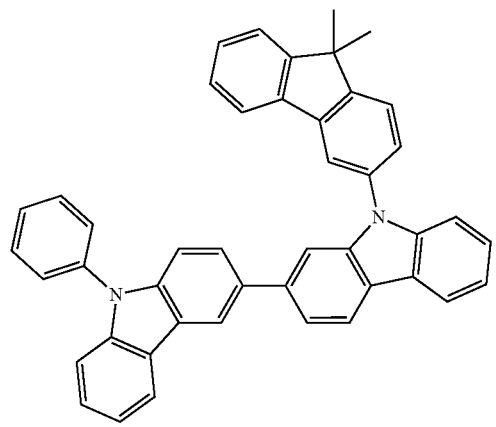
(H2-9)
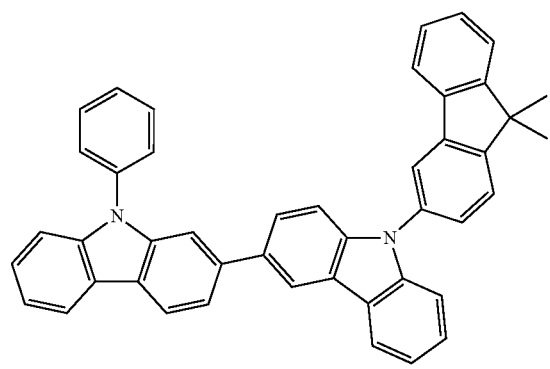
(H2-10)
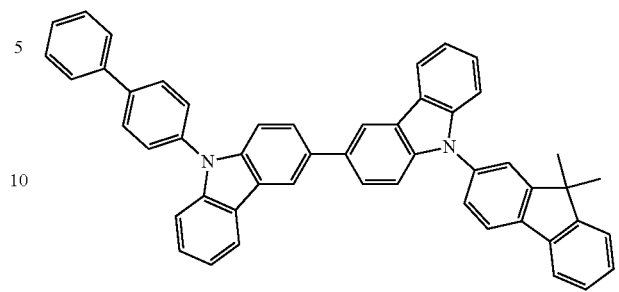
(H2-11)
(H2-12)
(H2-13)
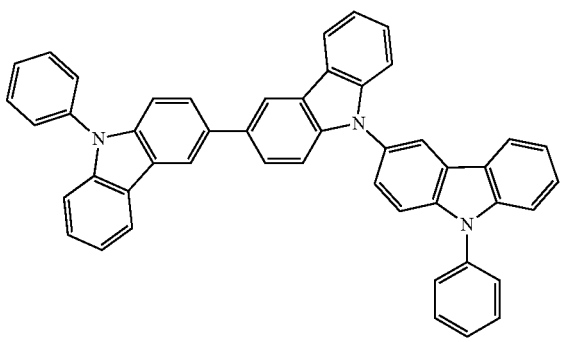

(H2-14)
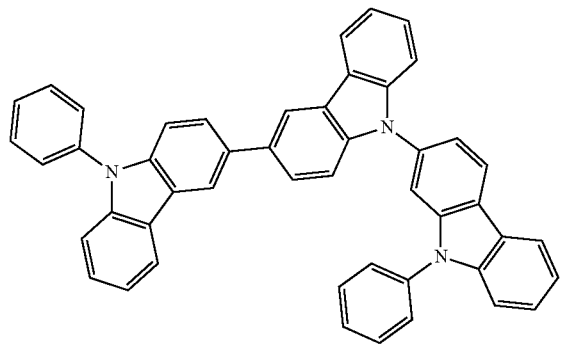
(H2-13)
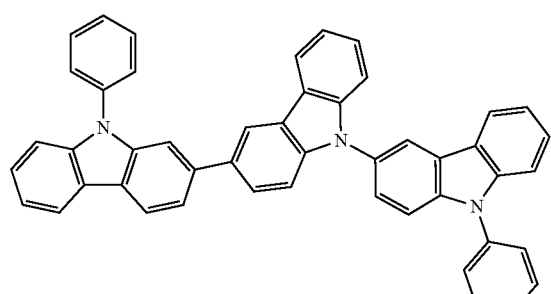
(H2-15)
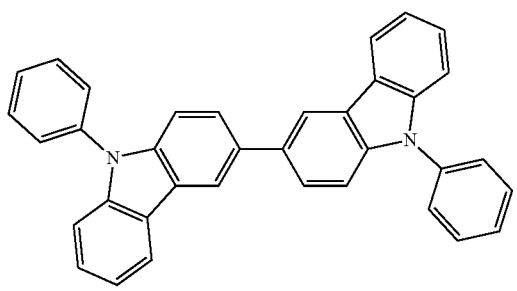
(H2-16)
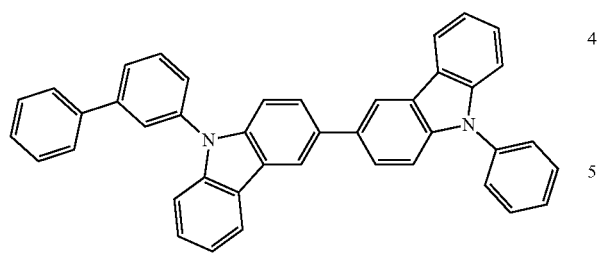
(H2-17)
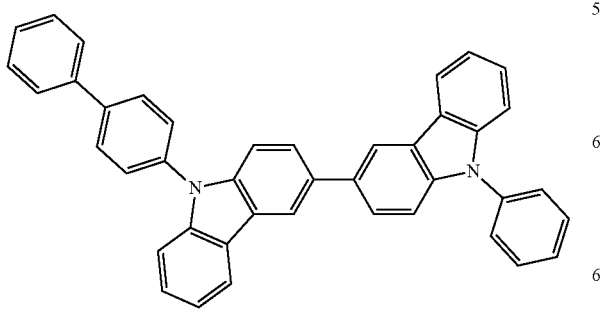
(H2-18)
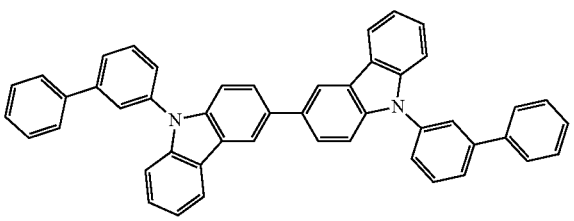
(H2-19)
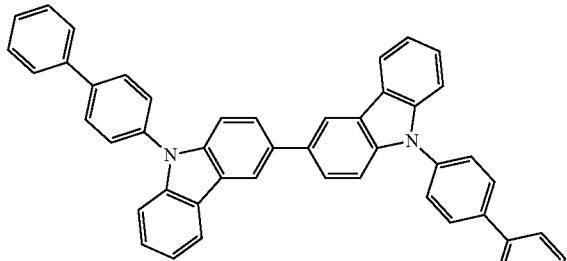
(H2-20)
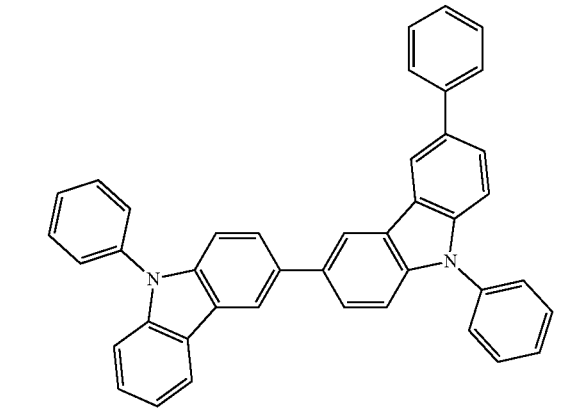
(H2-21)
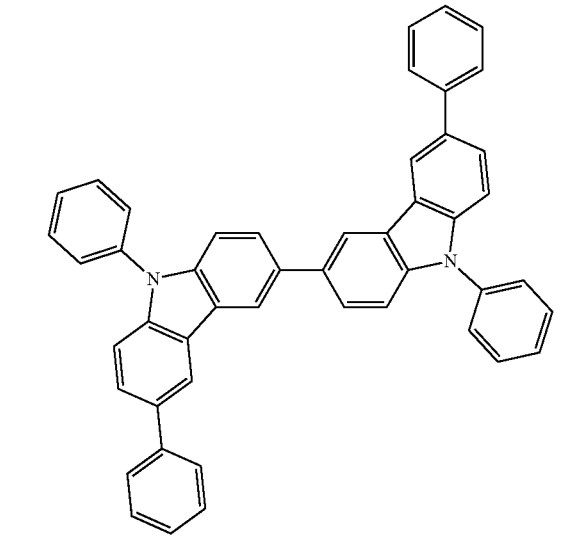

(H2-22)
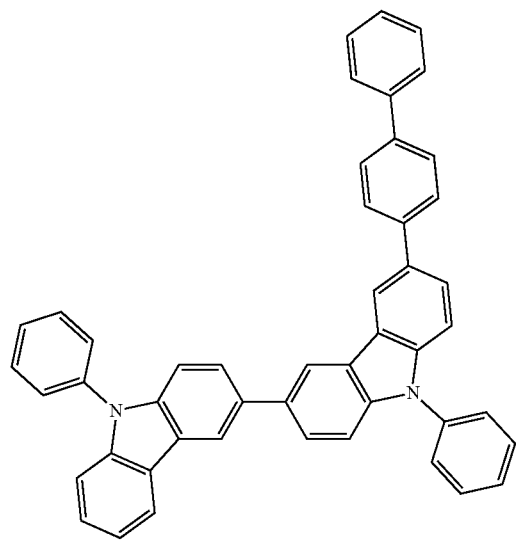
(H2-23)
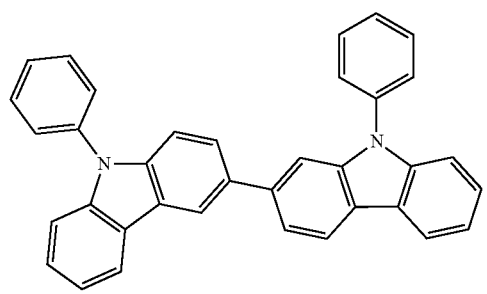
(H2-24)
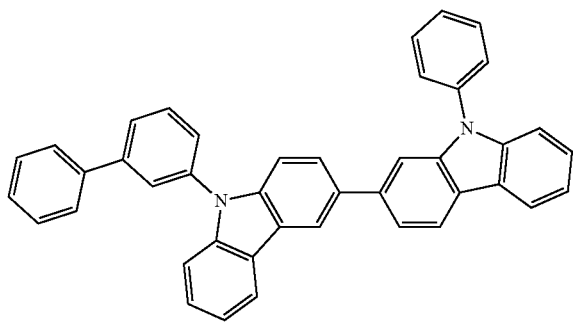
(H2-25)
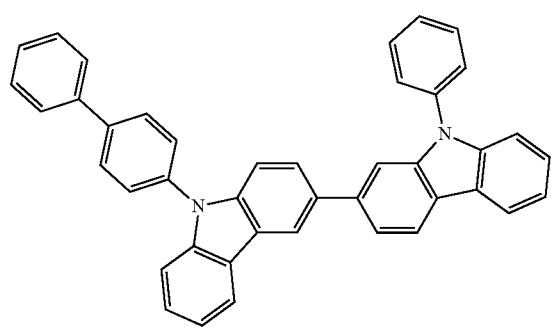
(H2-26)
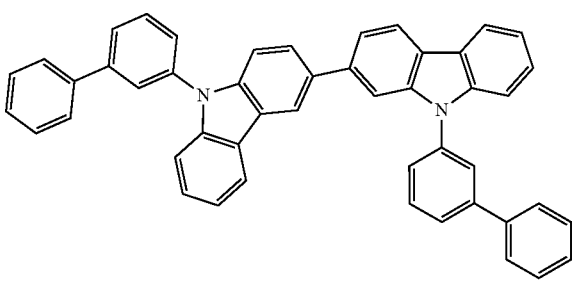
(H2-27)
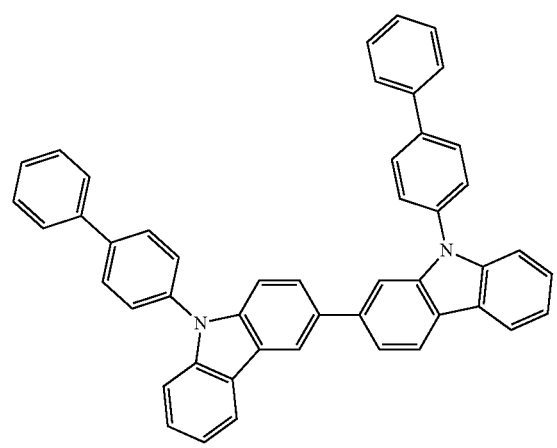
(H2-28)
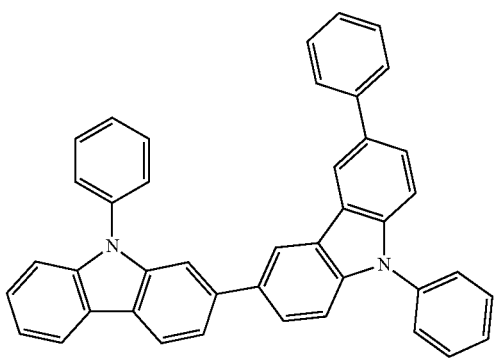
(H2-29)
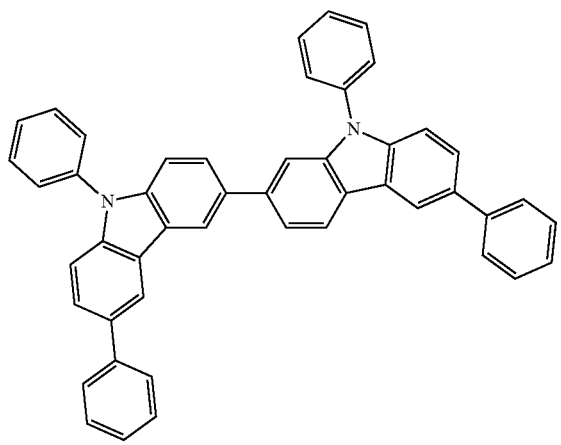

(H2-30)
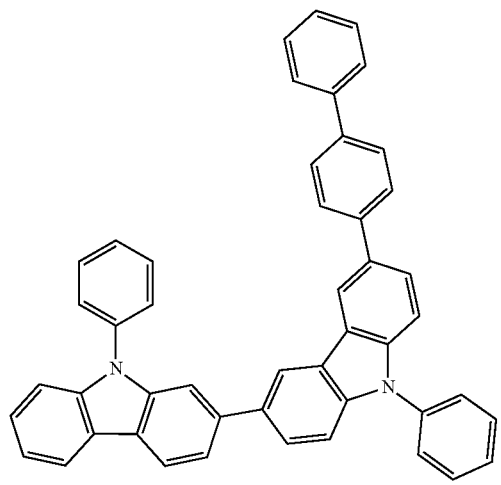
(H2-31)
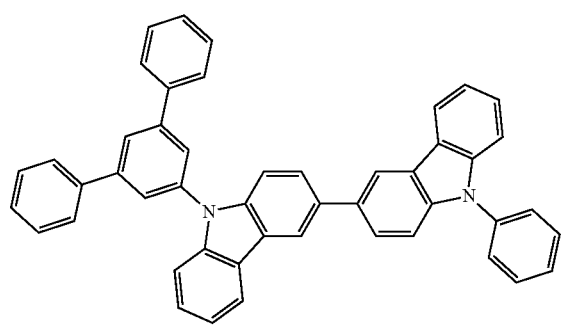
(H2-32)
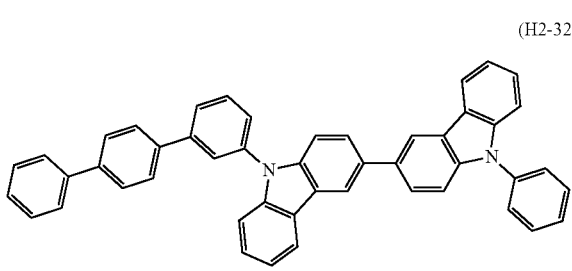
(H2-33)
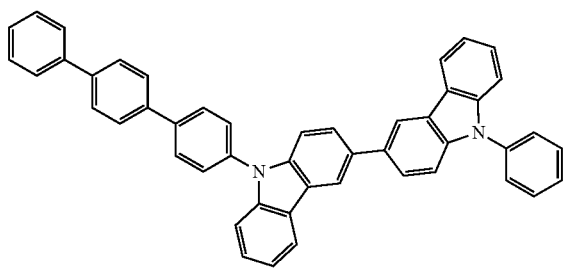
(H2-34)
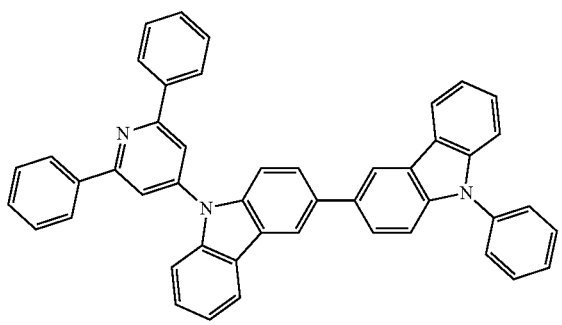
(H2-35)
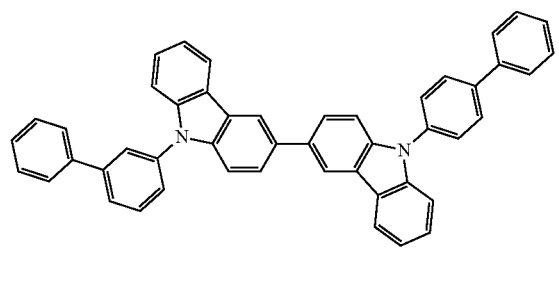
(H3-1)
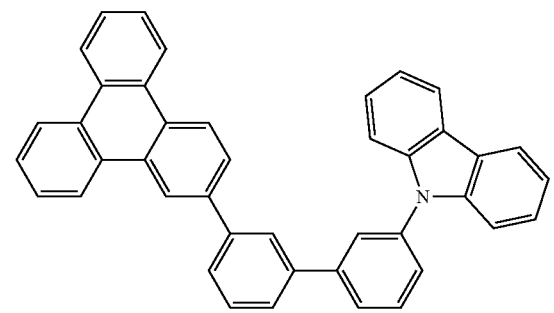
(H3-2)
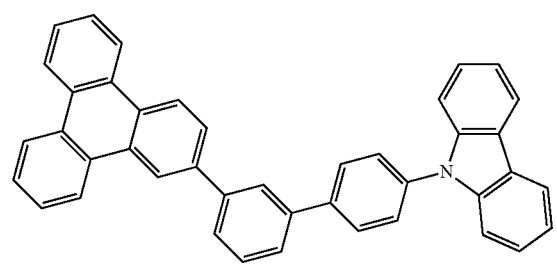

-continued (H3-3)

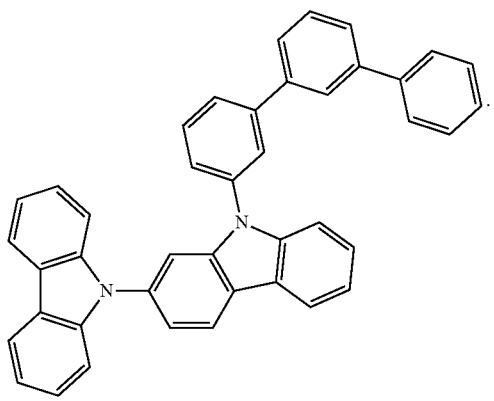

The first compound including a carbazole-based moiety other than the compound represented by Formula 9 is not limited to the above-described example compounds. For example, the first compound may be known carbazole derivatives disclosed in paragraphs [0095] to [0104] of US Patent Publication No. US2016/0093808, Japanese Patent Laid-Open Publication No. 2014-509067 and the like may be used in the present disclosure, and are each herein incorporated by reference. The carbazole derivatives described in these references may also be used as a ground for corrections herein.

For example, the second compound may be a compound represented by Formulae Az1 to Az38 below:

Az1

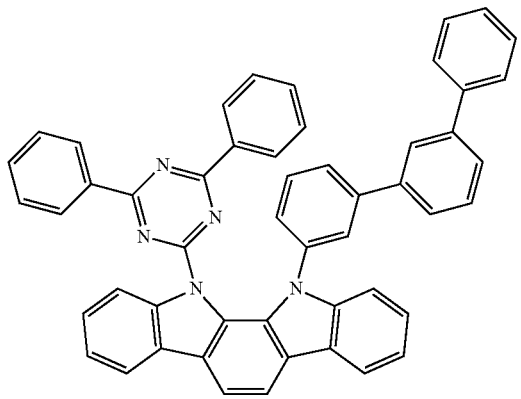

Az2

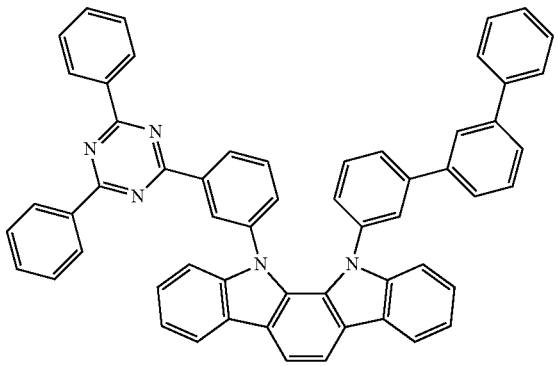

Az3

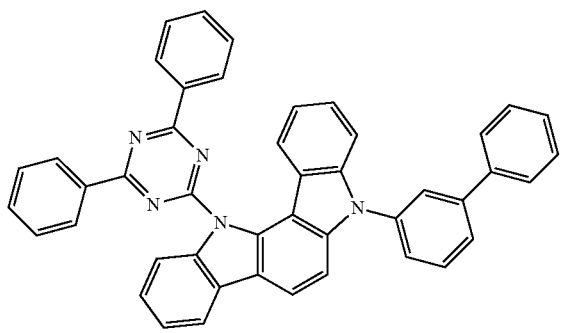

Az4

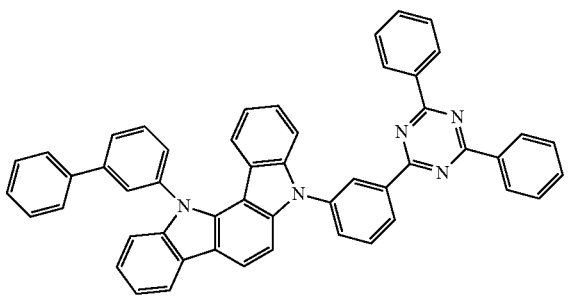

-continued
Az5
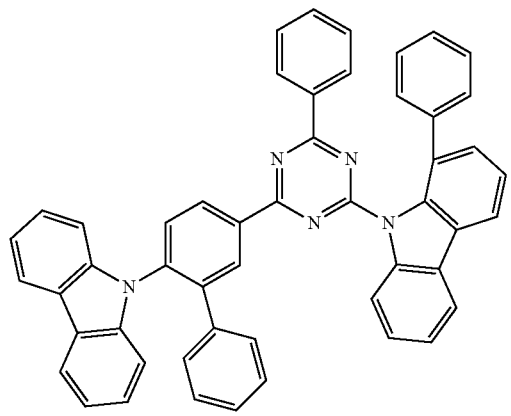
Az6
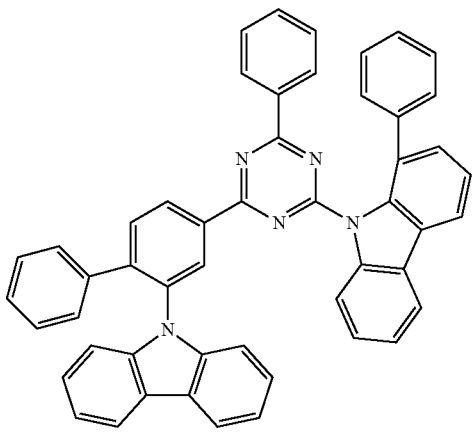
Az7
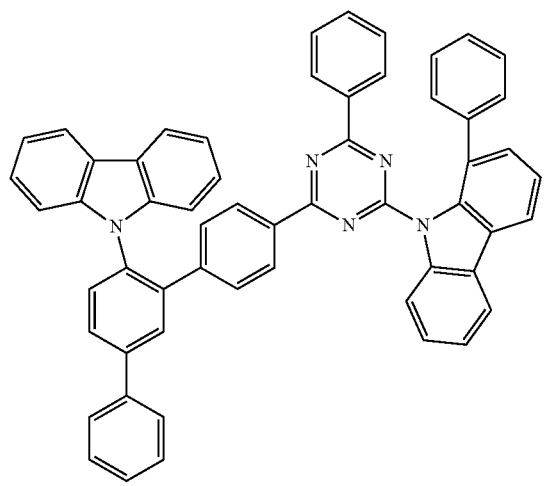
Az8
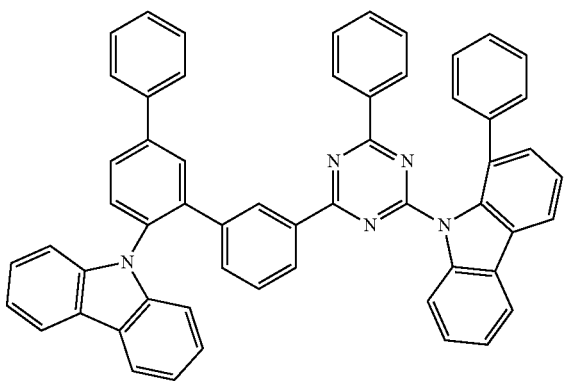
Az9
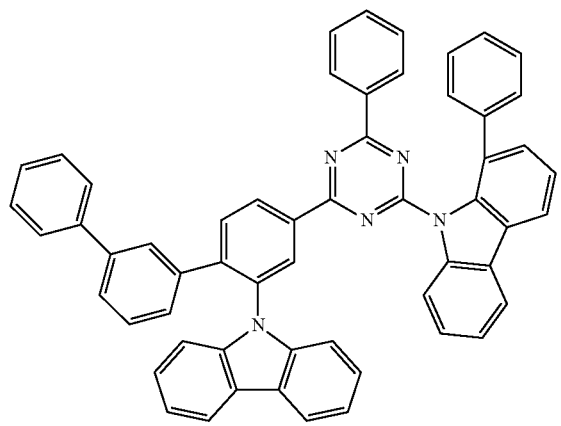
Az10
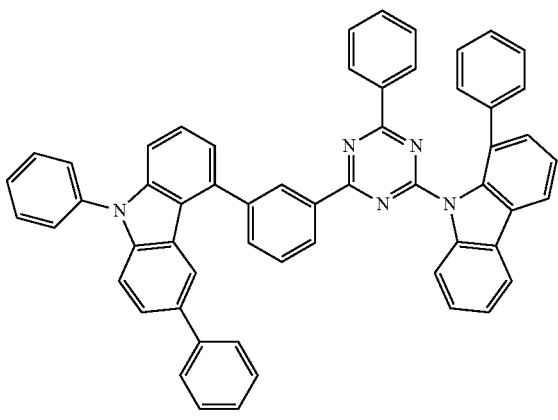

-continued
Az11
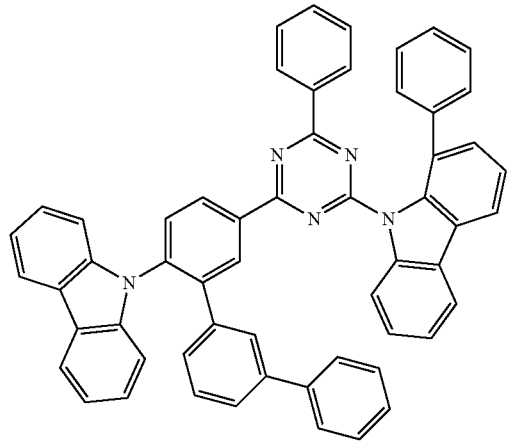
Az12
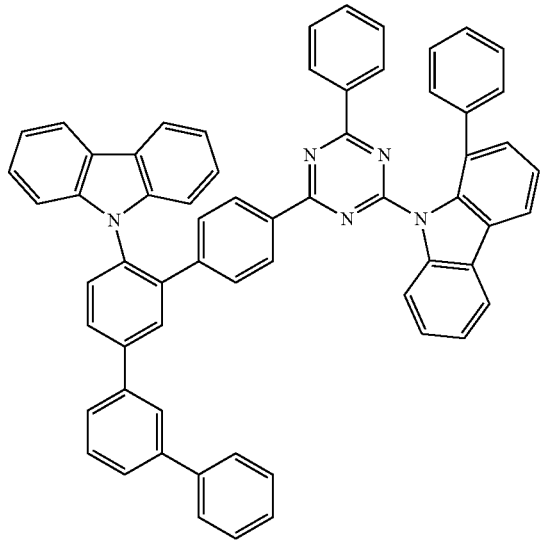
Az13
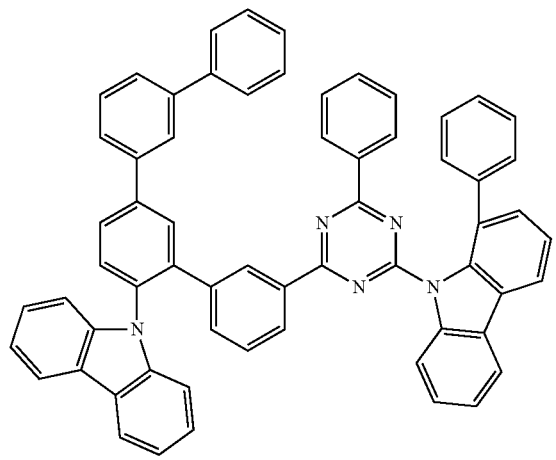
Az14
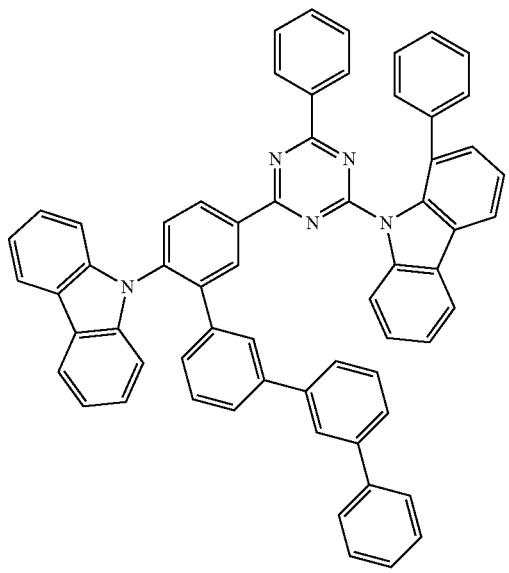
Az15
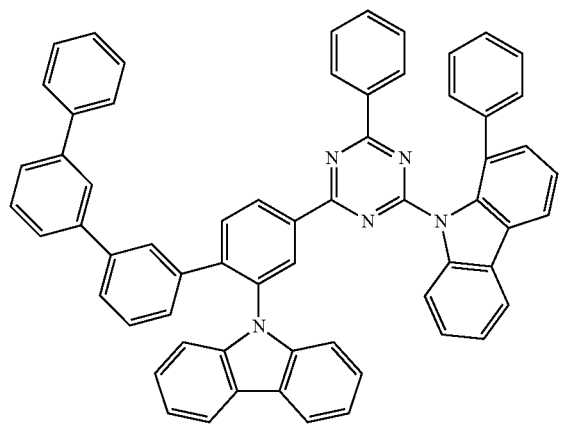
Az16
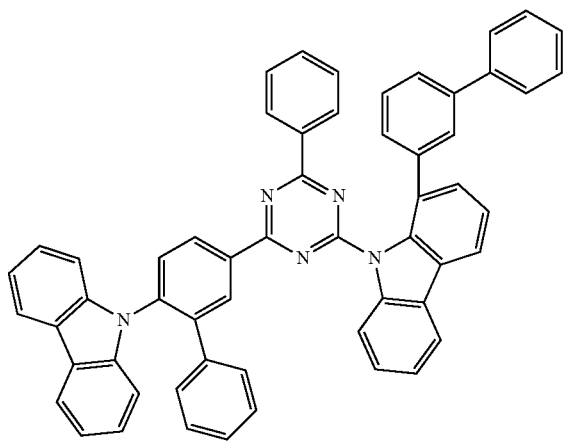

-continued
Az17
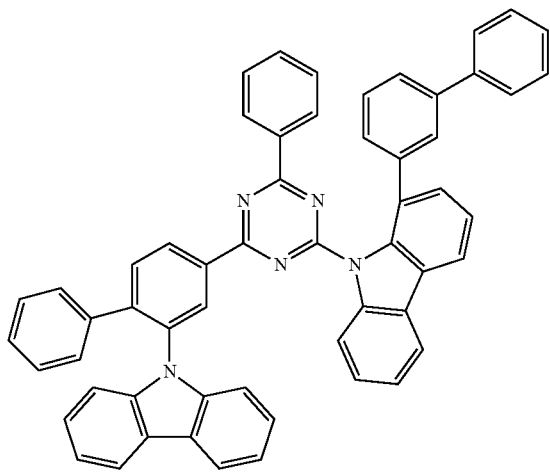
Az18
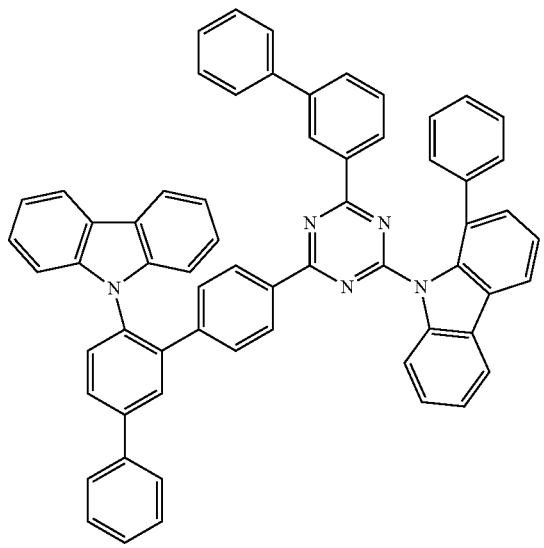
Az19
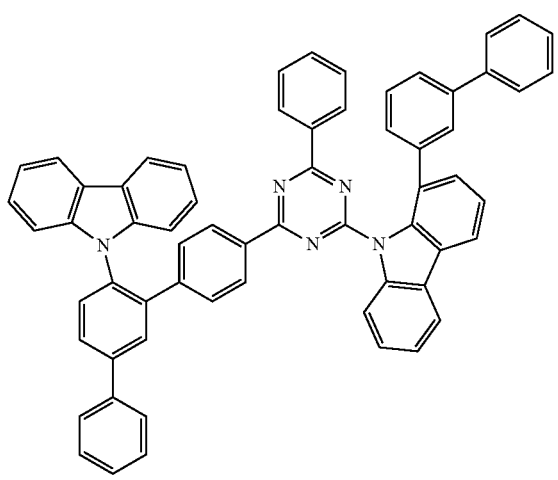
Az20
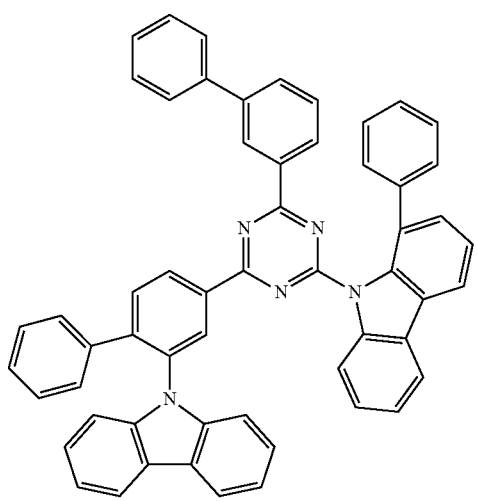
Az21
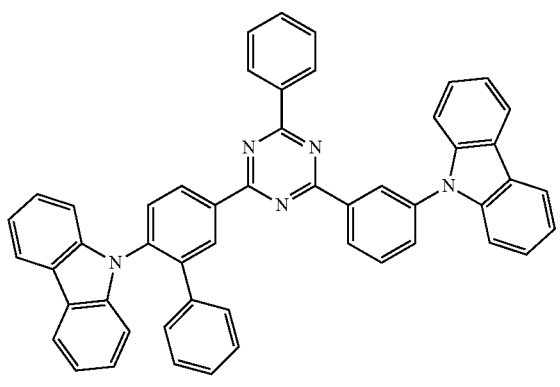
Az22
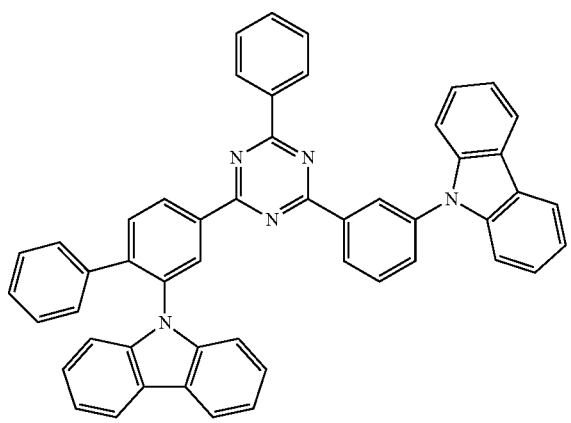

-continued
Az23
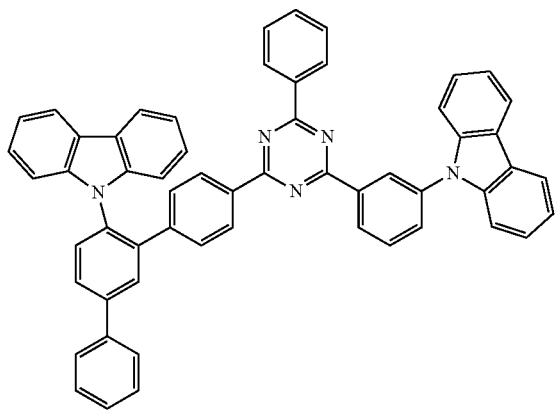
Az24
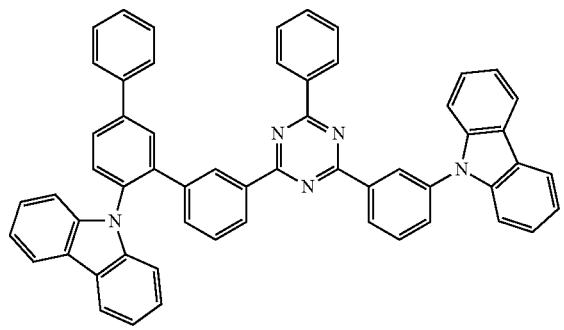
Az25
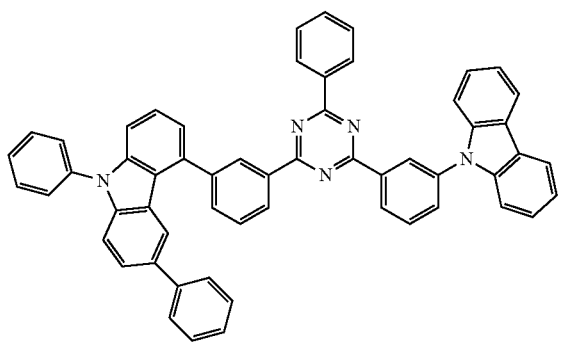
Az26
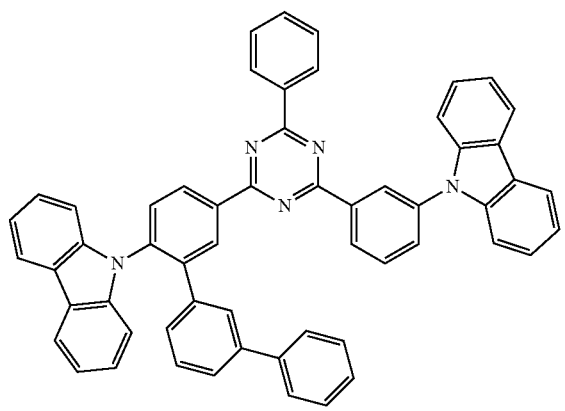
Az27
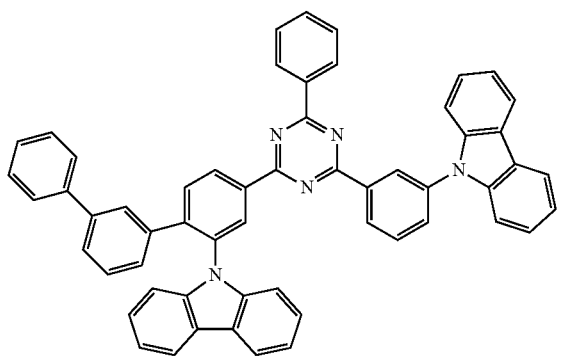
Az28
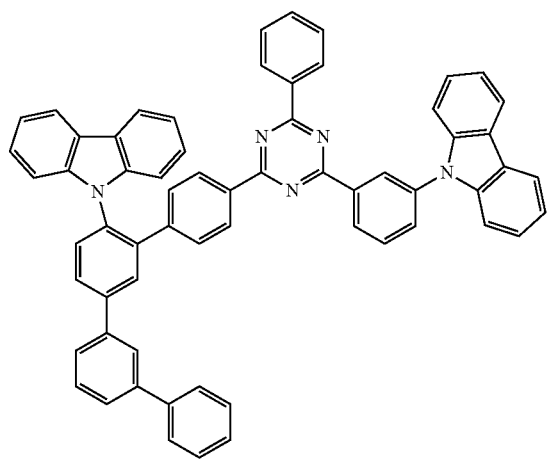

-continued
Az29
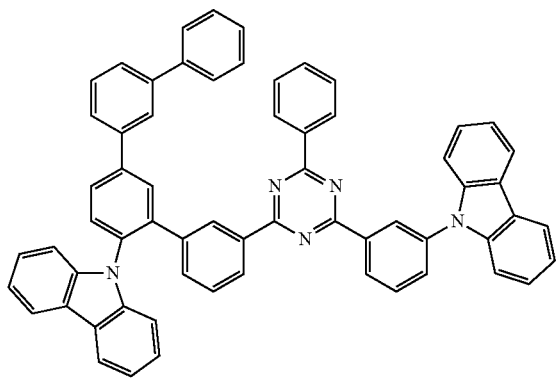
Az30
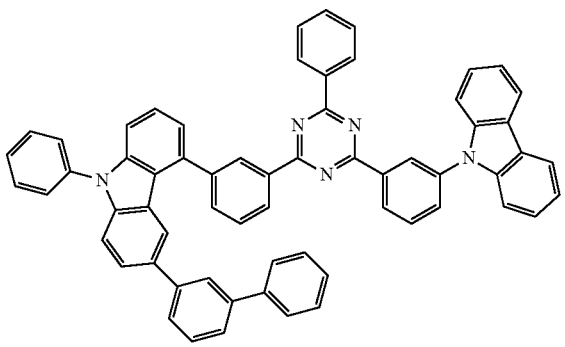
Az31
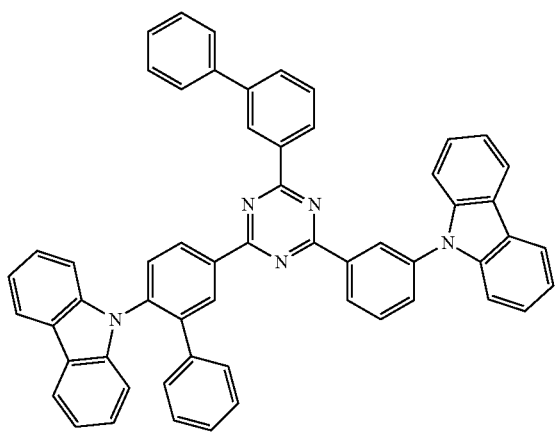
Az32
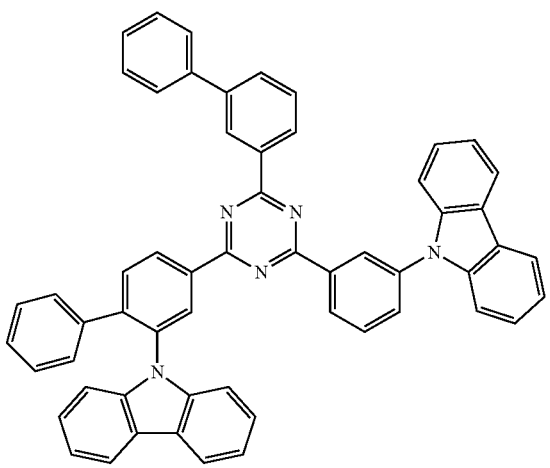
Az33
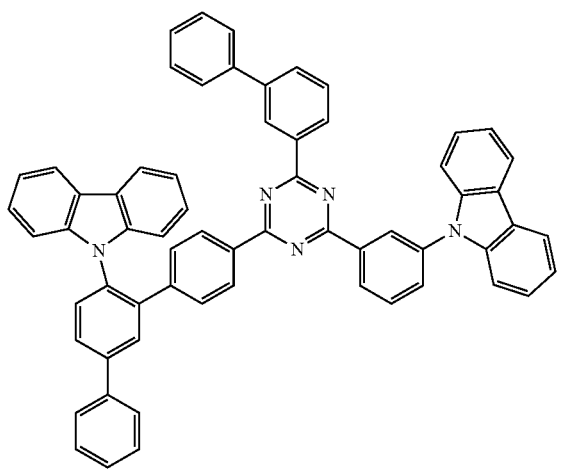
Az34
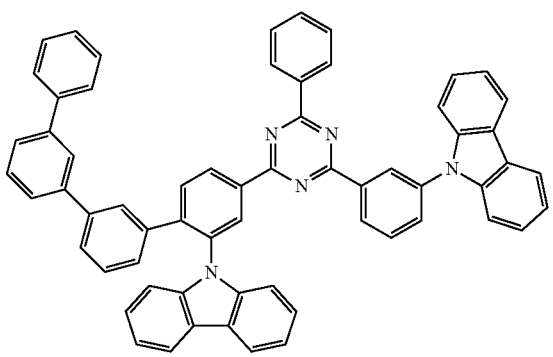

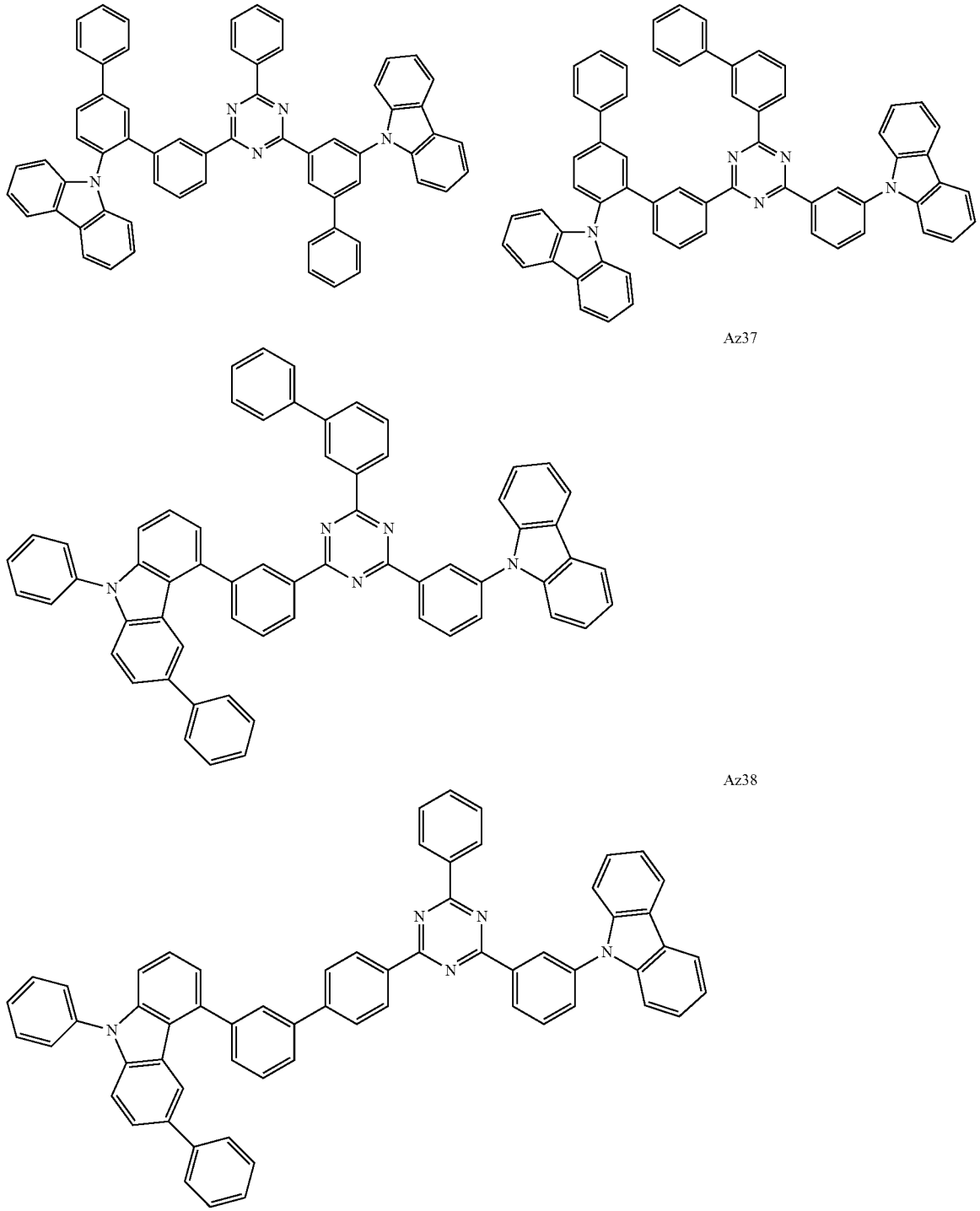

The first compound may have the lowest HOMO level, except for the luminescent material (dopant) among the compounds contained in the composition. Therefore, the first compound has a high hole injection capability and/or a high hole transport capability.

Accordingly, by adjusting the ratio of the first compound in the composition, the hole injection capability and/or hole transport capability of the composition may be controllable. Thus, the amount of holes in an emission layer of an organic light-emitting device including the composition and a hole density profile in the thickness direction of the emission layer may be easily controlled.

When the composition further includes the first compound, the difference ($\Delta$HOMO) (hole trap depth) between the HOMO level ($HOMO_0$) of the compound of the condensed cyclic compound represented by Formula 1 and the HOMO level ($HOMO_{Cz}$) of the first compound may be obtained from Equation 1. Herein, $HOMO_0$ and $HOMO_{Cz}$ are both negative.

$$\Delta HOMO = HOMO_{Cz} - HOMO_0 \quad \text{Equation 1}$$

ΔHOMO may be, for example, about 0.05 eV to about 1.0 eV, for example, about 0.10 eV to about 0.8 eV, or, for example, about 0.15 eV to about 0.7 eV.

FIG. 1 shows a diagram illustrating an exemplary energy level relationship between a condensed cyclic compound represented by Formula 1 and a first compound including a carbazole group in a composition according to an embodiment. Referring to FIG. 1, it can be seen the relationship between $HOMO_0$ and $HOMO_{Cz}$. Within this range, the luminescent efficiency and light-emission lifespan of the organic light-emitting device are further improved.

The second compound has the deepest LUMO level among the compounds contained in the composition. Therefore, the second compound has a high electron injection capability and/or a high electron transport capability.

Accordingly, by adjusting the ratio of the second compound in the composition, the electron injection capability and/or electron transport capability of the composition may be controllable. Thus, the amount of electrons in an emission layer of an organic light-emitting device including the composition and an electron density profile in the thickness direction of the emission layer may be easily controlled.

When the composition further includes the second compound, the difference (ΔLUMO) (electron trap depth) between the LUMO level ($LUMO_0$) of the condensed cyclic compound represented by Formula 1 and the LUMO level ($LUMO_{Azine}$) of the second compound may obtained from Equation 2. Herein, $LUMO_0$ and $LUMO_{Azine}$ are both negative.

$$\Delta LUMO = LUMO_0 - LUMO_{Azine} \quad \text{Equation 2}$$

ΔLUMO may be, for example, about 0.05 eV to about 1.0 eV, for example, about 0.05 eV to about 0.5 eV, or, for example, about 0.05 eV to about 0.3 eV.

Figure 2:
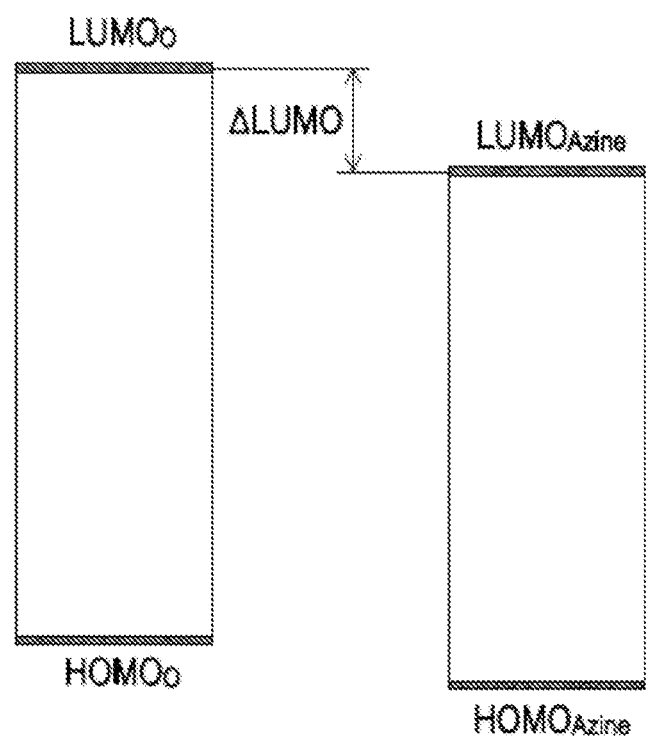
FIG. 2 shows a diagram illustrating an exemplary energy level relationship between a condensed cyclic compound represented by Formula 1 and a second compound including an azine group in a composition according to an embodiment.

FIG. 2 shows a diagram illustrating an exemplary energy level relationship between a condensed cyclic compound represented by Formula 1 and a second compound including an azine group in a composition according to an embodiment. Referring to FIG. 2, it can be seen the preferred relationship between $LUMO_0$ and $LUMO_{Azine}$. Within this range, the luminescent efficiency and light-emission lifespan of the organic light-emitting device are further improved.

When the composition includes the condensed cyclic compound and the first compound, the composition may be excellent in terms of the hole injection capability and/or the hole transport capability, and the composition may be used in a hole injection layer, hole transport layer and/or emission layer of an organic light-emitting device.

When the composition includes the condensed cyclic compound and the second compound, the composition may be excellent in terms of the electron injection capability and/or the electron transport capability, and the composition may be used in an electron injection layer, electron transport layer and/or emission layer of an organic light-emitting device.

When the composition includes the condensed cyclic compound, the first compound, and the second compound, the composition may be excellent in terms of the hole injection capability, the hole transport capability, the electron injection capability and/or the electron transport capability, and the composition may be used in a hole injection layer, hole transport layer, electron injection layer, electron transport layer and/or emission layer of an organic light-emitting device.

In one or more embodiments, the composition may include the first compound and the second compound, but embodiments of the present disclosure are not limited. When the composition includes the first compound and the second compound together, the control of the hole and the control of the electron may be performed independently. Therefore, a high level of process convenience may be provided in the process of optimizing the performance of the organic light-emitting device using such a composition.

The condensed cyclic compound represented by Formula 1 in the composition may be a wide band gap host. Therefore, the luminescent efficiency and light-emission lifespan of the organic light-emitting device may be further improved.

The composition may further include a luminescent material.

The luminescent material is not particularly limited as long as it has a luminescent function, and may be a fluorescent dopant, a phosphorescent dopant, a quantum dot, or the like.

The fluorescent dopant may be a compound capable of emitting light from a singlet exciton, and examples thereof include a perylene or a derivative thereof, a rubrene or a derivative thereof, a coumarin or a derivative thereof, and a 4-dicyanomethylene-2-(p-dimethylaminostyryl)-6-methyl-4H-pyran (DCM) or a derivative thereof, but embodiments of the present disclosure are not limited thereto.

The phosphorescent dopant may be compound capable of emitting light from a triplet exciton, and may be an organometallic compound. For example, phosphorescent dopant may be an iridium complex, such as bis[2-(4,6-difluorophenyl)pyridinate] picolinate iridium (III) (Flrpic), bis(1-phenylisoquinoline)(acetylacetonate) iridium (III) ($Ir(piq)_2$(acac)), tris(2-phenylpyridine) iridium (Ill) ($Ir(ppy)_3$), tris (2-(3-p-xylyl)phenyl)pyridine iridium (Ill) (dopant), or the like, an osmium complex, or a platinum complex, but embodiments of the present disclosure are not limited thereto.

For example, the phosphorescent dopant may be a phosphorescent platinum group metallic complex. The platinum group metal is referred as a generic term of ruthenium (Ru), rhodium (Rh), palladium (Pd), osmium (Os), iridium (Ir), and platinum (Pt). In particular, a phosphorescent iridium (Ir) complex and a phosphorescent platinum (Pt) complex are more preferable.

For example, the phosphorescent dopant may include one or more ligand groups represented by Formulae $L_1$ to $L_{17}$ below:

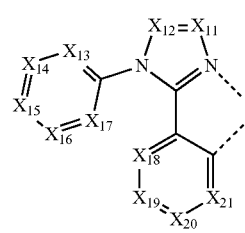

$L_1$

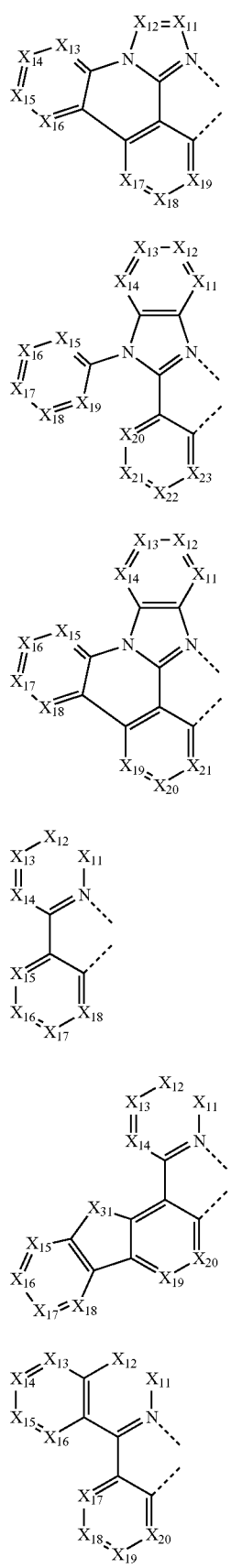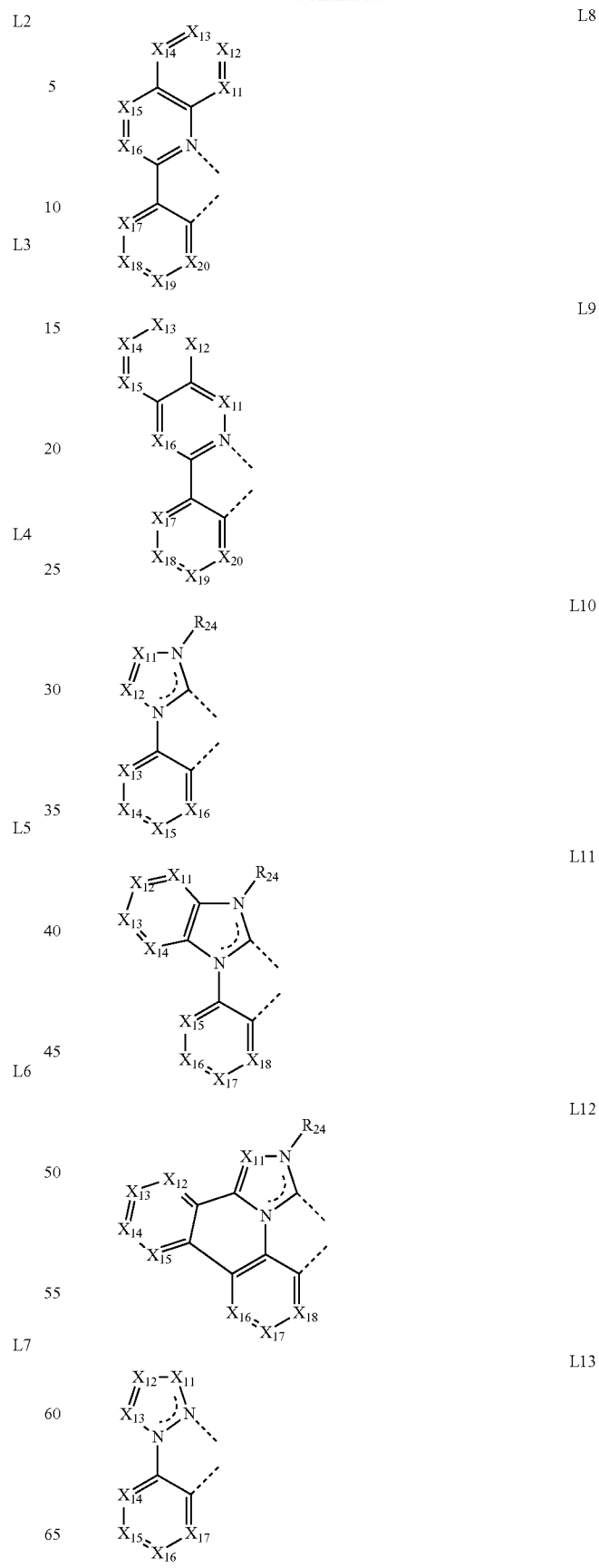

-continued

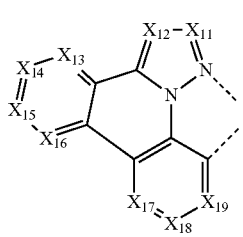
L14

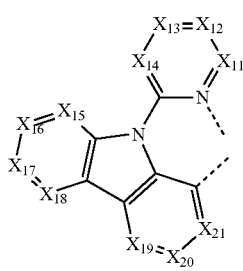
L15

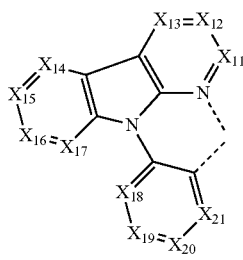
L16

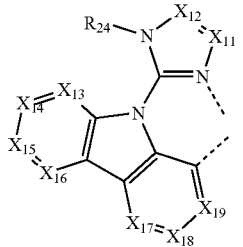
L17

In Formulae $L_1$ to $L_{17}$,
$X_{11}$ to $X_{23}$ may each independently be $C(R_{21})$ or Y,
$X_{31}$ may be $B(R_{22})$, $Y(R_{22})$, $P(R_{22})$, O, S, Se, C=O, S=O, $SO_2$, $C(R_{22})(R_{23})$, $Si(R_{22})(R_{23})$, or $Ge(R_{22})(R_{23})$,
$R_{21}$ to $R_{24}$ may each independently be hydrogen, deuterium, halogen, a substituted or unsubstituted $C_1$-$C_{60}$ alkyl group, a substituted or unsubstituted $C_3$-$C_{60}$ cycloalkyl group, a substituted or unsubstituted $C_1$-$C_{60}$ heteroalkyl group, a substituted or unsubstituted $C_7$-$C_{60}$ aryl alkyl group, a substituted or unsubstituted $C_1$-$C_{60}$ alkoxy group, a substituted or unsubstituted $C_6$-$C_{60}$ aryloxy group, an amino group, a silyl group, a substituted or unsubstituted $C_2$-$C_{60}$ alkenyl group, a substituted or unsubstituted $C_3$-$C_{60}$ cycloalkenyl group, a substituted or unsubstituted $C_2$-$C_{60}$ heteroalkenyl group, a substituted or unsubstituted $C_2$-$C_{60}$ alkynyl group, a substituted or unsubstituted $C_6$-$C_{60}$ aryl group, a substituted or unsubstituted $C_1$-$C_{60}$ heteroaryl group, an acyl group, a carbonyl group, a carboxylic acid group, an ester group, a nitrite group, an isonitrile group, a sulfonyl group, a sulfinyl group, or a phosphine group, and any two adjacent groups among $R_{21}$ to $R_{24}$ may be condensed or combined to each other to form a ring.

For example, the phosphorescent dopant may be of Compounds D1 to D143 below:

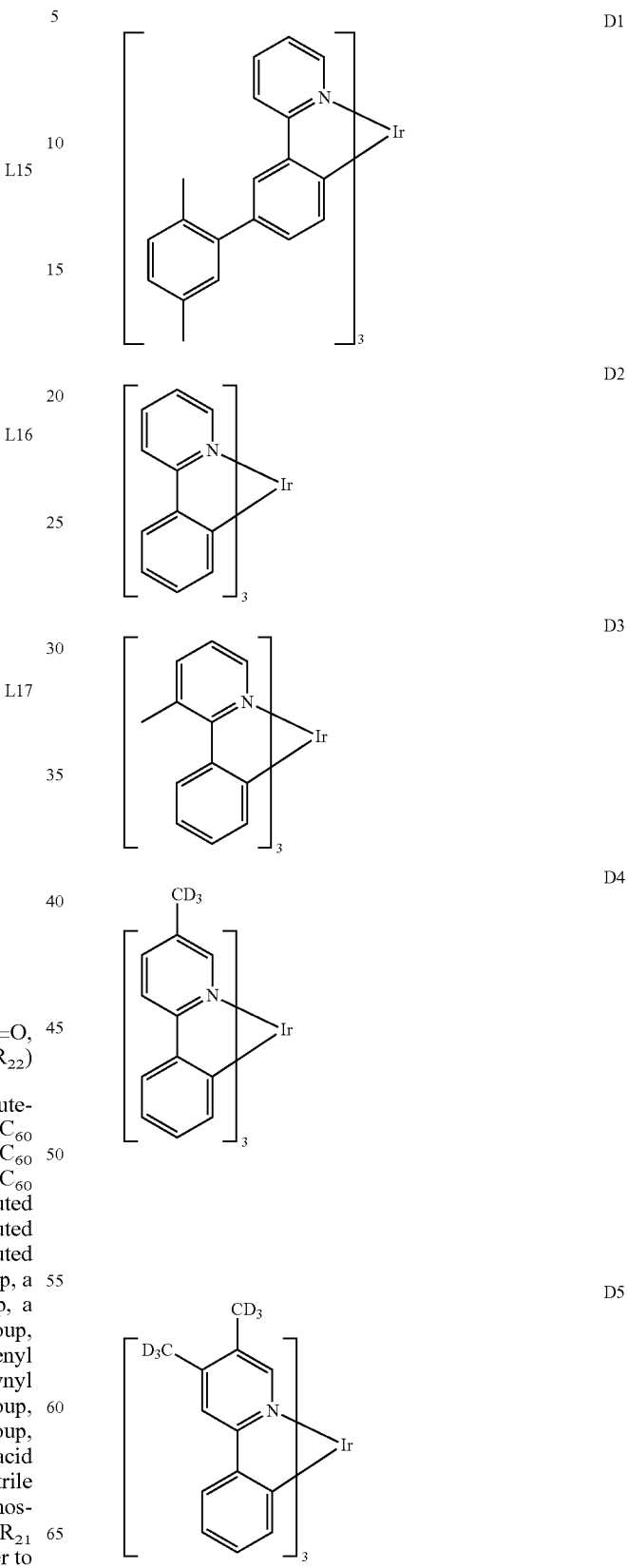

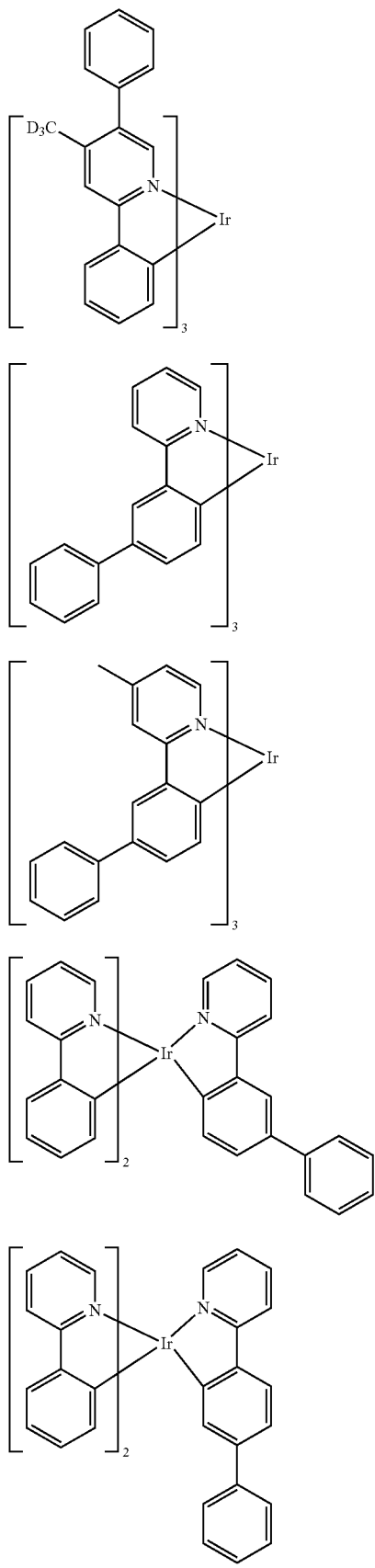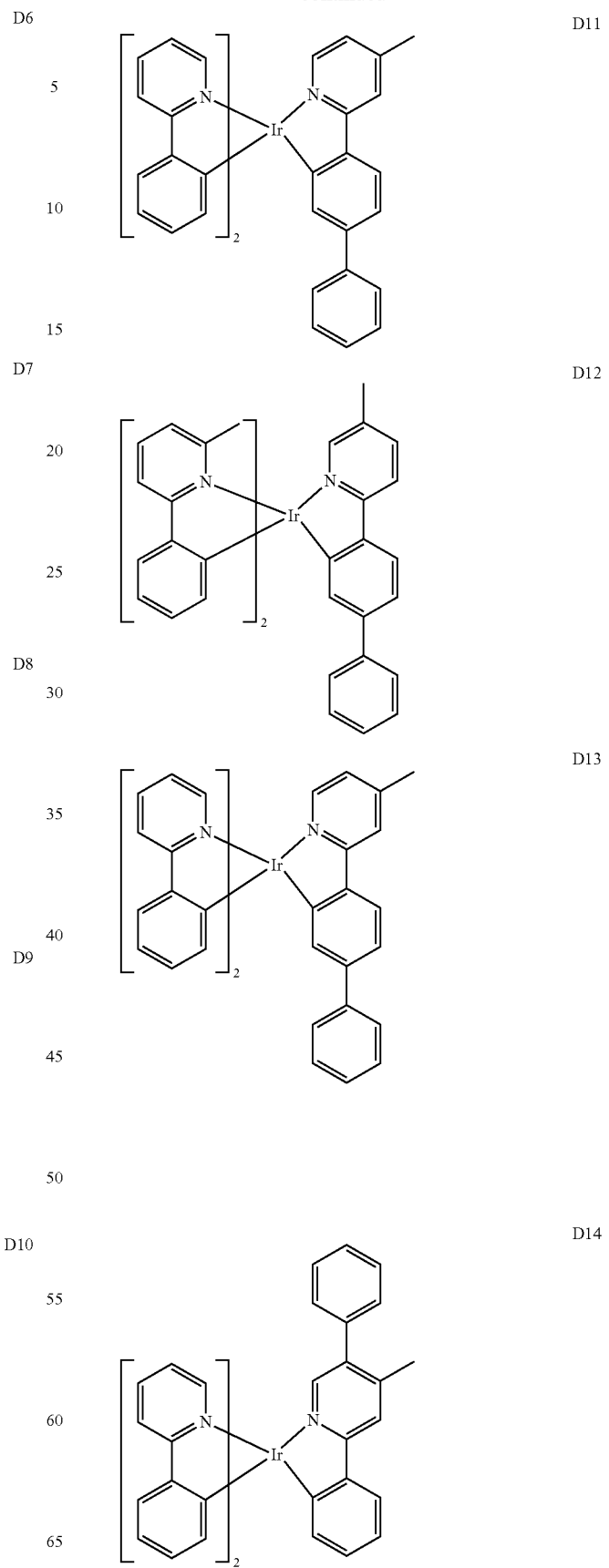

D15 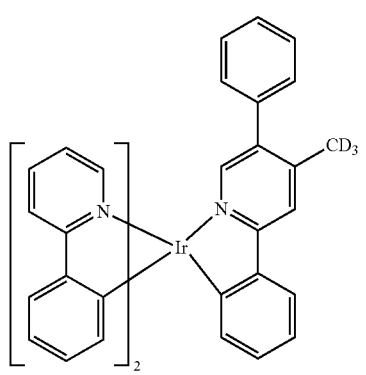
D16 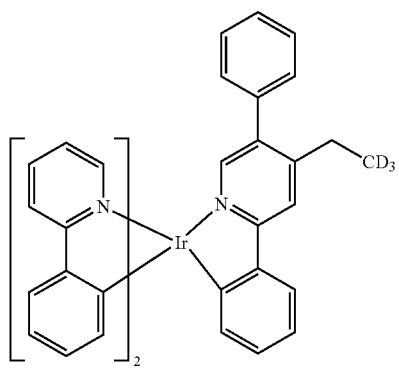
D17 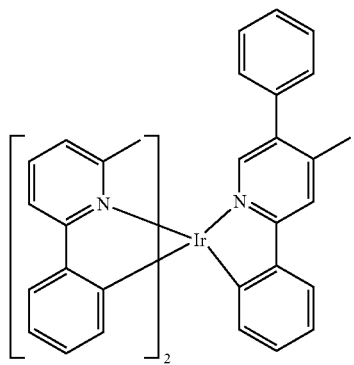
D18 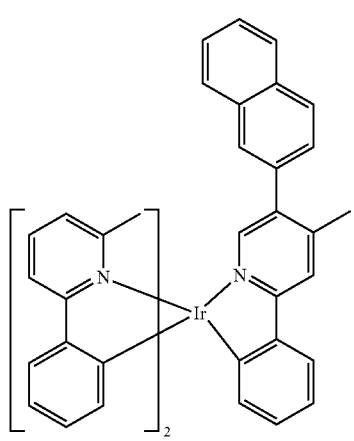
D19 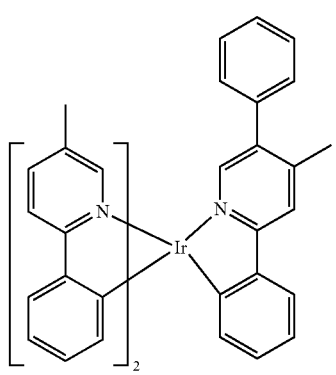
D20 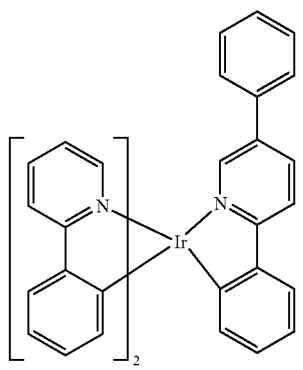
D21 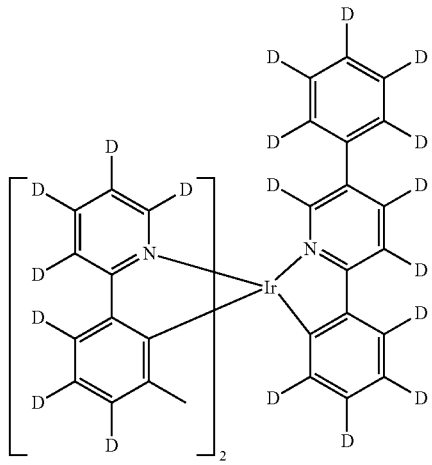
D22 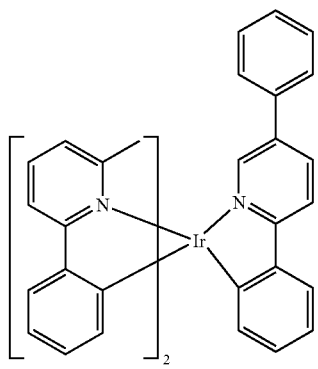

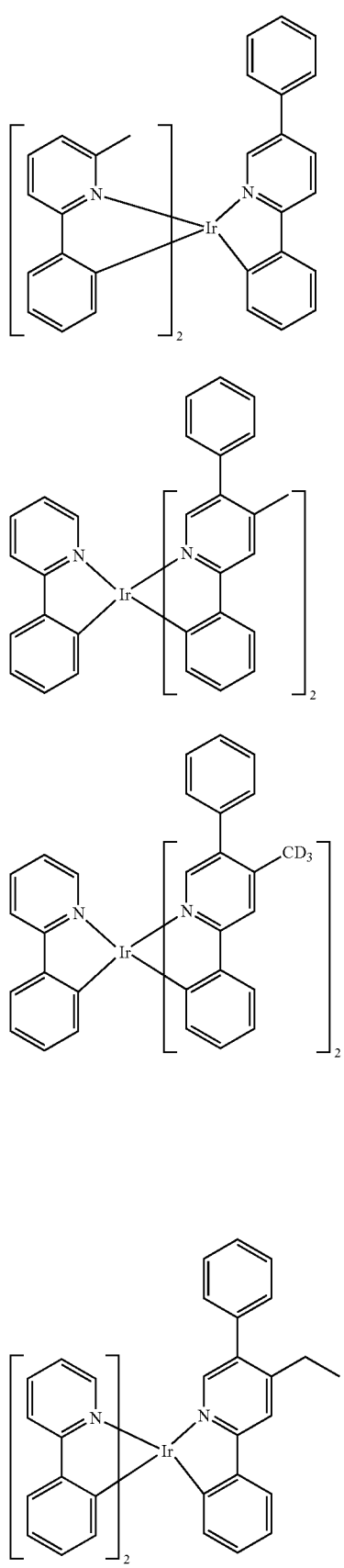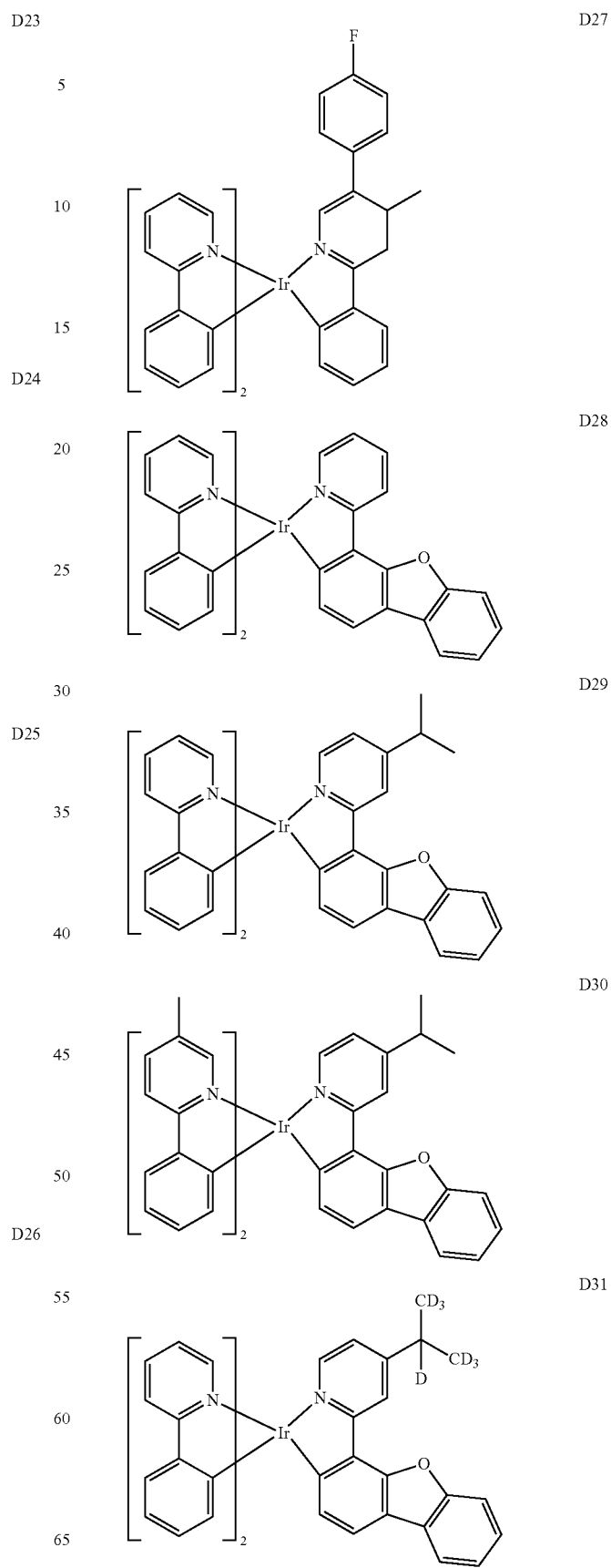

D32 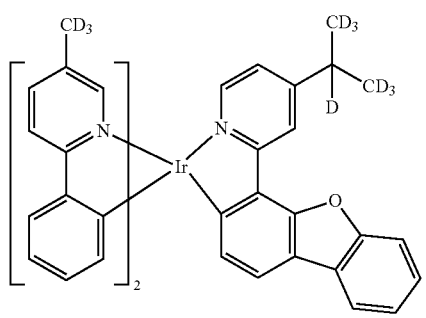
D33 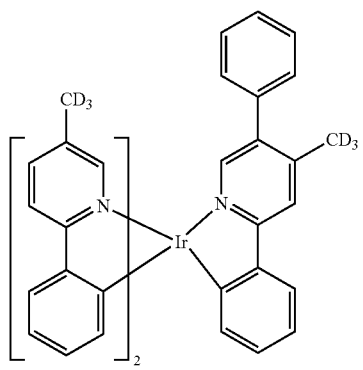
D34 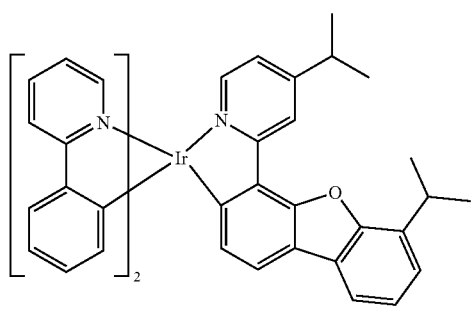
D35 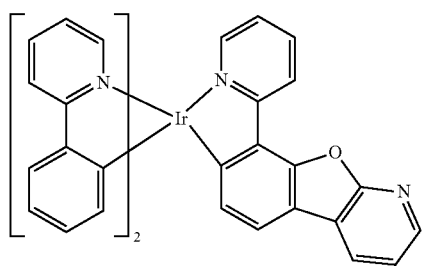
D36 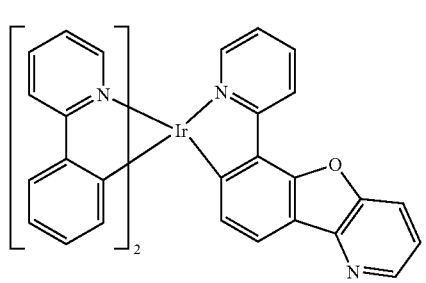
D37 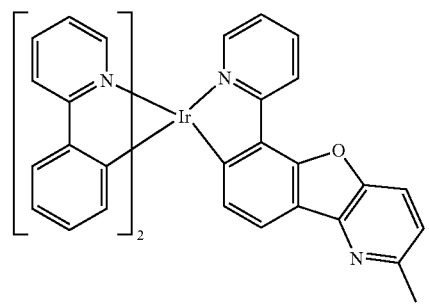
D38 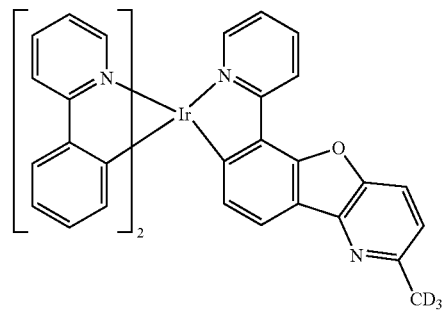
D39 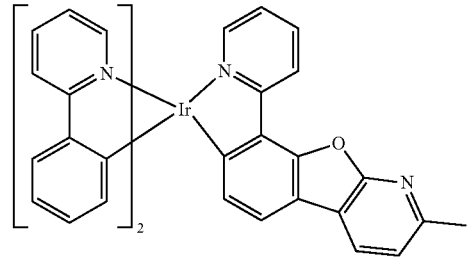
D40 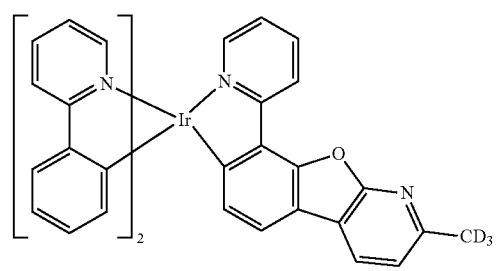
D41 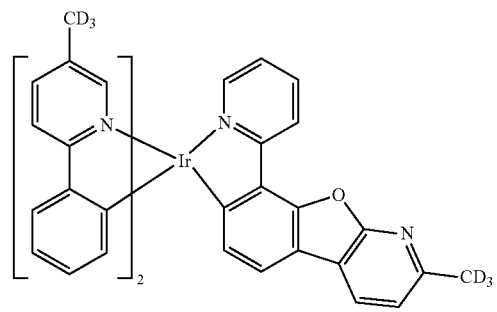

-continued
D42
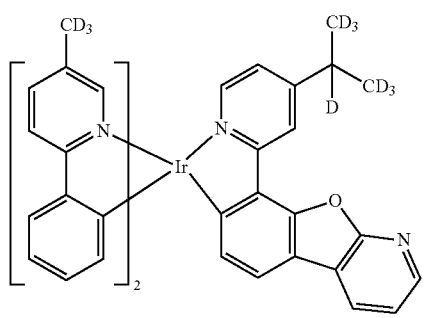
D43
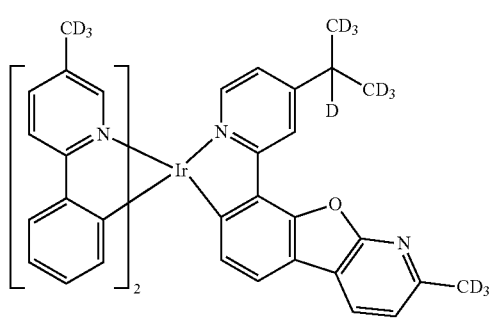
D44
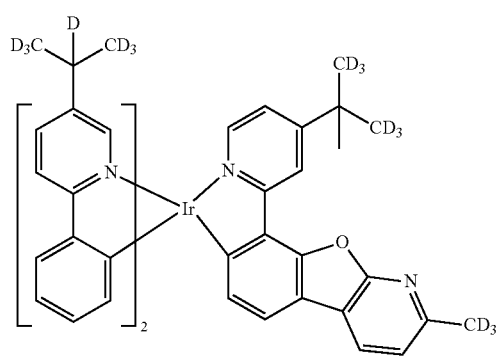
D45
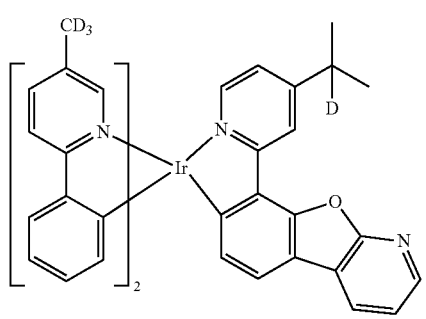
-continued
D46
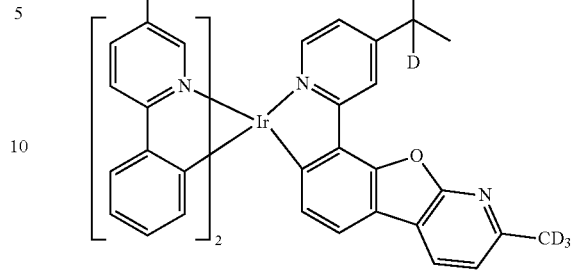
D47
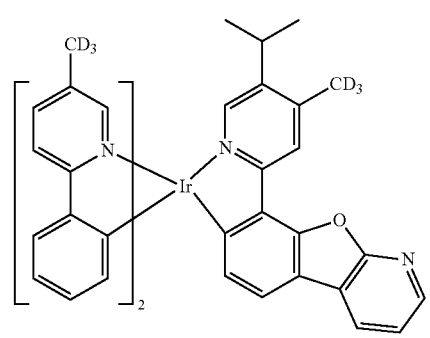
D48
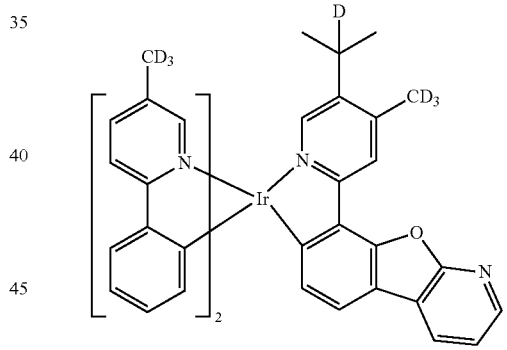
D49
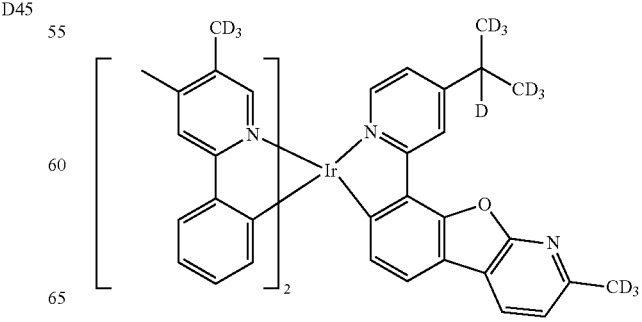

D50
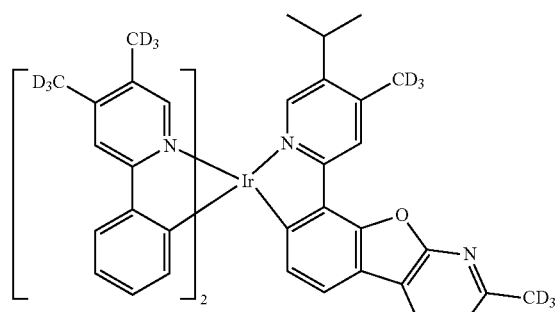
D51
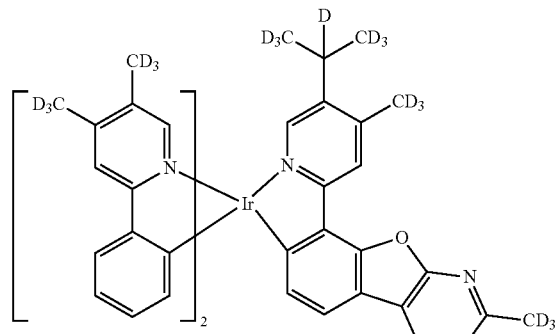
D52
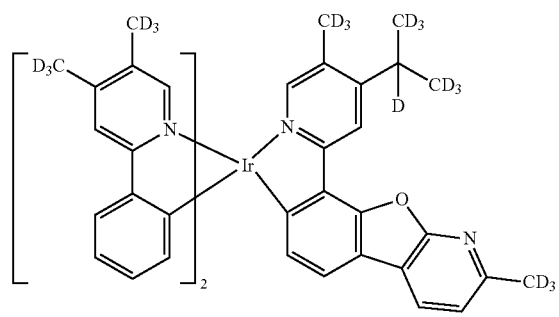
D53
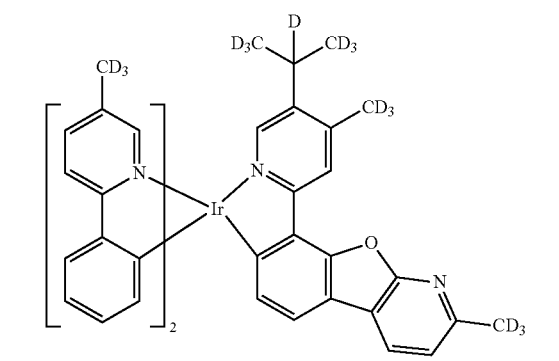
D54
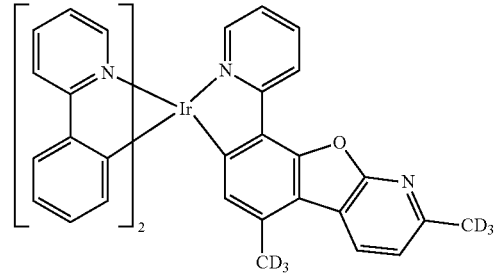
D55
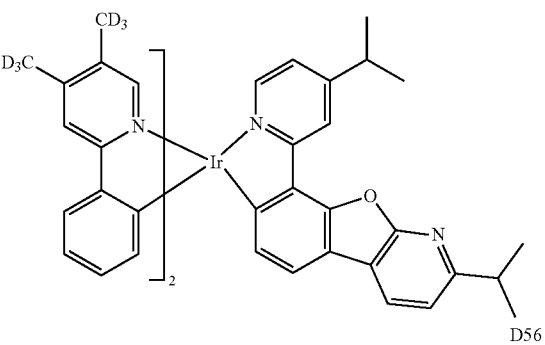
D56
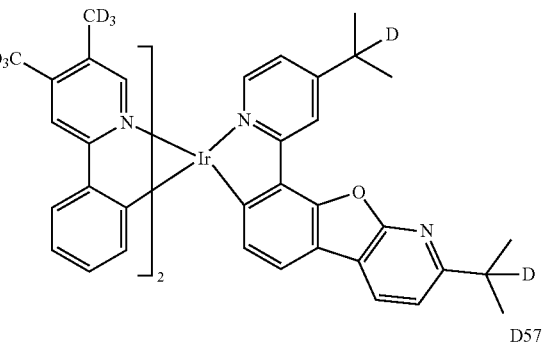
D57
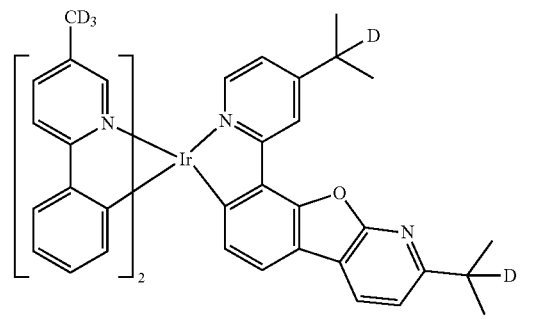
D58
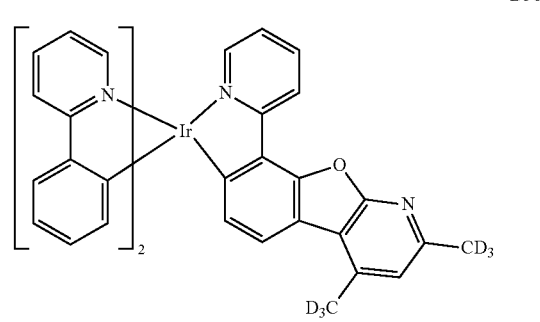

D59
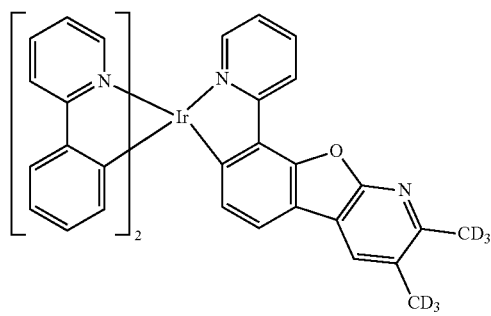
D60
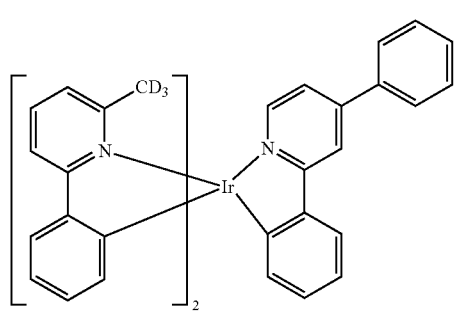
D61
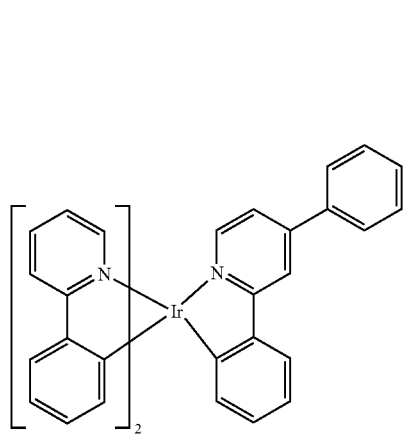
D62
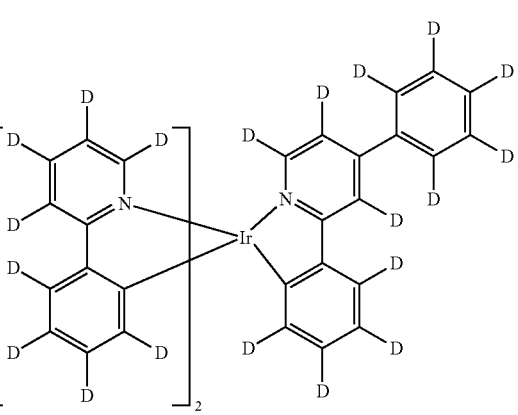
D63
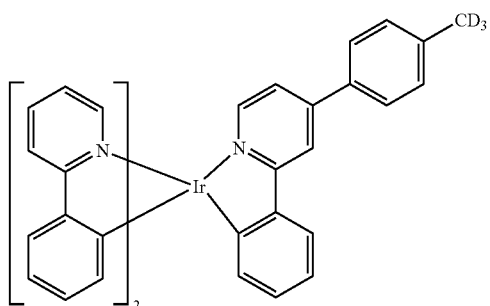
D64
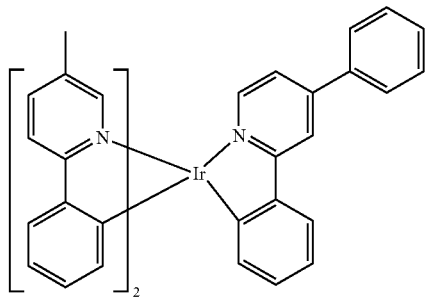
D65
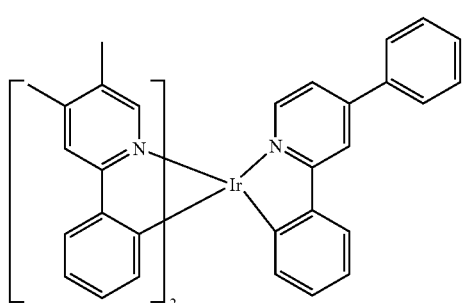
D66
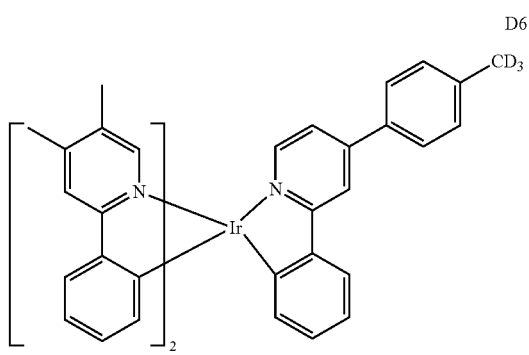
D67
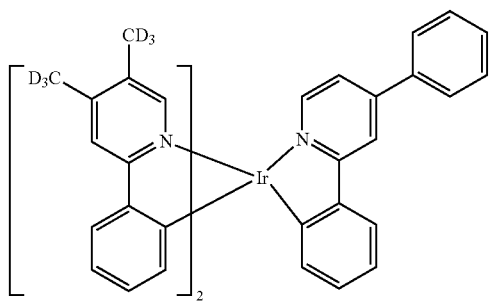

D68
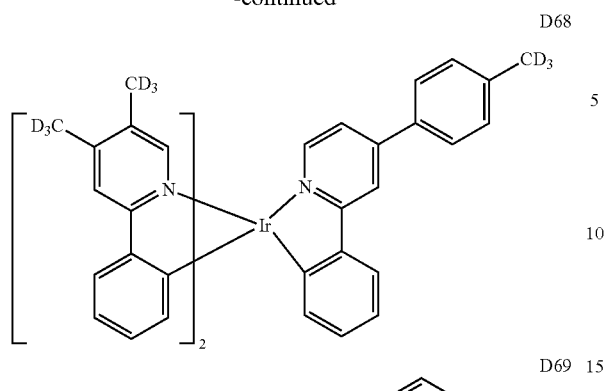
D69
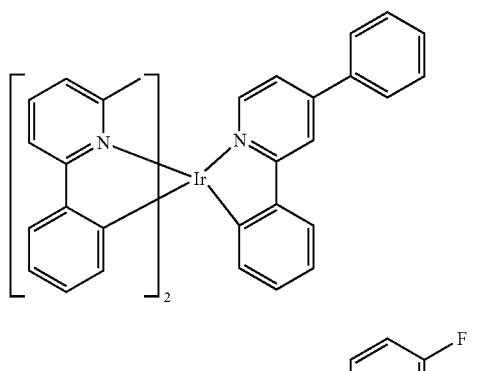
D70
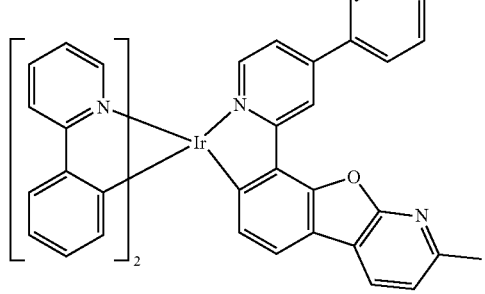
D71
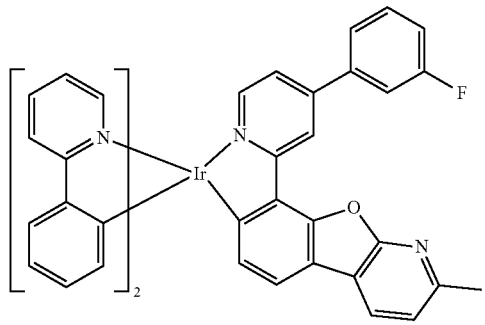
D72
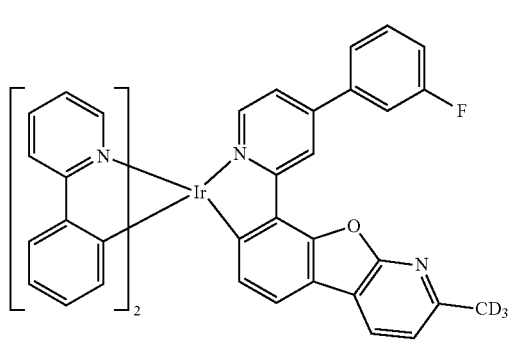
D73
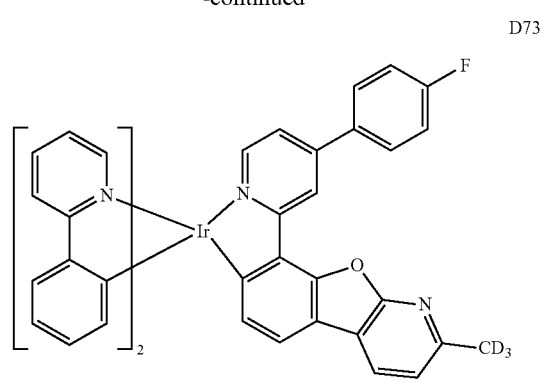
D74
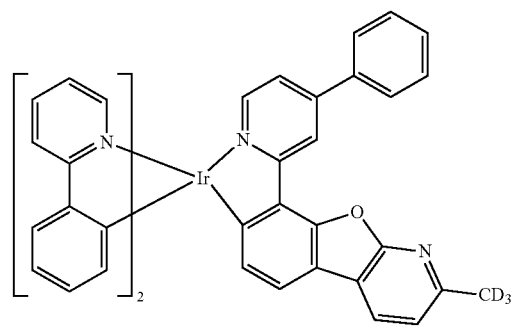
D75
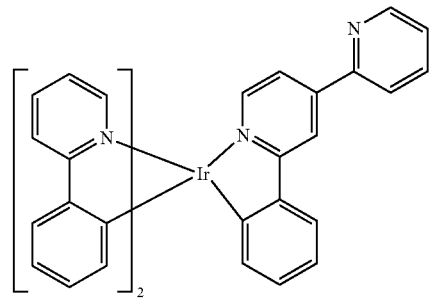
D76
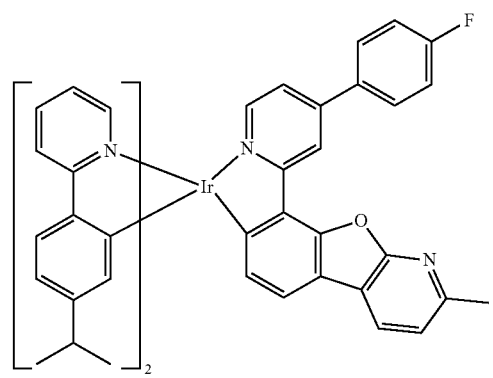

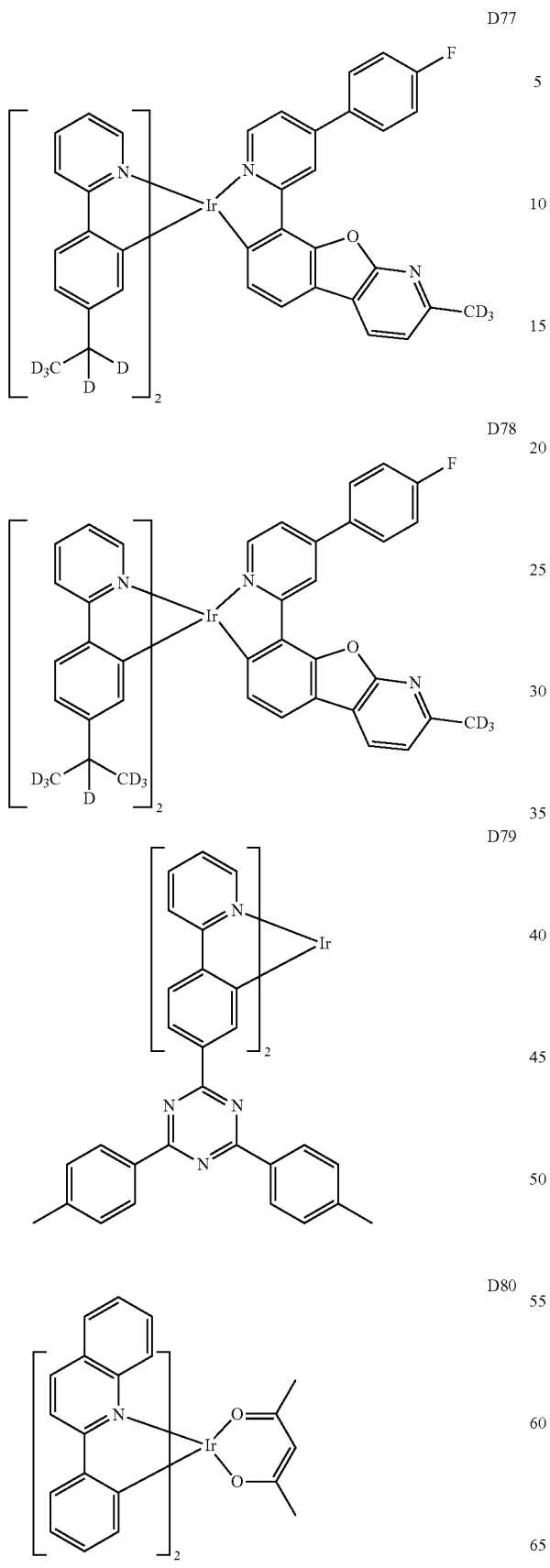
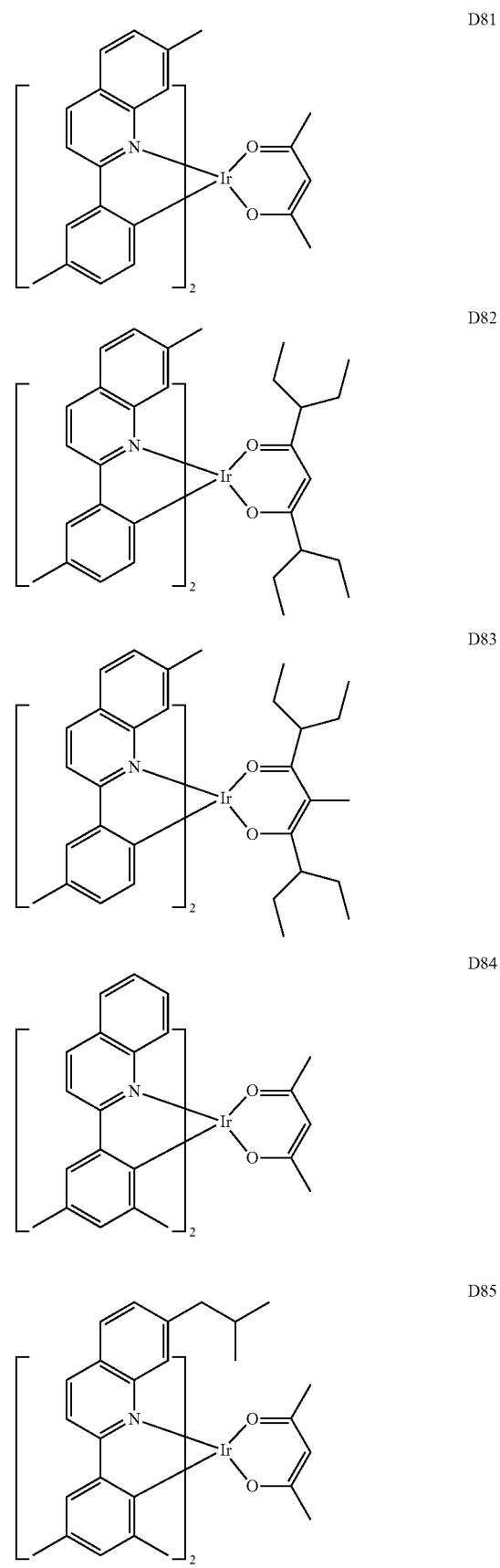

-continued
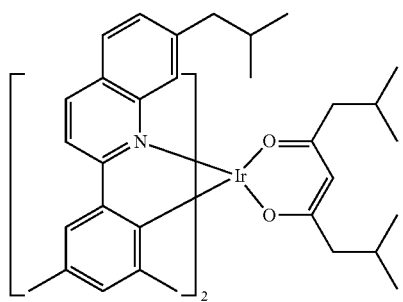
D86
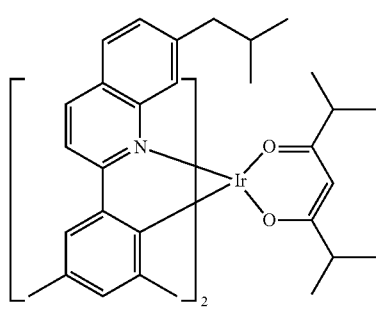
D87
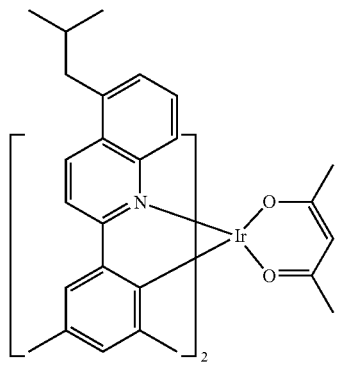
D88
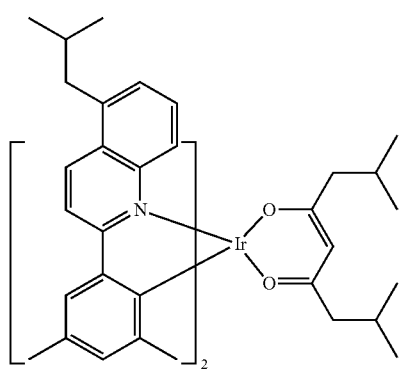
D89
-continued
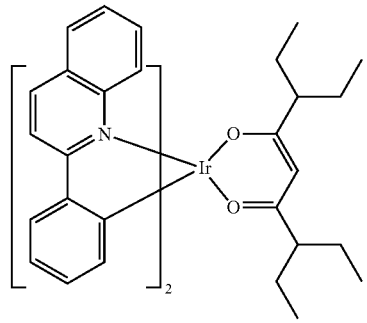
D90
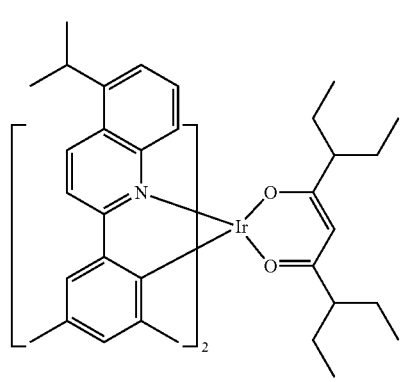
D91
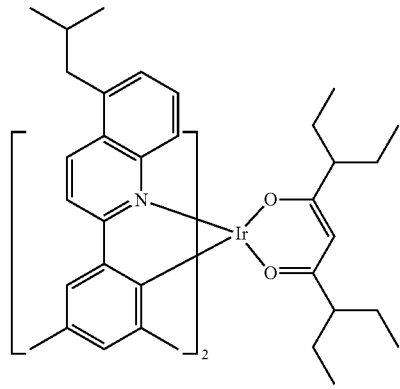
D92
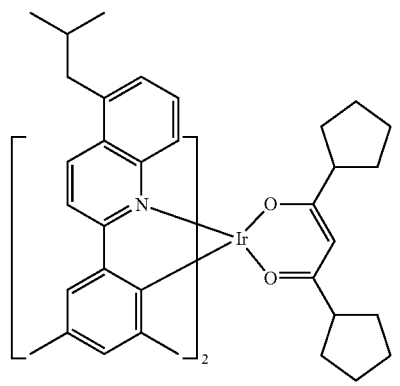
D93

D94
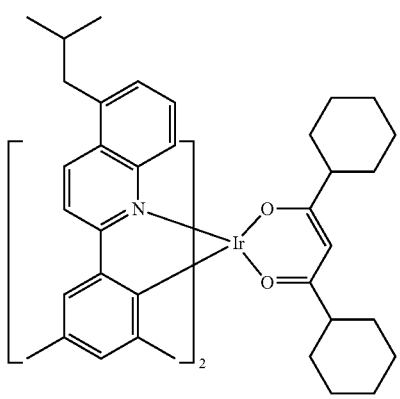
D95
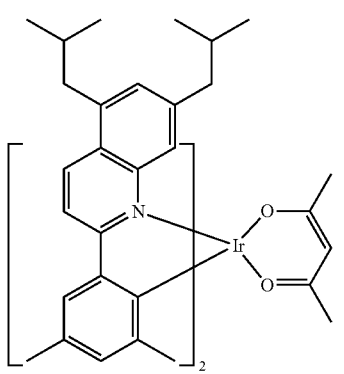
D96
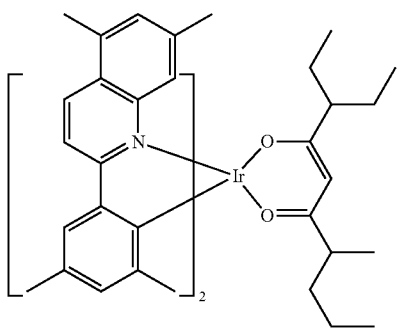
D97
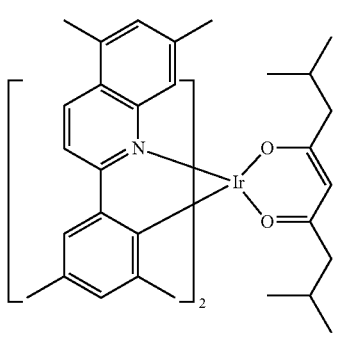
D98
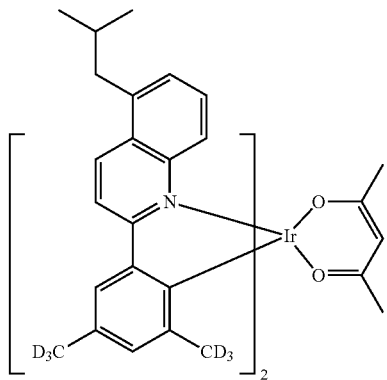
D99
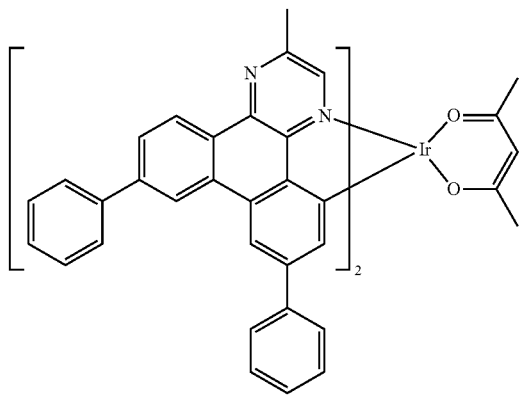
D100
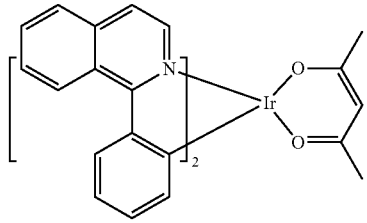
D101
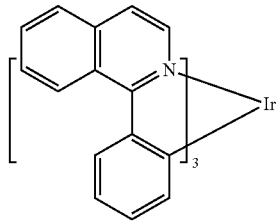
D102
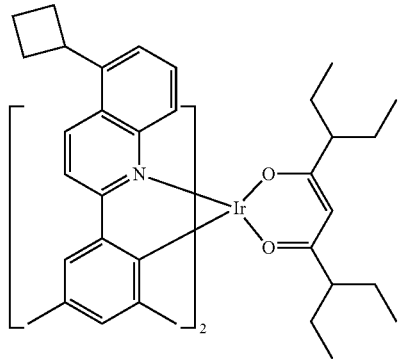

D103
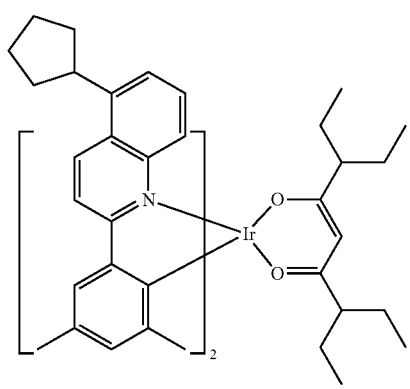
D104
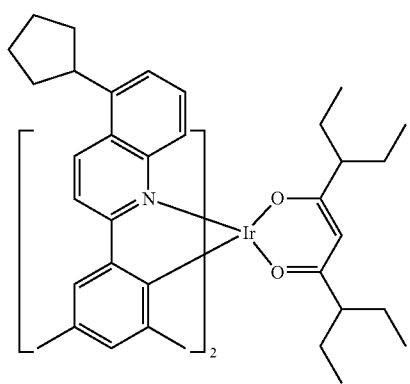
D105
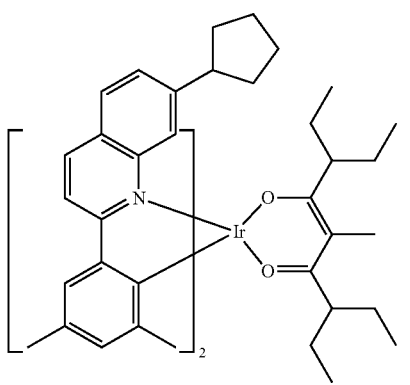
D106
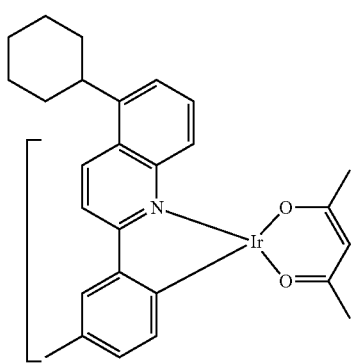
D107
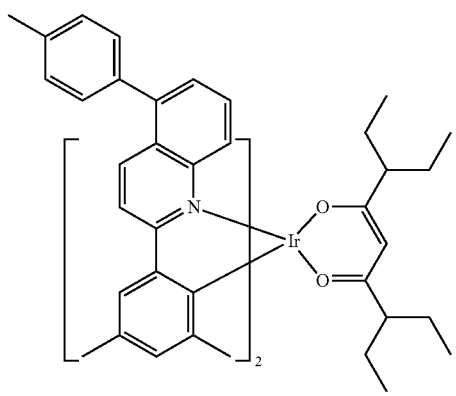
D108
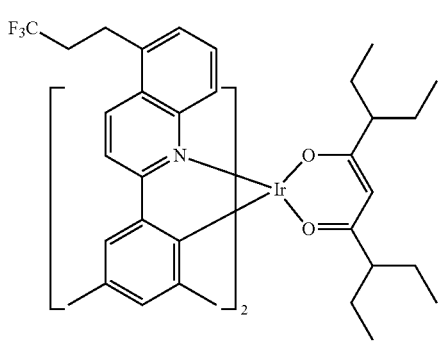
D109
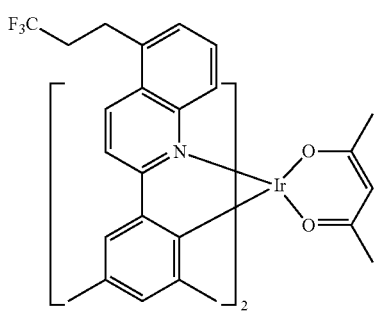
D110
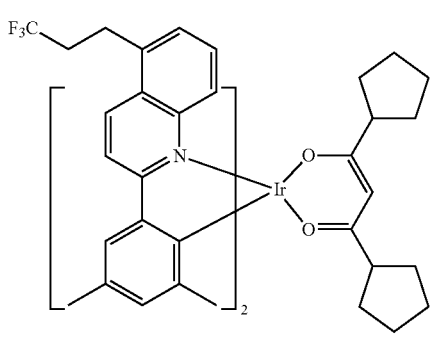

-continued
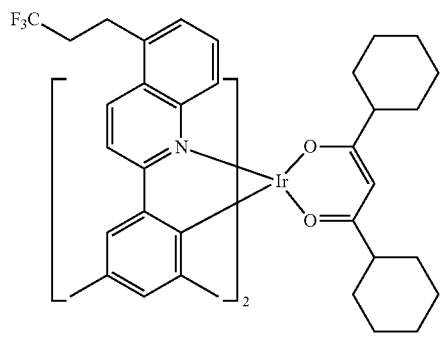
D111
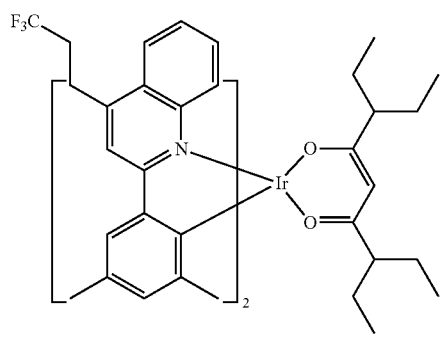
D112
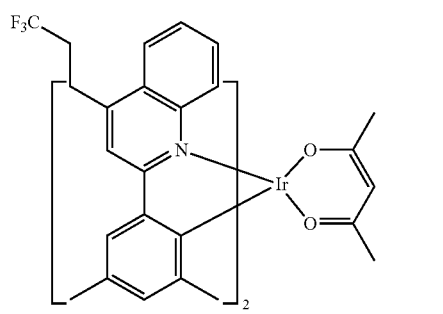
D113
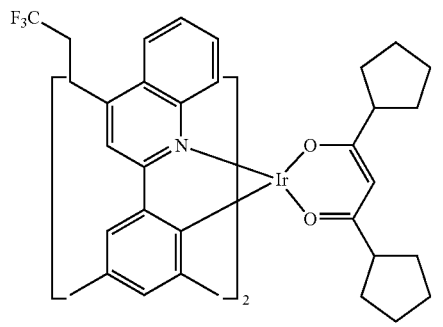
D114
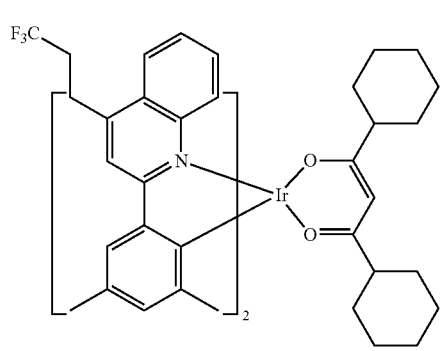
D115
-continued
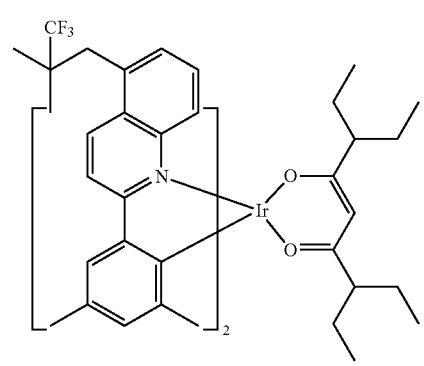
D116
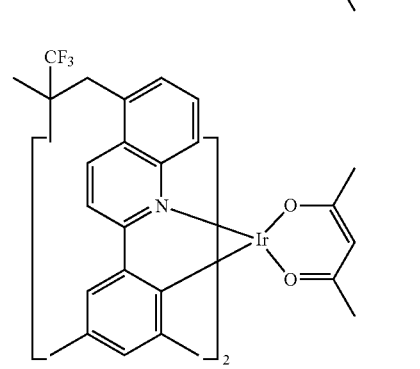
D117
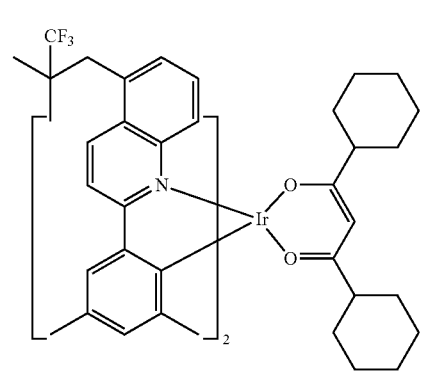
D118
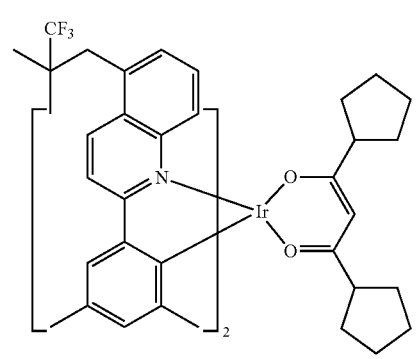
D119

D120 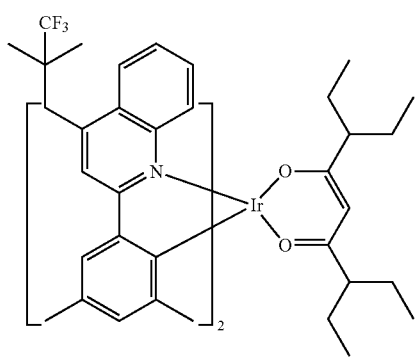
D121 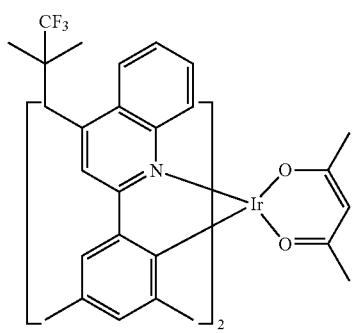
D122 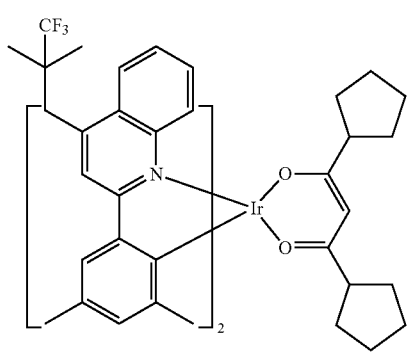
D123 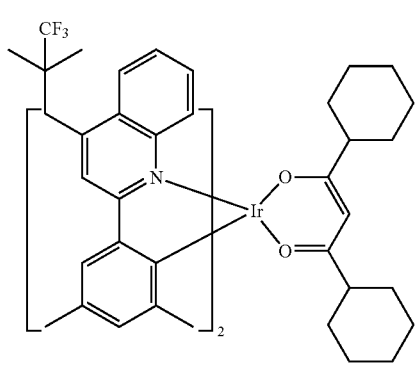
D124 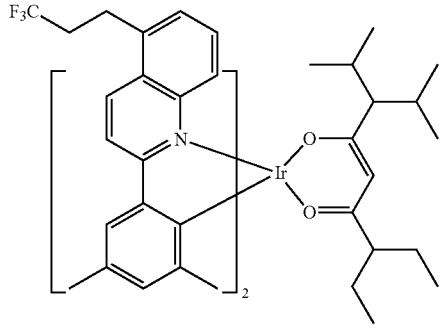
D125 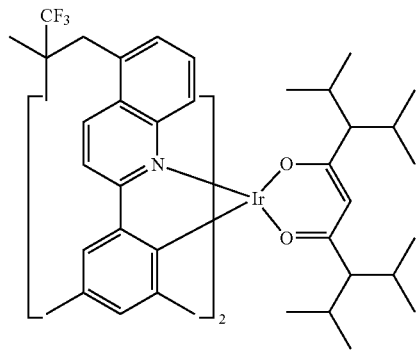
D126
D127

-continued
D128
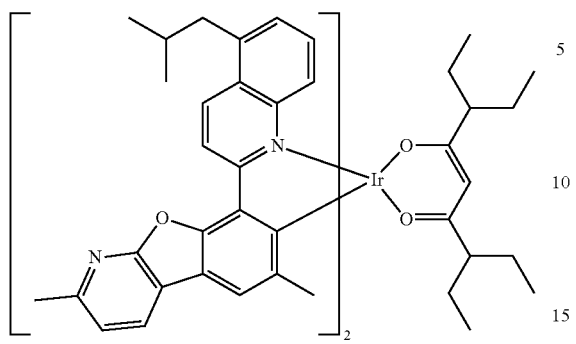
D129
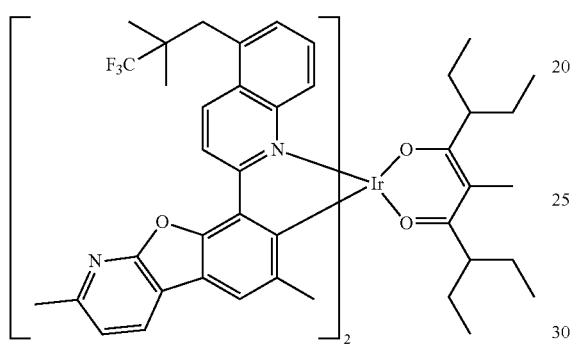
D130
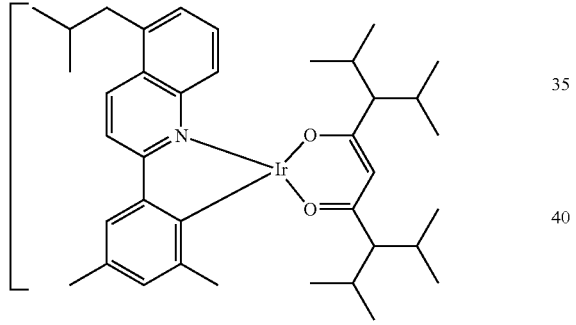
D131
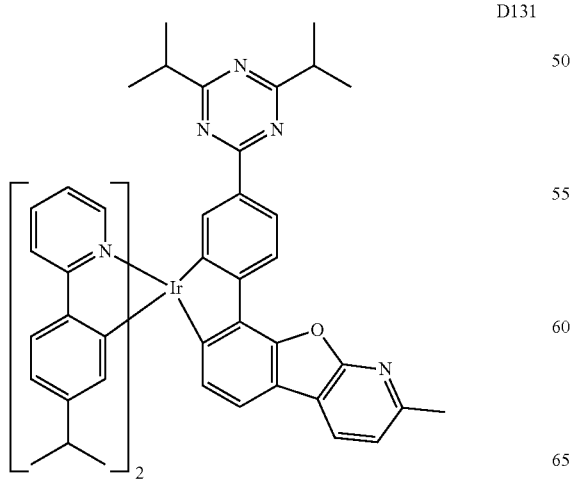
-continued
D132
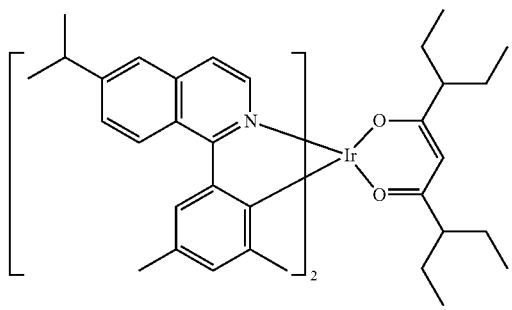
D133
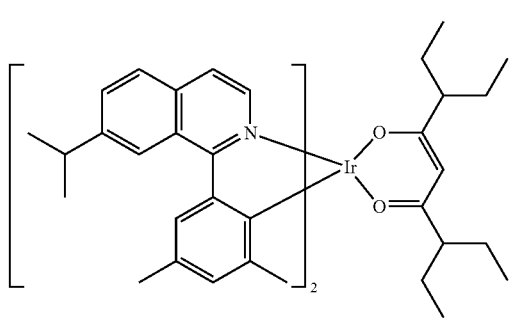
D134
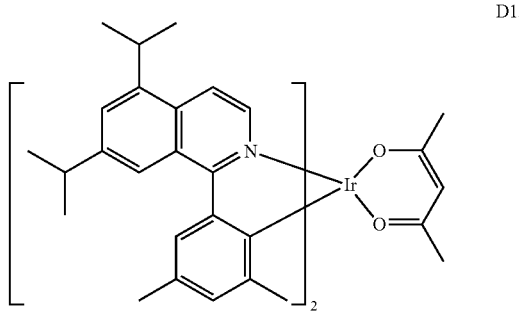
D135
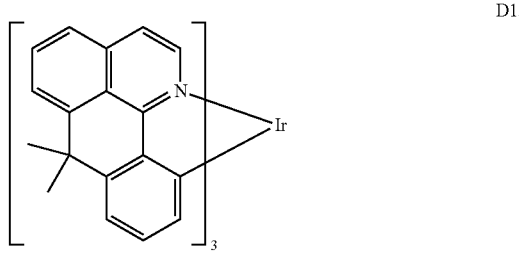
D136
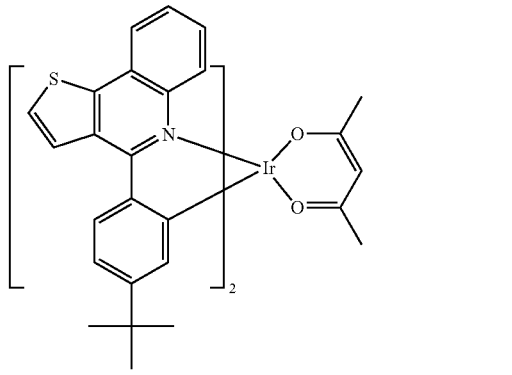

-continued

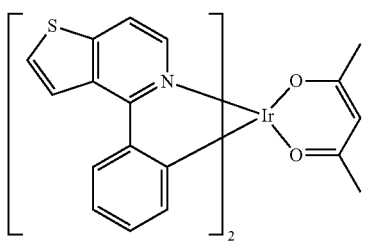
D137

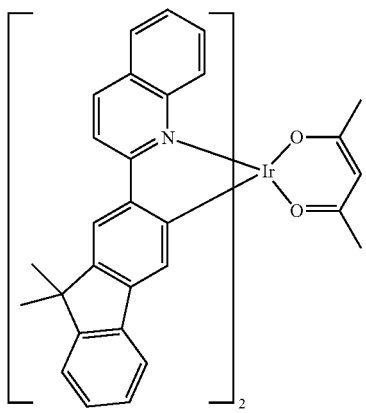
D138

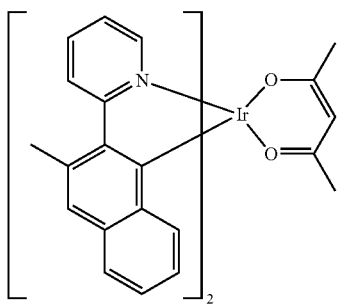
D139

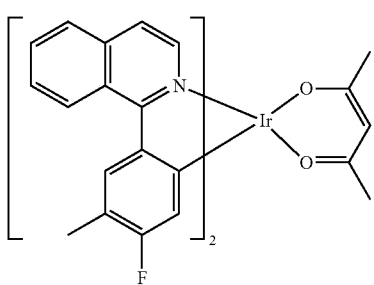
D140

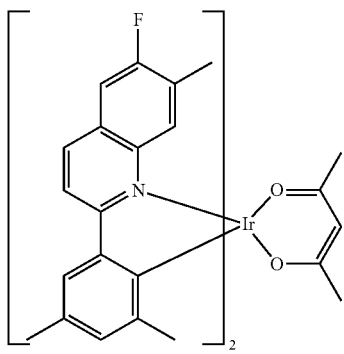
D141

-continued

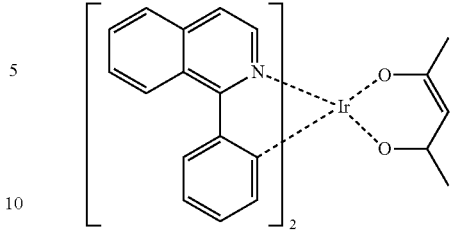
D142

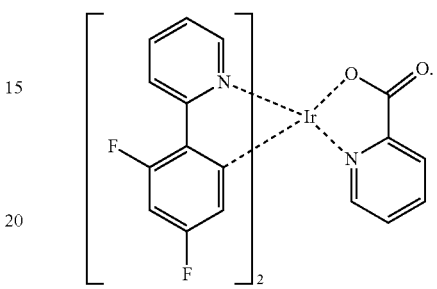
D143

The phosphorescent dopant, is not limited to the above-described example compound, and may be any known phosphorescent platinum group metal complexes described in, for example, paragraphs [0105] to [0113] of US Patent Publication No. 2016/0093808, Japanese Patent Application Publication No. 2014-509067, and the like, and each are herein incorporated in the present disclosure. The phosphorescent platinum group metal complexes described in these references may also be used as a ground for corrections herein.

The quantum dot may be a nanoparticle of a II-VI group semiconductor compound, a III-V group semiconductor compound, or a IV-VI group semiconductor compound. For example, the quantum dot may be CdO, CdS, CdSe, CdTe, ZnO, ZnS, ZnSe, ZnTe, HgS, HgSe, HgTe, MgSe, MgS CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, GaY, GaP, GaAs, AlY, AlP, AlAs, InY, InP, InAs, InSb, GaYP, GaYAs, GaYSb, GaPAs, GaPSb, AlYP, AlYAs, AlYSb, AlPAs, AlPSb, InYP, InYAs, InPAs, InPSb, GaAlYP, SnS, SnSe, SnTe, PbS, PbSe, PbTe, SnSeS, SnSeTe, SnSTe, PbSeS, PbSeTe, PbSTe, SnPbS, SnPbSe, SnPbTe, or the like, but embodiments of the present disclosure are not limited thereto. In addition, a particle diameter of the quantum dot is not particularly limited, but may be, for example, in a range of about 1 nm to about 20 nm. The quantum dot may have a single-core structure or a core-shell structure.

The amount of luminescent material in the composition may be, based on 100 parts by weight of the condensed cyclic compound represented by Formula 1 or Formula 2 functioning as a host material, from about 0.5 parts by weight to about 50 parts by weight, for example, from about 1 part by weight to about 30 parts by weight, or, for example, about 2 parts by weight to about 25 parts by weight.

The amount of luminescent material in the composition may be, based on 100 parts by weight of the total weight of the condensed cyclic compound represented by Formula 1 or Formula 2 functioning as a host material, the first compound, and the second compound, from about 0.5 parts by weight to about 50 parts by weight, for example, from about 1 part by weight to about 30 parts by weight, or, for example, about 2 parts by weight to about 25 parts by weight.

Within these ranges, the solubility of the composition is further increased, and precipitation is minimized in the solution, and thus, the pot life of the solution may be prolonged. Further, the luminescent efficiency and light-emission lifespan of organic light-emitting devices are improved.

For example, the composition may include the condensed cyclic compound, the first compound, the second compound, and the luminescent material (e.g., phosphorescent dopant).

Figure 4:
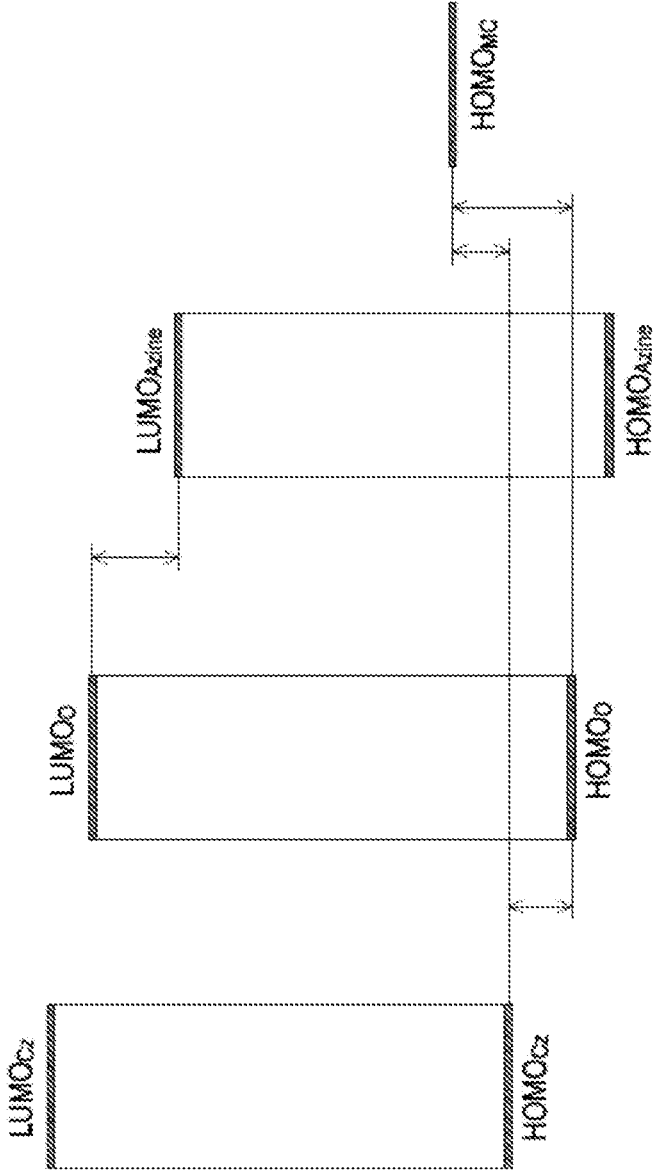
FIG. 4 shows a diagram illustrating an exemplary energy level relationship among a condensed cyclic compound represented by Formula 1, a first compound including a carbazole group, a second compound including an azine group, and a phosphorescent platinum group metal complex in a composition according to an embodiment.

FIG. 3 shows a diagram illustrating an exemplary energy level relationship among a condensed cyclic compound represented by Formula 1, a second compound including an azine group, and a phosphorescent platinum group metal complex in a composition according to an embodiment. FIG. 4 shows a diagram illustrating an exemplary energy level relationship among a condensed cyclic compound represented by Formula 1, a first compound including a carbazole group, a second compound including an azine group, and a phosphorescent platinum group metal complex in a composition according to an embodiment.

As shown in FIG. 3, LUMO ($LUMO_0$) of the condensed cyclic compound represented by Formula 1 or Formula 2 is shallower than LUMO ($LUMO_{Azine}$) of the second compound. In addition, the HOMO ($HOMO_0$) of the condensed cyclic compound represented by Formula 1 or 2 is deeper than the HOMO ($HOMO_{Cz}$) of the first compound. In addition, the hole mobility of the condensed cyclic compound represented by Formula 1 is lower than that of the first compound.

Referring to FIG. 4, $LUMO_0$ is shallower than $LUMO_{Azine}$. $HOMO_0$ is deeper than $HOMO_{Cz}$. In addition, the hole mobility of the condensed cyclic compound represented by Formula 1 is lower than that of the first compound.

Therefore, when the composition including the condensed cyclic compound represented by Formula 1, a hole transport host material such as a first compound, an electron transport host material such as a second compound, and the phosphorescent luminescent metal complex of platinum group is included in the emission layer, the following mechanism would occur.

First, electrons are trapped in the deepest $LUMO_{Azine}$ in an organic layer including the composition. However, the trapped electrons are detrapped in $LUMO_0$ and continue to move. Therefore, in the organic layer, electrons move by the repetition of the trapping and the detrapping, and the electron mobility decreases. This is the same as the embodiment illustrated in FIG. 3.

Meanwhile, holes are trapped in HOMO ($HOMO_{MC}$) of phosphorescent luminescent metal complexes. The trapped holes are then detrapped in $HOMO_{Cz}$ to resume their movement. In addition, the condensed cyclic compound represented by Formula 1 is present in the organic layer at a certain ratio.

The composition may further include a solvent.

For example, the solvent may have a boiling point of about 100° C. or higher and about 350° C. or lower at 101.3 kPa (1 atm). For example, the boiling point of the solvent may be about 150° C. or more and about 320° C. or less, for example about 180° C. or more and about 300° C. or less.

The amount of the solvent in the composition is not particularly limited. For example, the concentration of the condensed cyclic compound in the composition may be about 0.05 wt % or more and about 10 wt % or less, for example, about 0.1 wt % or more and about 6 wt % or less. When the concentration of the condensed cyclic compound is within the above range, it is preferable in terms of solubility, and precipitation is unlikely to occur in the solution, and the pot life of the solution is improved.

For example, the concentration of other compounds (for example, the first compound, the second compound, the phosphorescent luminescent metal complex, etc.), which are different from the condensed cyclic compound, in the composition, may be about 0.05 wt % or more and about 10 wt % or less, and, for example, about 0.1 wt % or more and about 6 wt % or less. When the concentration of the other compounds is within the above range, it is preferable in terms of solubility, and precipitation is unlikely to occur in the solution, and the pot life of the solution is improved.

The solvent is not particularly limited, so long as it is capable of dissolving the condensed cyclic compound represented by Formula 1 and/or the first compound represented by Formula 9. For example, the solvent may be octane, nonane, decane, undecane, dodecane, toluene, xylene, benzonitrile, 3-methylbenzonitrile, dimethylacetamide, N-methylpyrrolidone, N,N-dimethyl formamide, dimethylsulfoxide, hexamethylphosphoric acid triamide, phenylcyclohexane, tetrahydronaphthalene, ethylbenzene, n-propylbenzene, isopropylbenzene, diethylbenzene, mesitylene, propylbenzene, n-butylbenzene, sec-butylbenzene, 1-phenylpentane, 2-phenylpentane, 3-phenylpentane, phenylcyclopentane, 2-ethylbiphenyl, 3-ethylbiphenyl, cyclohexylbenzene, dimethoxybenzene, 1,4-dioxane, 1,2-diethoxyethane, diethyleneglycol dimethyl ether, diethyleneglycol diethyl ether, ethoxybenzene, 3-methylanisole, m-dimethoxybenzene, 2-hexanone, 3-hexanone, cyclohexanone, 2-heptanone, 3-heptanone, 4-heptanone, cycloheptanone, butylacetate, butylpropionate, heptylbutyrate, propylenecarbonate, anisole, ethoxytoluene, phenoxytoluene, isopropylbiphenyl, dimethylanisole, phenyl acetate, phenyl propionic acid, methyl benzoate, ethyl benzoate, 1-propylbenzoate, 1-butylbenzoate, or the like, or any combination thereof, but embodiments of the present disclosure are not limited thereto.

Thus, the composition may be used as a material for a light-emitting device (for example, an organic light-emitting device, a quantum dot light-emitting device, etc.). Specifically, the composition may be used in an emission layer, a charge injection layer, and/or a charge transport layer of a light-emitting device. In one or more embodiments, the composition may be used in an emission layer of a light-emitting device. In one or more embodiments, the composition may be used when a light-emitting device is manufactured by using a solution coating method, wherein the current efficiency and light-emission lifespan of the light-emitting device may be maintained or improved.

Organic Light-Emitting Device

Figure 5:
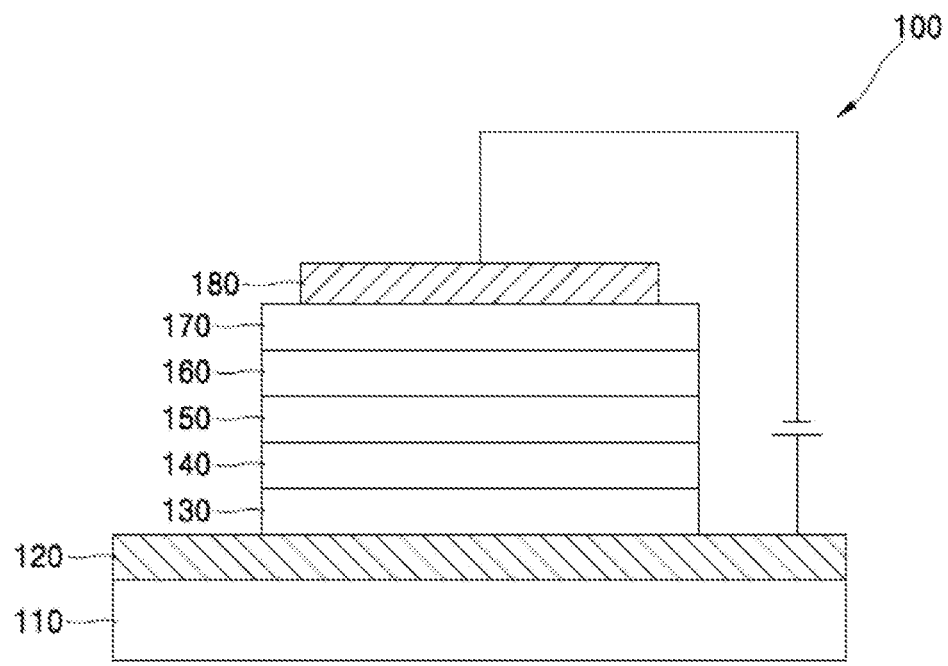
FIG. 5 is a schematic cross-sectional view of an organic light-emitting device according to an embodiment.

Hereinafter, an organic light-emitting device according to an embodiment will be described in detail with reference to FIG. 5. FIG. 5 is a schematic cross-sectional view of an organic light-emitting device according to an embodiment.

An organic light-emitting device 100 according to an embodiment includes a substrate 110, a first electrode 120 disposed on the substrate 110, a hole injection layer 130 disposed on the first electrode 120, a hole transport layer 140 disposed on the hole injection layer 130, an emission layer 150 disposed on the hole transport layer 140, an electron transport layer 160 disposed on the emission layer 150, an electron injection layer 170 disposed on the electron transport layer 160, and a second electrode 180 disposed on the electron injection layer 170.

The condensed cyclic compound represented by Formula 1 may be included in, for example, at least one of organic layers (e.g., at least one selected from the hole injection layer 130, the hole transport layer 140, the emission layer 150, the electron transport layer 160, and the electron injection layer 170) disposed between the first electrode 120 and the second electrode 180. In detail, the condensed cyclic compound represented by Formula 1 may be included as a host in the emission layer 150. For example, the condensed cyclic compound represented by Formula 1 may be included in other organic layers in addition to the emission layer 150. For example, the condensed cyclic compound represented by Formula 1 may be included as a charge transport material in the hole injection layer 130 and/or the hole transport layer 140.

The term "organic layer" as used herein refers to a single layer and/or a plurality of layers between the first electrode and the second electrode of the organic light-emitting device. The "organic layer" may include, in addition to an organic compound, an organometallic compound including metal.

The expression "(an organic layer) includes at least one condensed cyclic compound" used herein may include a case in which "(an organic layer) includes identical compounds represented by Formula 1" and a case in which "(an organic layer) includes two or more different condensed cyclic compounds represented by Formula 1".

For example, the organic layer may include only Compound 1 as the condensed cyclic compound. In this regard, Compound 1 may exist in an emission layer of the organic light-emitting device. Or, the organic layer may include Compound 1 and Compound 2 as the condensed cyclic compound. In this regard, Compound 1 and Compound 2 may exist in an identical layer (for example, Compound 1 and Compound 2 all may exist in an emission layer).

The substrate 110 may be any substrate that is used in an organic light-emitting device according to the related art. For example, the substrate 110 may be a glass substrate, a silicon substrate, or a transparent plastic substrate, each having excellent mechanical strength, thermal stability, surface smoothness, ease of handling, and water resistance, but embodiments of the present disclosure are not limited thereto.

The first electrode 120 may be formed on the substrate 110. The first electrode 120 may be, for example, an anode, and may include a material with a high work function to facilitate hole injection, such as an alloy or a conductive compound. The first electrode 120 may be a reflective electrode, a semi-reflective electrode, or a transmissive electrode. The first electrode 120 may have a single-layered structure or a multi-layered structure including two or more layers. For example, the first electrode 120 may be a transparent electrode formed of indium tin oxide (ITO), indium zinc oxide (IZO), tin oxide ($SnO_2$), or zinc oxide (ZnO), which has excellent transparency and conductivity. On the transparent first electrode 120, magnesium (Mg), aluminum (Al), aluminum-lithium (Al—Li), calcium (Ca), magnesium-indium (Mg—In), or magnesium-silver (Mg—Ag) may be disposed, so as to form a reflective electrode. In one or more embodiments, the first electrode 120 may have a three-layered structure of ITO/Ag/ITO, but embodiments of the present disclosure are not limited thereto.

The hole transport region may be disposed on the first electrode 120.

The hole transport region may include at least one a hole injection layer 130, a hole transport layer 140, an electron blocking layer (not shown), a buffer layer (not shown), or any combination thereof.

The hole transport region may include only either a hole injection layer or a hole transport layer 140. In one or more embodiments, the hole transport region may have a hole injection layer/hole transport layer structure or a hole injection layer/hole transport layer/electron blocking layer structure, wherein for each structure, constituting layers are sequentially stacked from the first electrode 120 in the stated order.

The hole injection layer 130 may include, for example, at least one poly(ether ketone)-containing triphenylamine (TPAPEK), 4-isopropyl-4'-methyldiphenyliodonium tetrakis(pentafluorophenyl) borate (PPBI), Y,Y'-diphenyl-Y,Y'-bis-[4-(phenyl-m-tolyl-amino)-phenyl]-biphenyl-4,4'-diamine (DYTPD), copper phthalocyanine, 4,4',4"-tris(3-methylphenylphenylamino triphenylamine (m-MTDATA), Y,Y'-di(1-naphthyl)-Y,Y'-diphenylbenzidine (YPB), 4,4',4"-tris(diphenylamino) triphenylamine (TDATA), 4,4',4"-tris(Y,Y-2-naphthylphenylamino) triphenylamine (2-TYATA), polyaniline/dodecylbenzenesulphonic acid (PAYI/DBSA), poly(3,4-ethylenedioxythiophene)/poly(4-styrenesulfonate) (PEDOT/PSS), polyaniline/10-camphorsulfonic acid (PAYI/CSA), polyaniline/poly(4-styrenesulfonate) PAYI/PSS), or any combination thereof.

The hole injection layer 130 may be formed to a thickness in a range of about 10 nm to about 1,000 nm, for example, about 10 nm to about 100 nm.

The hole transport layer 140 may include, for example, at least one of a carbazole derivative, such as 1,1-bis[(di-4-tolylamino)phenyl] cyclohexane (TAPC), Y-phenylcarbazole, and polyvinylcarbazole, Y,Y'-bis(3-methylphenyl)-Y,Y'-diphenyl-[1,1-biphenyl]-4,4'-diamine (TPD), 4,4',4"-tris(Y-carbazolyl) triphenylamine (TCTA), Y,Y'-di(1-naphthyl)-Y,Y'-diphenylbenzidine (YPB), and poly(9,9-dioctyl-fluorene-co-Y-(4-butylphenyl)-diphenylamine (TFB).

The hole transport layer 140 may be formed to a thickness in a range of about 10 nm to about 1,000 nm, for example, about 10 nm to about 150 nm.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one a quinone derivative, a metal oxide, and a cyano group-containing compound, but embodiments of the present disclosure are not limited thereto. Non-limiting examples of the p-dopant are a quinone derivative, such as tetracyanoquinodimethane (TCYQ) or 2,3,5,6-tetrafluoro-tetracyano-1,4-benzoquinodimethane (F4-TCYQ); a metal oxide, such as a tungsten oxide or a molybdenum oxide; and a cyano group-containing compound, such as Compound HT-D1 or HT-D2 below, but are not limited thereto:

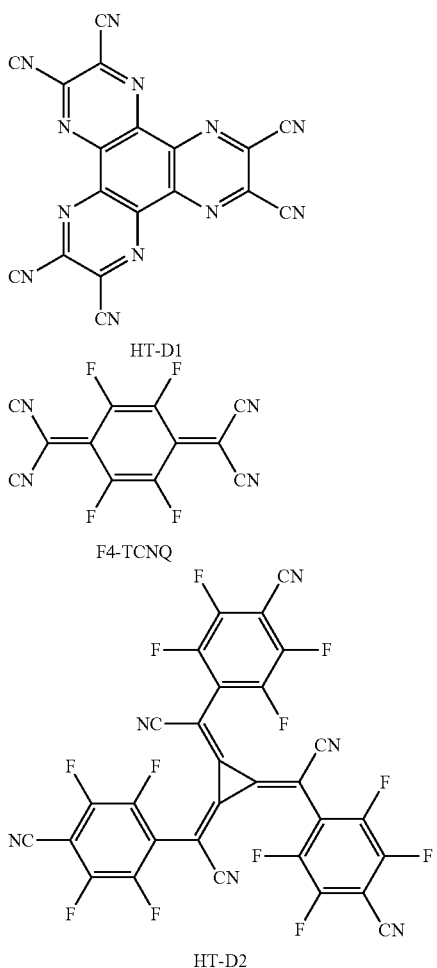

HT-D1

F4-TCNQ

HT-D2

Meanwhile, when the hole transport region includes a buffer layer, a material for forming the buffer layer may be a material for forming the hole transport region described above and a material for a host to be explained later. However, the material for forming the buffer layer is not limited thereto.

In addition, when the hole transport region includes an electron blocking layer, a material for forming the electron blocking layer may be a material for forming the hole transport region described above and a material for a host to be explained later. However, the material for forming the electron blocking layer is not limited thereto. For example, when the hole transport region includes an electron blocking layer, a material for the electron blocking layer may be mCP.

The emission layer 150 is formed on the hole transport region. The emission layer 150 emits light by fluorescence or phosphorescence. The emission layer 150 may include a host and/or a dopant, and the dopant may include the condensed cyclic compound represented by Formula 1. In addition, for use as the host and the dopant in the emission layer 150, any known material may be used.

For example, the host may include (tris(8-quinolinato) aluminium ($Alq_3$), 4,4'-bis(carbazol-9-yl)biphenyl (CBP), poly(n-vinylcarbazole) (PVK), 9,10-di(naphthalene)anthracene (ADY), 4,4',4"-tris(Y-carbazolyl)triphenylamine (TCTA), 1,3,5-tris(Y-phenyl-benzimidazol-2-yl)benzene (TPBi) 3-tert-butyl-9,10-di(naphth-2-yl)anthracene (TBADY), distyrylarylene (DSA), 4,4'-bis(9-carbazole)-2, 2'-dimethyl-bipheny (dmCBP), or the like, but embodiments of the present disclosure are not limited thereto.

In one or more embodiments, the host may further include one of the first compound and the second compound, but embodiments of the present disclosure are not limited thereto.

For example, the dopant may include a perylene or a derivative thereof, a rubrene or a derivative thereof, a coumarin or a derivative thereof, a DCM or a derivative thereof, an iridium complex, such as Firpic, $Ir(piq)_2(acac)$, $Ir(ppy)_3$, and tris(2-(3-p-xylyl)phenyl)pyridine iridium (III) (dopant), or the like, an osmium complex, or a platinum complex, but embodiments of the present disclosure are not limited thereto.

When the emission layer includes a host and a dopant, an amount of the dopant may be in a range of about 0.01 parts by weight to about 15 parts by weight based on 100 parts by weight of the host, but embodiments of the present disclosure are not limited thereto.

The emission layer 150 may be formed to a thickness in a range of about 10 nm to about 60 nm.

When the organic light-emitting device is a full-color organic light-emitting device, the emission layer may be patterned into a red emission layer, a green emission layer, or a blue emission layer. In one or more embodiments, due to a stacked structure including a red emission layer, a green emission layer, and/or a blue emission layer, the emission layer may emit white light.

The electron transport region may be formed on the emission layer 150.

The electron transport region may include at least one of a hole blocking layer (not shown), an electron transport layer 160, an electron injection layer 170, or any combination thereof.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

For example, to prevent diffusion of excitons or holes into the electron transport layer 160, the organic light-emitting device 100 may further include a hole blocking layer between the electron transport layer 160 and the emission layer 150. The hole blocking layer may include, for example, at least one an oxadiazole derivative, a triazole derivative, BCP, Bphen, BAlq, Compound HB1 below, or any combination thereof, but embodiments of the present disclosure are not limited thereto:

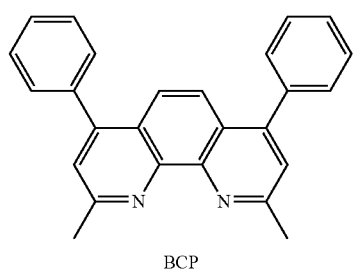

BCP

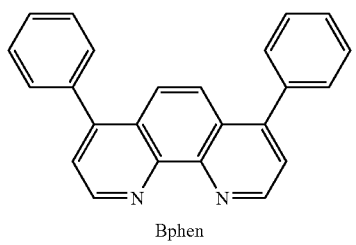

Bphen

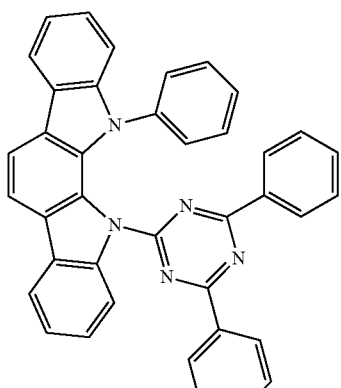

HB1

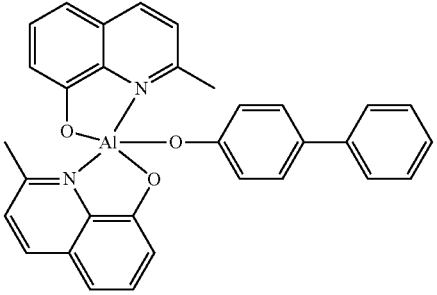

BAlq

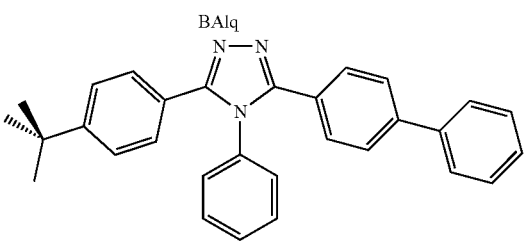

TAZ

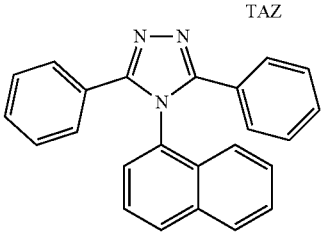

NTAZ

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer 160 may include: a pyridine ring-containing compound, such as tris(8-quinolinato) aluminium ($Alq_3$), BAlq, and 1,3,5-tri[(3-pyridyl)-phen-3-yl] benzene); a triazine ring-containing compound, such as 2,4,6-tris(3'-(pyridin-3-yl)biphenyl-3-yl)-1,3,5-triazine; an imidazole ring-containing compound, such as 2-(4-(Y-phenylbenzimidazolyl-1-yl-phenyl)-9,10-dinaphthylanthracene; a triazole ring-containing compound, such as TAZ and YTAZ; 11,3,5-tris(Y-phenyl-benzimidazol-2-yl)benzene (TPBi); BCP; Bphen; or the like:

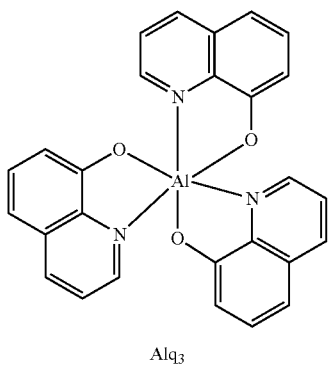

$Alq_3$

In one or more embodiments, the electron transport layer 160 may include a commercial product, such as KLET-01, KLET-02, KLET-03, KLET-10, and KLET-M1 (hereinbefore, available from Chemipro Kasei Inc.).

Also, the electron transport layer 160 may further include, in addition to the materials described above, a metal-containing material.

The metal-containing material may include a Li complex. The Li complex may include, for example, Compound ET-D1 (lithium quinolate, LiQ) or ET-D2:

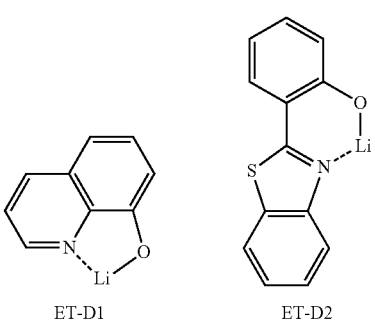

ET-D1             ET-D2

The electron injection layer 160 may be, for example, formed to a thickness in a range of about 15 nm to about 50 nm.

The electron injection layer 170 may be formed on the electron transport layer 160.

The electron injection layer 170 may include, for example, a lithium compound, such as (8-hydroxyquinolinato)lithium (Liq) and lithium fluoride (LiF), sodium chloride (YaCl), cesium fluoride (CsF), lithium oxide ($Li_2O$), or barium oxide (BaO).

The electron injection layer 170 may be formed to a thickness in a range of about 0.3 nm to about 9 nm.

The second electrode 180 may be formed on the electron injection layer 170. The second electrode 180 may be, specifically, a cathode, and may be formed of a material metal, an alloy, an electrically conductive compound, and a combination thereof, which have a relatively low work function. For example, second electrode 180 may be a reflective electrode formed of metal, such as lithium (Li), magnesium (Mg), aluminum (Al), and calcium (Ca), or an alloy, such as aluminum-lithium (Al—Li), magnesium-indium (Mg—In), and magnesium-silver (Mg—Ag). In one or more embodiments, the second electrode 180 may be a transparent electrode having a thickness of 20 nm or less and formed of metal or in a transparent conductive film, such as an alloy thin film, indium tin oxide ($In_2O_3$—$SnO_2$), and indium zinc oxide ($In_2O_3$—ZnO).

In one or more embodiments, the laminated structure of the organic light-emitting device 100 according to an embodiment is not limited to the above-described example. In one or more embodiments, the organic light-emitting device 100 may have other laminated structures. For example, the organic light-emitting device 100 may not include one or more of the hole injection layer 130, the hole transport layer 140, the electron transport layer 160, and the electron injection layer 170, or may include other layers. In one or more embodiments, layers which constitute the organic light-emitting device 100 may each include a single layer or a multiple layers.

The manufacturing method of each layer of the organic light-emitting device 100 according to an embodiment is not particularly limited, and may be manufactured by various methods such as a vacuum deposition method, a solution coating method, an LB method, and the like.

The solution coating method may include a spin coat method, a casting method, a micro gravure coat method, a gravure coat method, a bar coat method, a roll coat method, a wire bar coat method, a dip coat method, a spry coat method, a screen printing method, a flexographic method, a offset printing method, an ink jet printing method, or the like.

The solvent used for the solution coating method may include toluene, xylene, diethyl ether, chloroform, ethyl acetate, dichloromethane, tetrahydrofuran, acetone, acetonitrile, N,N-dimethylformamide, dimethylsulfoxide, anisole, hexamethyl phosphate triamide, 1,2-dichloro ethane, 1,1,2-trichloroethane, chlorobenzene, o-dichlorobenzene, dioxane, cyclohexane, n-pentane, n-hexane, n-heptane, n-octane, n-nonane, n-decane, methyl ethyl ketone, cyclohexanone, butyl acetate, ethyl cellosolve acetate, ethylene glycol, ethylene glycol mono butyl ether, ethylene glycol mono ethyl ether, ethylene glycol mono methyl ether, dimethoxyethane, propylene glycol, diethoxy metane, triethylene glycol mono ethyl ether, glycerin, 1,2-hexanediol, methanol, ethanol, propanol, isopropanol, cyclohexanol, N-methyl-2-pyrrollidone, or the like, or any combination thereof, and may be any material that can dissolve a material for forming each layer.

The concentration of the composition used in the solution coating method may be, in consideration of coating properties, from about 0.1 wt % or more to about 10 wt % or less, for example, about 0.5 wt % or more to about 5 wt % or less, but embodiments are not limited thereto.

The conditions for the vacuum deposition method depends on the compound used, the structure and thermal properties of the target layer. For example, the deposition temperature may be from about 100° C. to about 500° C., the vacuum pressure may be from about $10^{-8}$ torr to about $10^{-3}$ torr, the deposition rate may be from about 0.01 Å/sec to 100 Å/sec.

In one or more embodiments, the first electrode 120 may be an anode, and the second electrode 180 may be a cathode.

For example, the first electrode 120 may be an anode, the second electrode 180 may be a cathode, and the emission layer 150 disposed between the first electrode 120 and the second electrode 180 may include an organic layer. The organic layer may further include a hole transport region between the first electrode 120 and the emission layer 150 and an electron transport region between the emission layer 150 and the second electrode 180. The hole transport region may include at least one layer the hole injection layer 130, the hole transport layer 140, the buffer layer, and the electron blocking layer, and the electron transport region may include at least one of the hole blocking layer, the electron transport layer 160, the electron injection layer 170, or any combination thereof.

In one or more embodiments, the first electrode 120 may be a cathode, and the second electrode 180 may be an anode.

Hereinbefore, the organic light-emitting device has been described with reference to FIG. 5, but embodiments of the present disclosure are not limited thereto.

Description of Substituents

The expression "X and Y may each independently be" as used herein refers to a case where X and Y may be identical to each other, or a case where X and Y may be different from each other.

The term "substituted" as used herein refers to a case where hydrogen of a substituent such as $R_{11}$ may be further substituted with other substituents.

The term "$C_1$-$C_{60}$ alkyl group" as used herein refers to a linear or branched aliphatic saturated hydrocarbon monovalent group having 1 to 60 carbon atoms, and examples thereof include a methyl group, an ethyl group, an n-propyl group, an isopropyl group, an n-butyl group, an isobutyl group, a sec-butyl group, a tert-butyl group, an n-pentyl group, an isopentyl group, a tert-pentyl group, an neopentyl group, a 1,2-dimethylpropyl group, an n-hexyl group, an isohexyl group, a 1,3-dimethylbutyl group, a 1-isopropylpropyl group, a 1,2-dimethylbutyl group, an n-heptyl group, a 1,4-dimethylpentyl group, a 3-ethylpentyl group, a 2-methyl-1-isopropylpropyl group, a 1-ethyl-3-methylbutyl group, an n-octyl group, a 2-ethylhexyl group, a 3-methyl-1-isopropylbutyl group, a 2-methyl-1-isopropyl group, a 1-tert-butyl-2-methylpropyl group, an n-nonyl group, a 3,5,5-trimethyldecyl group, an n-decyl group, an isodecyl group, an n-undecyl group, a 1-methyldecyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group), an n-heneicosyl group, an n-docosyl group, an n-tricosyl group, and an n-tetracosyl group.

The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by -$OA_{101}$ (wherein $A_{101}$ is the $C_1$-$C_{60}$ alkyl group), and examples thereof include a methoxy group, an ethoxy group, a propoxy group, an isopropoxy group, an n-butoxy group, an isobutoxy group, a sec-butoxy group, a tert-butoxy group, an n-pentoxy group, an isopentoxy group, a tert-pentoxy group, an neopentoxy group, an n-hexyloxy group, an isohexyloxy group, a heptyloxy group, an octyloxy group, nonyloxy group, a decyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a 2-ethylhexyloxy group, and a 3-ethylpentyloxy group.

The term "$C_1$-$C_6$ alkylthio group" as used herein refers to a monovalent group represented by -S$A_{102}$ (wherein $A_{102}$ is the $C_1$-$C_{60}$ alkyl group).

As used herein, the term "$C_2$-$C_{60}$ alkenyl group" refers to a hydrocarbon group including at least one carbon-carbon double bond in the middle or terminal of the $C_2$-$C_{60}$ alkyl group. Non-limiting examples of the $C_2$-$C_{60}$ alkenyl group are an ethenyl group, a prophenyl group, and a butenyl group. As used herein, the term "$C_2$-$C_{60}$ alkylene group" refers to a divalent group having the same structure as the $C_2$-$C_{60}$ alkenyl group.

As used herein, the term "$C_2$-$C_{60}$ alkynyl group" refers to a hydrocarbon group including at least one carbon-carbon triple bond in the middle or terminal of the $C_2$-$C_{60}$ alkyl group. Non-limiting examples of the $C_2$-$C_{60}$ alkynyl group are an ethynyl group and a propynyl group. As used herein, the term "$C_2$-$C_{60}$ alkynylene group" refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms involved in the ring formation, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

As used herein, the term "$C_1$-$C_{10}$ heterocycloalkyl group" refers to a monovalent monocyclic group having 1 to 10 carbon atoms in which at least one N, O, P, Si, Se, Ge, B, S, or any combination thereof, is included as a ring-forming atom. Non-limiting examples of the $C_1$-$C_{10}$ heterocycloalkyl group are a tetrahydrofuranyl group and a tetrahydrothiophenyl group. As used herein, the term "$C_1$-$C_{10}$ heterocycloalkylene group" refers to a divalent group having the same structure as the $C_1$-$C_{10}$ heterocycloalkyl group.

As used herein, the term "$C_3$-$C_{10}$ cycloalkenyl group" refers to a monovalent monocyclic group having 3 to 10 carbon atoms that includes at least one double bond in the ring but does not have aromaticity. Non-limiting examples of the $C_3$-$C_{10}$ cycloalkenyl group are a cyclopentenyl group, a cyclohexenyl group, and a cycloheptenyl group. As used herein, the term "$C_3$-$C_{10}$ cycloalkenylene group" refers to a divalent group having the same structure as the $C_3$-$C_{10}$ cycloalkenyl group.

As used herein, the term "$C_1$-$C_{10}$ heterocycloalkenyl group" refers to a monovalent monocyclic group having 1 to 10 carbon atoms that includes at least one double bond in the ring and in which at least one N, O, P, Si, Se, Ge, B, S, or any combination thereof, is included as a ring-forming atom. Non-limiting examples of the $C_1$-$C_{10}$ heterocycloalkenyl group are a 2,3-hydrofuranyl group and a 2,3-hydrothiophenyl group. As used herein, the term "$C_1$-$C_{10}$ heterocycloalkenylene group" refers to a divalent group having the same structures as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms involved in the ring formation (that is, when substituted with a substituent, the atom not included in the substituent is not counted as the carbon involved in the ring formation), and the term "$C_6$-$C_{60}$ arylene group" as used herein refers to a divalent group having a carbocyclic aromatic system having 6 to 60 carbon atoms. Non-limiting examples of the $C_6$-$C_6$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_6$-$C_{60}$ aryloxy group" as used herein refers to a group represented by -O$A_{103}$ (wherein $A_{103}$ is the $C_6$-$C_{60}$ aryl group). Examples thereof include a 1-naphthyloxy group, a 2-naphthyloxy group, and a 2-azulenyloxy group.

The term "$C_6$-$C_{60}$ arylthio group" as used herein refers to a monovalent group represented by -S$A_{104}$ (wherein $A_{104}$ is the $C_6$-$C_{60}$ aryl group).

The term "$C_1$-$C_{60}$ heteroaryl group" as used herein refers to a monovalent group having a heterocyclic aromatic system that has at least one N, O, Si, P, Se, Ge, B, S, or any combination thereof, as a ring-forming atom, and 1 to 60 carbon atoms. The term "$C_1$-$C_{60}$ heteroarylene group" as used herein refers to a divalent group having a heterocyclic aromatic system that has at least one N, O, Si, P, Se, Ge, B, S, or any combination thereof, as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other.

The term "$C_1$-$C_{60}$ heteroaryloxy group" as used herein refers to a group represented by -O$A_{105}$ (wherein $A_{105}$ is the $C_1$-$C_{60}$ heteroaryl group). Examples thereof include a 2-furanyloxy group, a 2-thienyloxy group, a 2-indolyloxy group, a 3-indolyloxy group, a 2-benzofuriloxy group, and a 2-benzothienyloxy group.

The term "$C_1$-$C_{60}$ heteroarylthio group" as used herein refers to a group represented by -S$A_{106}$ (wherein $A_{106}$ is the $C_1$-$C_{60}$ heteroaryl group).

The term "$C_7$-$C_{60}$ alkylaryl group" as used herein refers to a monovalent group in which an arylene group is substituted with an alkyl group and the sum of the carbon atoms constituting the alkyl group and the aryl group is 7 to 60. Examples of the $C_7$-$C_{60}$ arylalkyl group include a toluene group.

The term "$C_7$-$C_{60}$ arylalkyl group" as used herein refers to a monovalent group in which an alkylene group is substituted with an aryl group and the sum of the carbon atoms constituting the alkyl group and the aryl group is 7 to 60. Examples of the $C_7$-$C_{60}$ arylalkyl group include a benzyl group, a phenylethyl group, a phenylpropyl group, and a naphthylmethyl group.

The term "$C_7$-$C_{60}$ arylalkyloxy group" as used herein refers to a group represented by -O$A_{105}$ (wherein $A_{105}$ is the $C_7$-$C_{60}$ arylalkyl group).

The term "$C_7$-$C_{60}$ arylalkylthio group" as used herein refers to a group represented by -S$A_{106}$ (wherein $A_{106}$ is the $C_7$-$C_{60}$ arylalkyl group).

The term "$C_8$-$C_{60}$ arylalkenyl group" as used herein refers to a monovalent group in which an alkenylene group is substituted with an aryl group and the sum of the carbon atoms constituting the alkenyl group and the aryl group is 8 to 60.

The term "$C_8$-$C_{60}$ arylalkynyl group" as used herein refers to a monovalent group in which an alkynylene group is substituted with an aryl group and the sum of the carbon atoms constituting the alkynyl group and the aryl group is 8 to 60.

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 1 to 60 carbon atoms) having two or more rings condensed to each other, at least one heteroatom selected from N, O, P, Si, Se, Ge, B, or S, other than carbon atoms, as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{30}$ carbocyclic group" as used herein refers to a saturated or unsaturated cyclic group having, as a ring-forming atom, 5 to 30 carbon atoms only. The term "$C_5$-$C_{30}$ carbocyclic group" as used herein refers to a monocyclic group or a polycyclic group, and, according to its chemical structure, a monovalent, divalent, trivalent, tetravalent, pentavalent, or hexavalent group.

The term "$C_1$-$C_{30}$ heterocyclic group" as used herein refers to a saturated or unsaturated cyclic group having, as a ring-forming atom, at least one heteroatom Y, O, Si, P, and S other than 1 to 30 carbon atoms. The term "$C_1$-$C_{30}$ heterocyclic group" as used herein refers to a monocyclic group or a polycyclic group, and, according to its chemical structure, a monovalent, divalent, trivalent, tetravalent, pentavalent, or hexavalent group.

In the present specification, at least one substituent of the substituted $C_5$-$C_{30}$ carbocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be:

deuterium, —F, —Cl, —Br, —I, -$CD_3$, -$CD_2H$, -$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one deuterium, —F, —Cl, —Br, —I, -$CD_3$, -$CD_2H$, -$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, —$B(Q_{16})(Q_{17})$, —$P(=O)(Q_{18})(Q_{19})$, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or any combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with at least one deuterium, —F, —Cl, —Br, —I, -$CD_3$, -$CD_2H$, -$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, —$B(Q_{26})(Q_{27})$, —$P(=O)(Q_{28})(Q_{29})$, or any combination thereof; or —$N(Q_{31})(Q_{32})$, —$Si(Q_{33})(Q_{34})(Q_{35})$, —$B(Q_{36})(Q_{37})$, or —$P(=O)(Q_{38})(Q_{39})$, and $Q_1$ to $Q_9$, $Q_{11}$ to $Q_{19}$, $Q_{21}$ to $Q_{29}$, and $Q_{31}$ to $Q_{39}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with at least one a $C_1$-$C_{60}$ alkyl group, and a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group.

Others

The wording "A to B" used herein refers to a range from A to B, wherein A and B are inclusive.

Although one or more embodiments of the present disclosure has been described above with reference to the accompanying drawings, the present disclosure is not limited to the embodiments. It will be apparent to those skilled in the art that various changes or modifications can be made within the scope of the technical idea described in the claims. It is understood that such various changes and modifications also fall within the technical scope of the present disclosure.

Hereinafter, with reference to Examples and Comparative Examples, a condensed cyclic compound represented by Formula 1 or 2 and an organic light-emitting device including the same will be described in detail. Examples to be described below are presented as examples only, and the condensed cyclic compound and organic light-emitting device according to an example of the present invention are not limited to the examples to be described later.

The wording "'B' was used instead of 'A'" used in describing Synthesis Examples means that a molar equivalent of 'B' was identical to a molar equivalent of 'A'.

The unit "%" is based on a weight unless described otherwise.

EXAMPLES

Synthesis Example 1: Synthesis of Compound 43

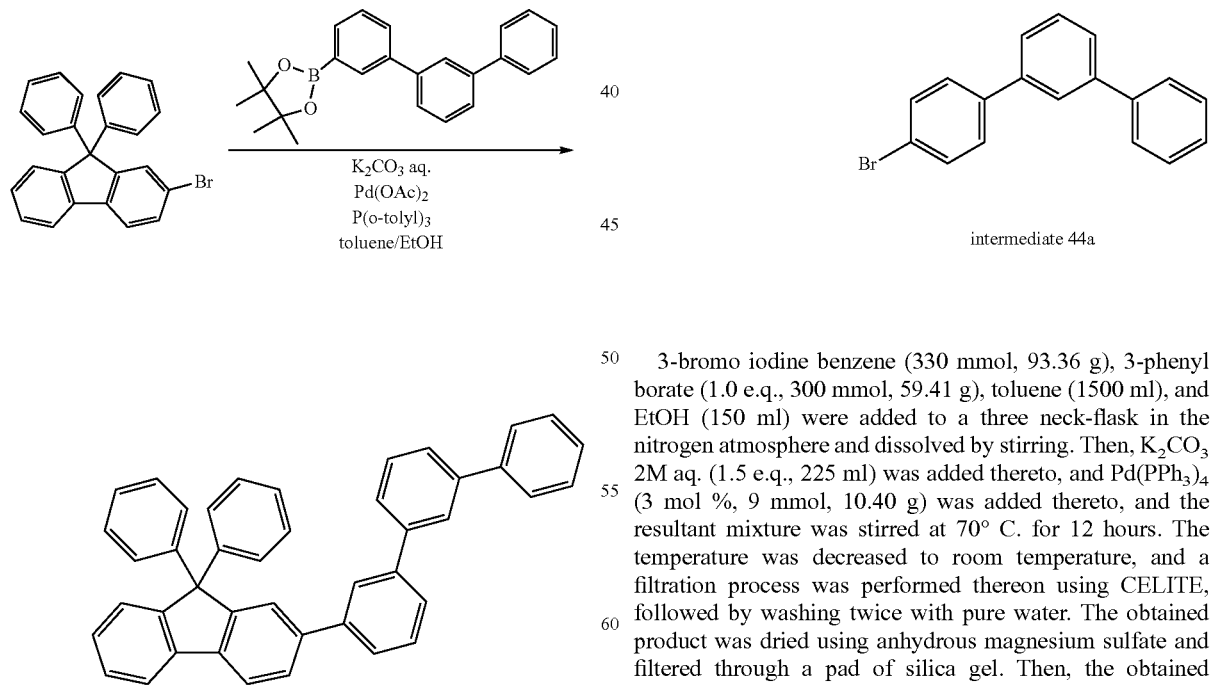

2-bromo-9,9-diphenyl-9H-fluorene (30 mmol, 11.92 g), 2-([1,1': 3',1" terphenyl]-3-yl)-4,4,5,5-tetramethyl-1,3,2-dioxaborolane (31.5 mmol, 11.22 g), toluene (120 ml), and EtOH (30 ml) were added to a three neck-flask in the nitrogen atmosphere and dissolved by stirring. Then, $K_2CO_3$ 2M aq. (1.5 eq., 22.5 ml) was added thereto, and palladium acetate (3 mol %, 0.9 mmol, 202 mg), and o-tolylphosphine (4.5 mol %, 1.35 mmol, 411 mg) were added thereto and the mixture was stirred at 80° C. for 8 hours. After the temperature was decreased to room temperature, the mixture was diluted with toluene (200 ml), filtered using CELITE, and washed three times with pure water. The obtained product was dried using anhydrous magnesium sulfate and filtered through a pad of silica gel. The obtained result was recrystallized twice by using toluene and hexane (5 ml:15 ml/1 g) to obtain a white solid. The amount of Compound 43 was 16.2 g, and the yield thereof was 99%.

Synthesis Example 2: Synthesis of Compound 44

Synthesis of Intermediate 44a

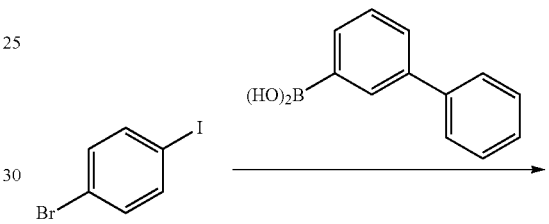

intermediate 44a 3-bromo iodine benzene (330 mmol, 93.36 g), 3-phenyl borate (1.0 e.q., 300 mmol, 59.41 g), toluene (1500 ml), and EtOH (150 ml) were added to a three neck-flask in the nitrogen atmosphere and dissolved by stirring. Then, $K_2CO_3$ 2M aq. (1.5 e.q., 225 ml) was added thereto, and $Pd(PPh_3)_4$ (3 mol %, 9 mmol, 10.40 g) was added thereto, and the resultant mixture was stirred at 70° C. for 12 hours. The temperature was decreased to room temperature, and a filtration process was performed thereon using CELITE, followed by washing twice with pure water. The obtained product was dried using anhydrous magnesium sulfate and filtered through a pad of silica gel. Then, the obtained product was recrystallized twice by using toluene and hexane (the ratio of toluene to hexane was 3 ml:12 ml/1 g) and vacuum-dried (50° C., 12 hours) to obtain the target product of a white solid. The amount of Intermediate 44a was 58.4 g, and the yield thereof was 63%.

Synthesis of Intermediate 44b

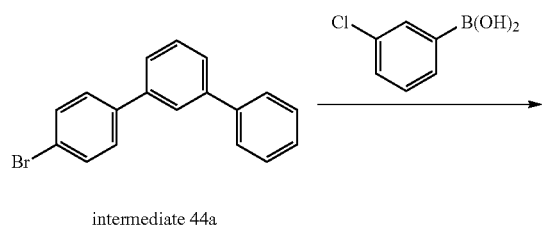

intermediate 44a

Synthesis of Intermediate 44c

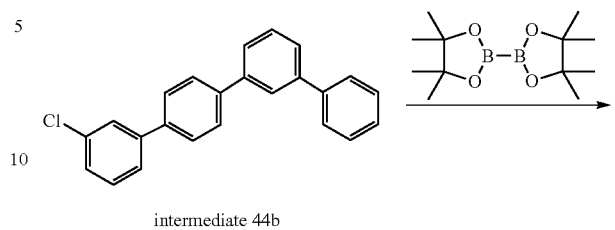

intermediate 44b intermediate 44b intermediate 44c

Intermediate 44a (100 mmol, 30.92 g), 3-chlorophenyl borate (1.1 e.q., 110 mmol, 17.20 g), toluene (200 ml), and EtOH (50 ml) were added to a three neck-flask in the nitrogen atmosphere and then dissolved by stirring. Then, K₂CO₃ 2M aq. (1.5 e.q., 75 ml) was added thereto, and Pd(PPh₃)₄ (3 mol %, 3 mmol, 3.47 g) was added thereto, and the resultant mixture was stirred at 70° C. for 12 hours. After the temperature was decreased to room temperature, the mixture was diluted with toluene (500 ml), filtered using CELITE, and washed twice with pure water. The obtained product was dried using anhydrous magnesium sulfate and filtered through a pad of silica gel. Then, the obtained product was recrystallized once by using toluene and hexane (the ratio of toluene to hexane was 3 ml:12 ml/1 g) and vacuum-dried (50° C., 12 hours) to obtain the target product of a white solid. The amount of Intermediate 44b was 18.75 g, and the yield thereof was 55%.

Intermediate 44b (55 mmol, 18.6 g), pinacolato diboron (1.1 e.q., 60.5 mmol, 15.36 g), potassium acetate (2 e.q., 110 mmol, 10.8 g), and 1,4-dioxane (220 ml) were added to a three neck-flask in the nitrogen atmosphere and dissolved by stirring. Then, palladium acetate (2 mol %, 1.1 mmol, 247 mg), and X-Phos (4 mol %, 2.2 mmol, 1.05 g) were added thereto, and stirred at 100° C. for 12 hours. After the temperature was decreased to room temperature, the mixture was diluted with toluene (300 ml), filtered using CELITE, and washed three times with pure water. The obtained product was dried using anhydrous magnesium sulfate and filtered through a pad of silica gel. Then, the obtained product was recrystallized twice by using hexane (10 ml/1 g) and vacuum-dried (50° C., 12 hours) to obtain the target product of a white solid. The amount of Intermediate 44c was 19.34 g, and the yield thereof was 81%.

Synthesis of Compound 44

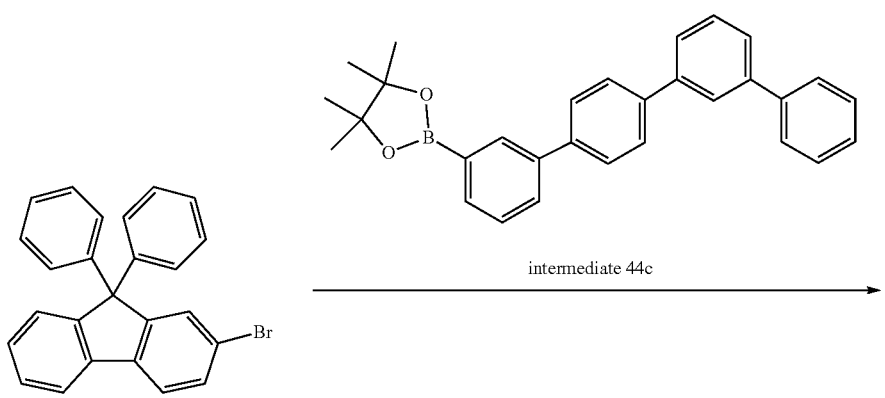

intermediate 44c

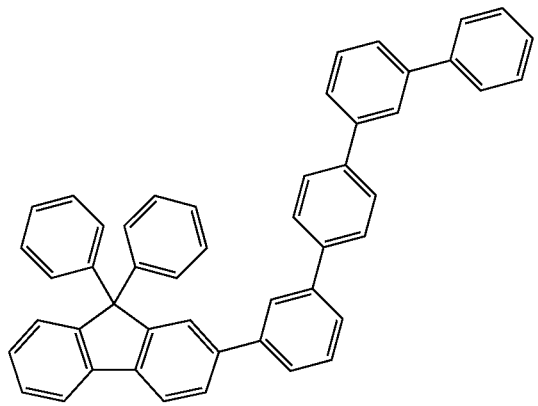

44

Compound 44 was synthesized in the same manner as used to synthesize Compound 43, except that Intermediate 44c was used instead of 2-([1,1':3',1''-terphenyl]-3-yl)-4,4,5,5-tetramethyl-1,3,2-dioxaborolane.

Compounds 43 and 44 obtained above, and Comparative Compounds C1 and C2 described below were prepared as solid samples.

Comparative Compound C1

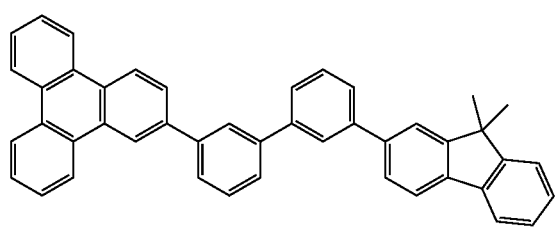

Comparative Compound C2

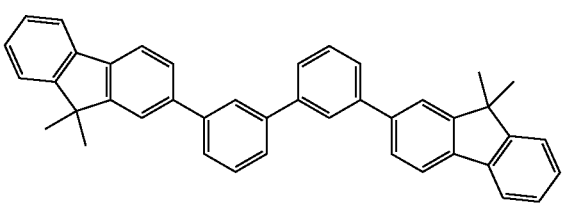

Solubility Evaluation 50 mg of a solid sample was placed in a colorless sample bottle, 500 mg of methyl benzoate was added as a solvent, and ultrasonic irradiation was performed for 20 minutes at room temperature to visually identify whether the sample solid remained. And when there was a residual solid sample, the solvent was added little by little, the ultrasonic irradiation was repeated until the sample solid was completely dissolved, and the solubility was calculated by using the amount of the solvent that was dissolved. The results are shown in Table 1 below.

Evaluation of Pot Life of Solution 50 mg of a solid sample was placed in a colorless sample bottle, 1.0 g of methyl benzoate was added as a solvent, and was completely dissolved by heating at 150° C., thereby producing 5 wt % of the solution. Thereafter, the solution was cooled to room temperature, and the time from when the temperature reaches room temperature to when the precipitation solid, such as crystals, started to be visually identified, was defined as the pot life. In other words, the longer the pot life, crystallization less occurs. The measurement results are shown in Table 1 below. "* 1" indicates that Comparative Compound was not measurable because it was not dissolved.

TABLE 1

| Compound | Solubility in methyl benzoate at room temperature (wt %) | Pot life of 5 wt % of methyl benzoate solution |
|---|---|---|
| Compound 43 | >10 | >300 |
| Compound 44 | >10 | >300 |
| Comparative Compound C1 | 0.1 | *1 |
| Comparative Compound C2 | 0.3 | 0.1 |
| Comparative Compound C3 | >10 | >300 |
| Comparative Compound C4 | >10 | >300 |
| Comparative Compound C5 | 1 | 0.1 |

From Table 1, it can be seen that compared to Comparative Compounds, Compounds 43 and 44 according to the present disclosure has excellent solubility and pot life.

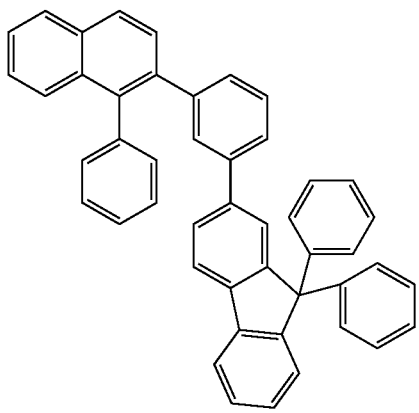

C3

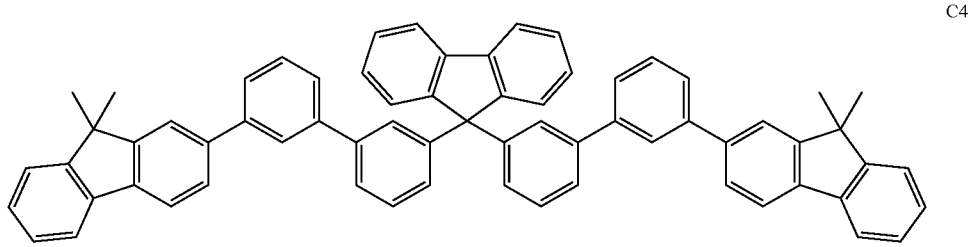

C4

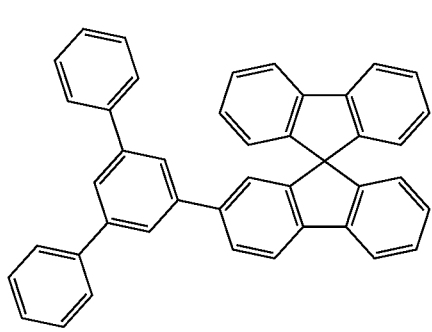

C5

Measurements of HOMO Values and LUMO Values

Compounds 1 and 2 obtained above, and Comparative Compounds C-1 and Cz3 described below were prepared as solid samples. Then, HOMO and LUMO values were measured as follows.

1. Fabrication of Measurement Samples
   (1) A sample solution was prepared such that the amount of a solid sample was 4 wt % with respect to the weight of methyl benzoate as a solvent.
   (2) The sample solution prepared in the above (1) was coated on each of an ITO substrate and a quartz substrate by using a spin coating method to form a coating film having a dry-film thickness of 50 nm. The obtained coating film was heated at 120° C. for 1 hour under a vacuum of $10^{-1}$ Pa or less, and then cooled to room temperature under a vacuum of 10.1 Pa or less to form a thin film layer (thin film sample).

2. Measurement of HOMO Values
   With respect to the thin-film sample on the ITO substrate manufactured in 1. (2), HOMO values were measured by using a photoelectron spectrometer AC-3 (manufactured by Riken Keiki Co., Ltd.) in the atmosphere.

3. Measurement of LUMO Values
   With respect to the thin-film sample on the quartz substrate manufactured in 1. (2), the energy gap value ($E_g$) was measured from the absorption edge of the ultraviolet visible absorption spectrum by using a spectrophotometer U-3900 (manufactured by Hitachi Hi-Tech Science), and the LUMO value was calculated according to Equation 3.

$$LUMO = HOMO + E_g \quad \text{Equation 3}$$

The calculation results are shown in Table 2 below.

Measurement of Glass Transition Temperature ($T_g$)

Compounds 43 and 44 obtained above, and Comparative Compounds $C_1$ and $C_2$ described below were prepared as solid samples. Moreover, the azine ring derivative Az1, the phosphorescent platinum group metal complex TEG, and the Comparative Compound Cz1 to Cz3 which were used for manufacture of an organic light-emitting device to be described later were prepared as sample solids.

Next, the process of scanning measurement using about 5 mg of sample solids was repeated 3 times using the differential scanning calorimetry DSC6220 (made by Seiko Corporation). Here, the conditions for measurements included the temperature increase rate of 10° C./min in the temperature range of −50° C. to 300° C., and the temperature decrease rate of −50° C./min in the temperature range of 300° C. to −50° C. The glass transition temperature ($T_g$) was measured from the second and subsequent scanning calorie curve. The measurement results are shown in Table 2 below.

TABLE 2

| Compound | HOMO (eV) | LUMO (eV) | $T_g$(° C.) |
| --- | --- | --- | --- |
| Compound 43 | −6.2 | −2.7 | 92 |
| Compound 44 | −6.2 | −2.8 | 109 |
| Az1 | −5.9 | −3.0 | 125 |
| TEG | −5.4 | −2.9 | —(No measurement) |
| Comparative Compound Cz1 | −5.6 | −2.3 | 115 |
| Comparative Compound Cz2 | −5.8 | −2.6 | 108 |
| Comparative Compound Cz3 | −6.0 | −3.0 | 95 |

TABLE 2-continued

| Compound | HOMO (eV) | LUMO (eV) | $T_g$(° C.) |
| --- | --- | --- | --- |
| Comparative Compound C1 | −6.1 | −2.8 | 126 |
| Comparative Compound C2 | −6.1 | −2.8 | 120 |
| Comparative Compound C3 | −6.3 | −2.8 | 108 |
| Comparative Compound C4 | −6.2 | −2.6 | 147 |
| Comparative Compound C5 | −6.3 | −2.7 | 121 |

Manufacturing of Organic Light-Emitting Devices

Example 1

First, a glass substrate on which a stripe-shaped indium tin oxide (ITO) (anode) was deposited as a first electrode (anode) was prepared. Poly(3,4-ethylene dioxythiophene)/poly(4-styrenesulfonate) (PEDOT/PSS) (manufactured by Sigma-Aldrich)) was applied on the glass substrate by a spin coat method to form a hole injection layer having a dry-film thickness of 30 nm.

Then, a coating solution was prepared for a hole transport layer, the coating solution including the solvent anisole, 3 parts by weight of a hole transporting polymer (HTP1) (weight average molecular weight Mw=400,000, PDI (Mw/Mn)=2.7) having a repeating unit represented by the following formula with respect to 100 parts by weight of the solvent, and 0.6 parts by weight of low molecular weight compound AD1 with respect to 100 parts by weight of the solvent. Subsequently, the obtained coating solution for a hole transport layer was applied by using a spin coat method to form a coating film having a dry-film thickness of 125 nm. The obtained coating film was heated at 120° C. for 1 hour under a vacuum of $10^{-1}$ Pa or less, and then cooled to room temperature under a vacuum of $10^{-1}$ Pa or less to form a hole transport layer.

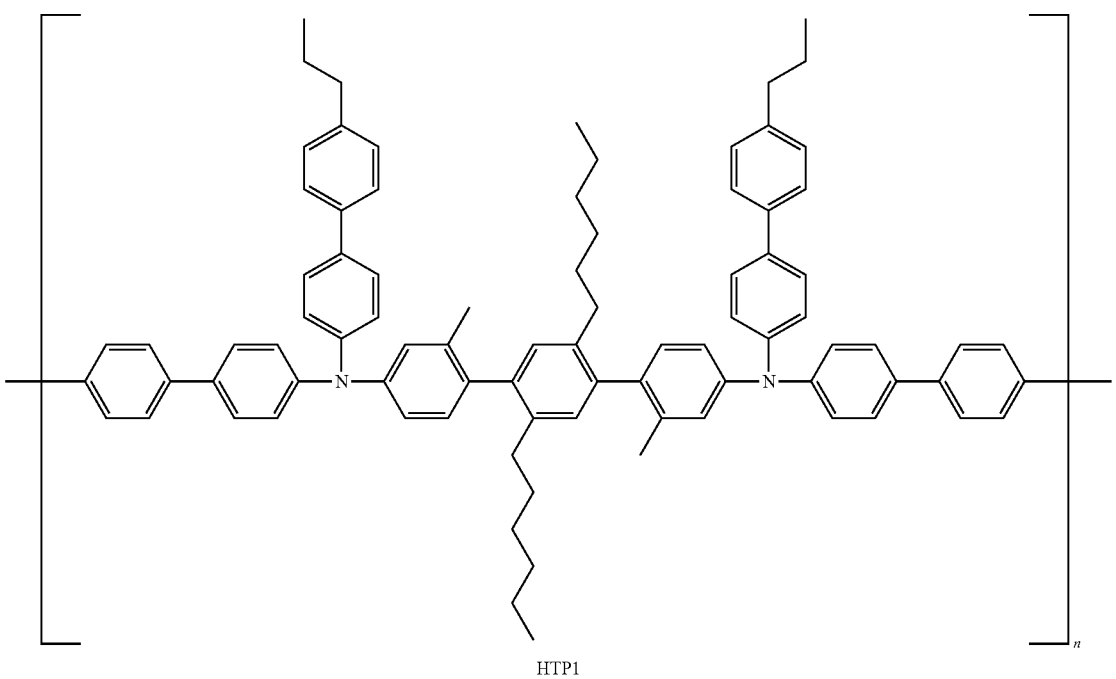

HTP1

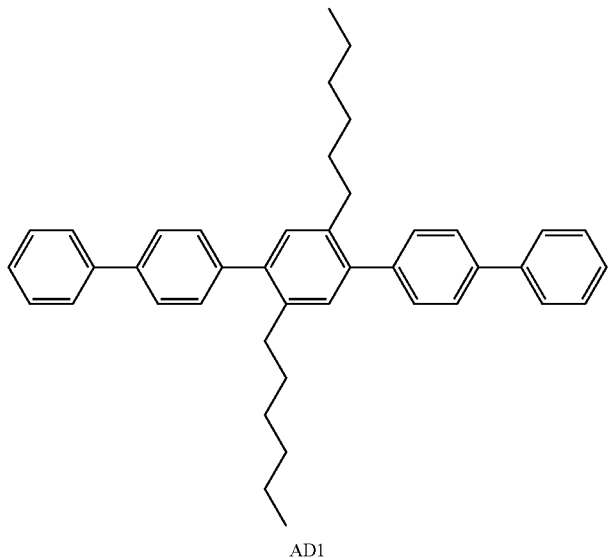

AD1

Subsequently, the ink for an emission layer which is a liquid composition was applied on the hole transport layer to form an emission layer having a dry-film thickness of 50 nm thereon, wherein the ink was a methyl benzoate solution which was a composition including Compound 43 and Compound Az1, which are host materials, and Compound TEG (D1, tris(2-(3-p-xylyl)phenyl)pyridiniridium), which is a dopant material.

The ink for an emission layer was prepared including, with respect to 100 parts by weight of the methyl benzoate, 2.64 parts by weight of Compound 43, 1.32 parts by weight of Az1, and 0.4 parts by weight of TEG.

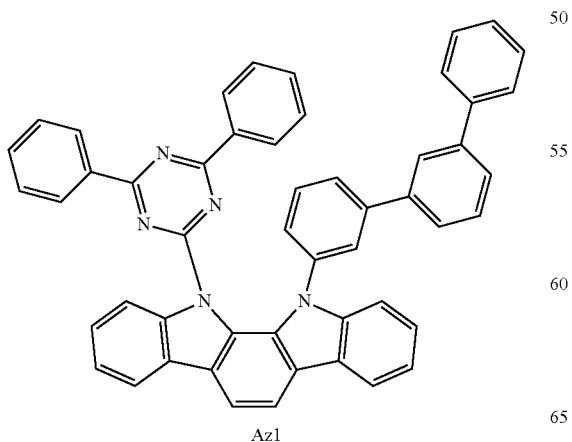

Az1

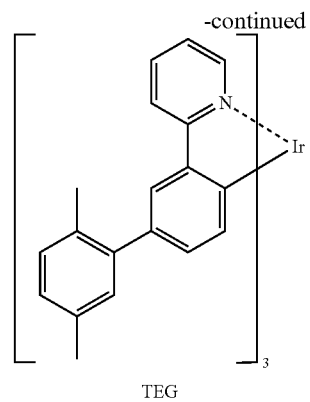

TEG

Then, (8-quinolinolato)lithium (Liq) and KLET-03 (the product of Chemipro Kasei Inc.) were co-deposited at a weight ratio of 2:8 on the emission layer in a vacuum deposition apparatus to form an electron transport layer having a thickness of 30 nm.

Lithium fluoride (LiF) was deposited on the electron transport layer by a vacuum deposition apparatus to form an electron injection layer having a thickness of 1 nm.

Also, aluminum (Al) was deposited on the electron injection layer by a vacuum deposition apparatus, thereby forming a second electrode (cathode) having a thickness of 100 nm.

Then, in a glove box in the nitrogen atmosphere having 1 ppm or less of water concentration and 1 ppm or less of oxygen, a sealing process was performed using a glass sealing tube with a desiccant and a ultraviolet curable resin, thereby obtaining an organic light-emitting device.

Example 2

An organic light-emitting device was manufactured in the same manner as in Example 1, except that, as the host material, Compound 44 was used instead of Compound 43.

Example 3

An organic light-emitting device was manufactured in the same manner as in Example 1, except that the ink composition for the emission layer was changed as follows.

The ink for an emission layer was prepared such that, with respect to 100 parts by weight of methyl benzoate, the solid content contained 1.33 parts by weight of Compound 43, 1.33 parts by weight of Compound Cz1, 1.33 parts by weight of Compound Az1, and 0.4 parts by weight of Compound TEG.

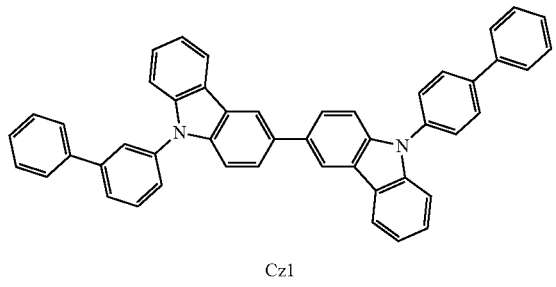 [SMILES: c1ccc(-c2ccc(-n3c4ccccc4c4cc(-c5ccc6c(c5)c5ccccc5n6-c5cccc(-c6ccccc6)c5)ccc43)cc2)cc1]

Cz1

Example 4

An organic light-emitting device was manufactured in the same manner as in Example 3, except that, as the host material, Compound 44 was used instead of Compound 43.

Comparative Examples 1 to 3

An organic light-emitting device was manufactured in the same manner as in Example 1, except that the ink composition for the emission layer was changed as shown in Table 3.

Evaluation of Organic Light-Emitting Devices>

According to the following method, driving voltage, current efficiency and light-emission lifespan (durability) were evaluated.

Using a DC constant voltage power supply (KEYENCE source meter), while the voltage applied to an organic light-emitting device was continuously changed from 0 V to 20 V, the organic light-emitting device was powered to emit light and the luminance thereof was measured by using a luminance measurement apparatus (SR-3 made by Topcom).

Here, the current value per unit area (current density) of the organic light-emitting device was measured, and the luminance ($cd/m^2$) was divided by the current density ($A/m^2$) to calculate the current efficiency (cd/A). In addition, the current efficiency represents the efficiency (conversion efficiency) for converting the current into light emission energy, and the higher the current efficiency, the higher the performance of the organic light emitting device.

In addition, the light-emission lifespan (durability) was represented as "LT80 (h)," which is the time corresponding to 80% of the initial luminance, wherein the luminance was decreased during the continuous operation at the current of 6,000 $cd/m^2$.

The evaluation results are shown in Table 3 below. In Table 3, the current efficiency is expressed as a relative value with respect to the current efficiency of the organic light-emitting device of Comparative Example 1, wherein the current efficiency of the organic light-emitting device of Comparative Example 1 was set to 100. In addition, the light-emission lifespan (durability) is expressed as a relative value with respect to the device lifespan (LT80 (h)) of the organic light-emitting device of Comparative Example 1, wherein the device lifespan ($LT_{80}$ (h)) of the organic light-emitting device of Comparative Example 1 was set to 100.

TABLE 3

| | Composition of emission layer | Driving voltage (V) @1,000 ($cd/m^2$) | Current efficiency (Relative value) @1,000 ($cd/m^2$) | Light-emission lifespan (Relative value) @6,000 ($cd/m^2$) |
| --- | --- | --- | --- | --- |
| Example 1 | Compound 43:Az1:TEG (66:33:10) | 6.1 | 138 | 325 |
| Example 2 | Compound 44:Az1:TEG (66:33:10) | 6.0 | 140 | 360 |
| Example 3 | Compound 43:Cz1:Az1:TEG (33:33:33:10) | 5.2 | 116 | 240 |
| Example 4 | Compound 44:Cz1:Az1:TEG (33:33:33:10) | 5.0 | 122 | 260 |
| Comparative Example 1 | Cz1:Az1:TEG (66:33:10) | 5.5 | 100 | 100 |
| Comparative Example 2 | Cz2:Az1:TEG (66:33:10) | 7.5 | 98 | 45 |
| Comparative Example 3 | Cz3:Az1:TEG (66:33:10) | 6.2 | 111 | 170 |
| Comparative Example 4 | C1:Az1:TEG (66:33:10) | Impossible to manufacture devices since a film could not be formed by coating | | |
| Comparative Example 5 | C2:Az1:TEG (66:33:10) | Impossible to manufacture devices since a film could not be formed by coating | | |
| Comparative Example 6 | C3:Az1:TEG (66:33:10) | 6.7 | 73 | 40 |

TABLE 3-continued

| | Composition of emission layer | Driving voltage (V) @1,000 (cd/m$^2$) | Current efficiency (Relative value) @1,000 (cd/m$^2$) | Light-emission lifespan (Relative value) @6,000 (cd/m$^2$) |
|---|---|---|---|---|
| Comparative Example 7 | C4:Az1:TEG (66:33:10) | 5.9 | 90 | 120 |
| Comparative Example 8 | C5:Az1:TEG (66:33:10) | Impossible to manufacture devices since a film could not be formed by coating | | |

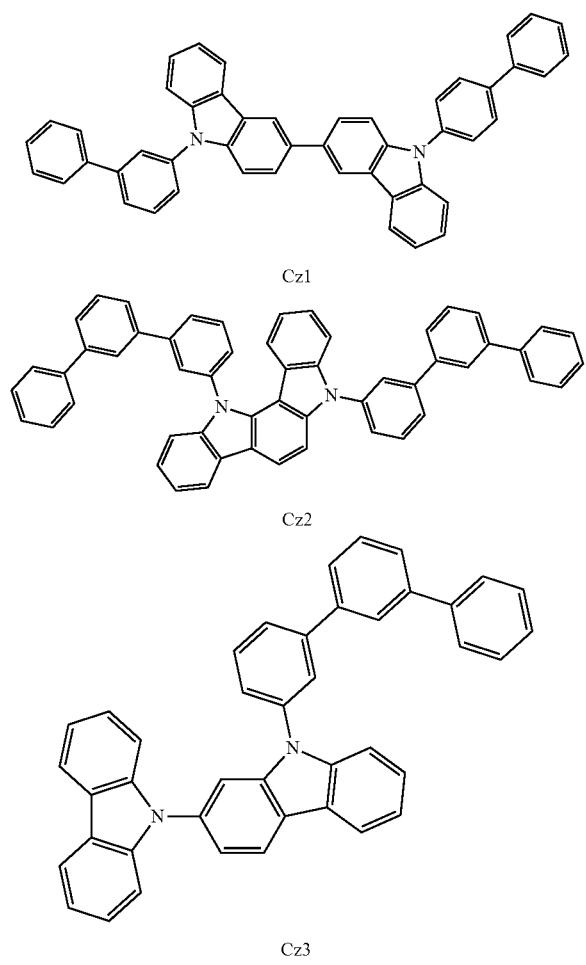

Cz1

Cz2

Cz3

From the results in Table 3, it can be seen that Examples 1 and 2 using a condensed cyclic compound represented by Formula 1 as a host together with an azine ring derivative Az1 showed higher luminescent efficiency and longer light-emission lifespan than Comparative Examples 1 to 3 using a carbazole derivative, which is a commonly used hole transport capability host material.

In addition, in the case of C1, C2 and C5, each having a relatively short pot life, it is difficult to manufacture a light-emitting device by the solution process (Comparative Example 4, Comparative Example 5 and Comparative Example 8).

In addition, in the case of Comparative Example 6 using C3 containing an ortho-phenyl group as a host and Comparative Example 7 using C4 containing a fluorene group connected at the 9$^{th}$ position as a host, light-emitting devices could be manufactured, although a light-emitting device could be manufactured but the current efficiency and the light-emission lifespan thereof were not substantially better than Examples.

In addition, by including the compound represented by Formula 1 and the compound containing a carbazole-based moiety (Examples 3 and 4), the driving voltage as well as the luminescent efficiency were improved and the driving voltage was significantly lowered and the power consumption is decreased.

As mentioned above, although the synthesis examples and the examples were described with respect to the present disclosure, the present disclosure is not limited to a specific example, and may be various modified within the scope of the disclosure as described in the claims.

The condensed cyclic compound may have a low glass transition temperature and thus have high solubility, thereby increasing the pot life of the solution including the condensed cyclic compound, and thus may be suitable for use in a solution coating method.

In detail, an organic light-emitting device including the condensed cyclic compound may have high luminescent efficiency and a long lifespan.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A condensed cyclic compound represented by Formula 1 below:

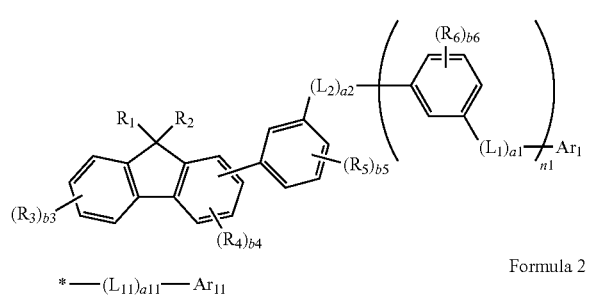

Formula 1

Formula 2 wherein a moiety represented by
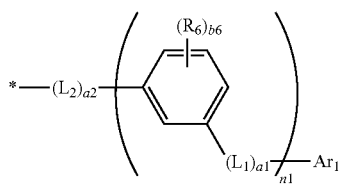
is a group represented by one of Formulae 5-1 to 5-22:
5-1
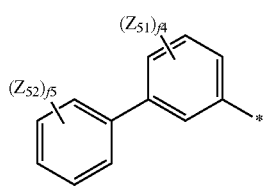
5-2
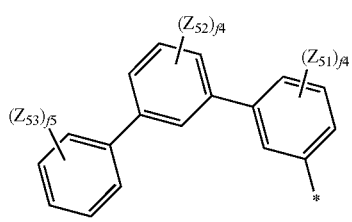
5-3
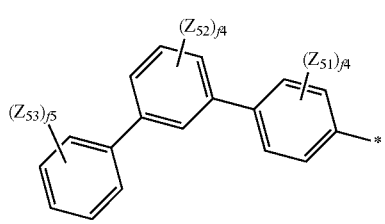
5-4
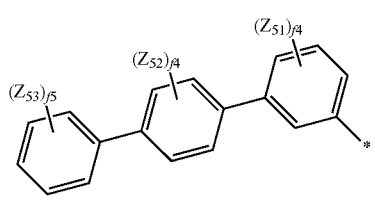
5-5
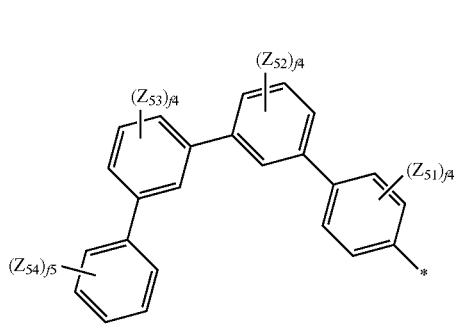
5-6
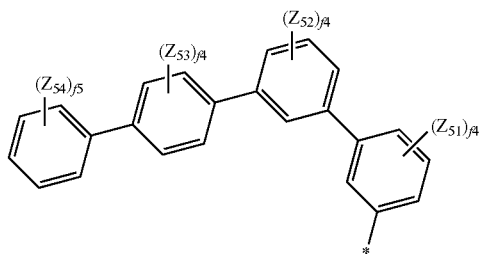
5-7
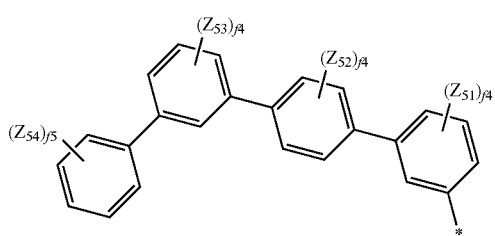
5-8
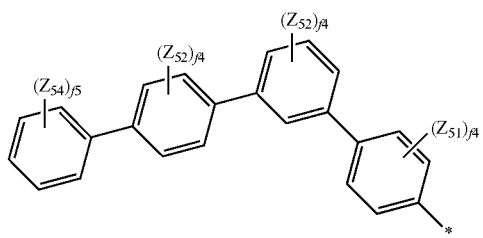
5-9
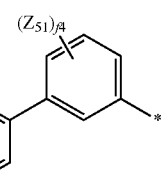
5-10
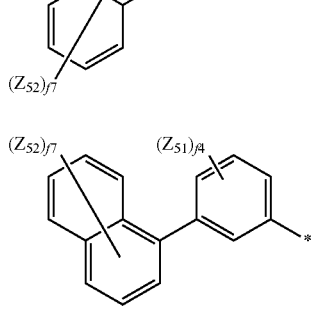
5-11
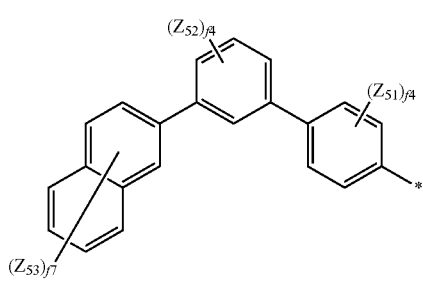

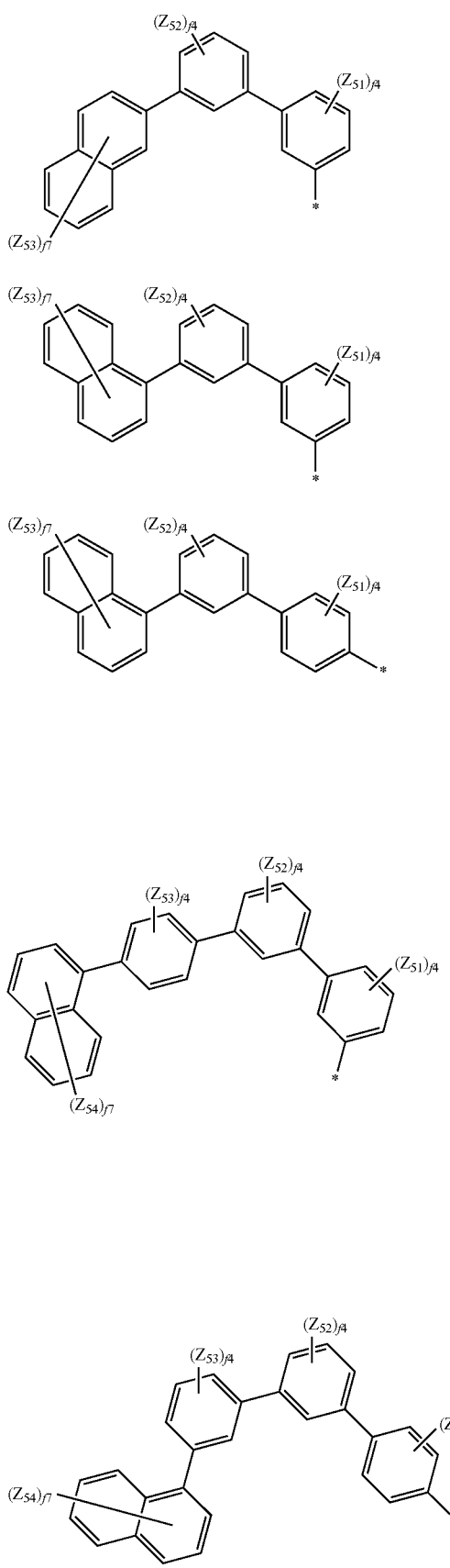

-continued 5-22

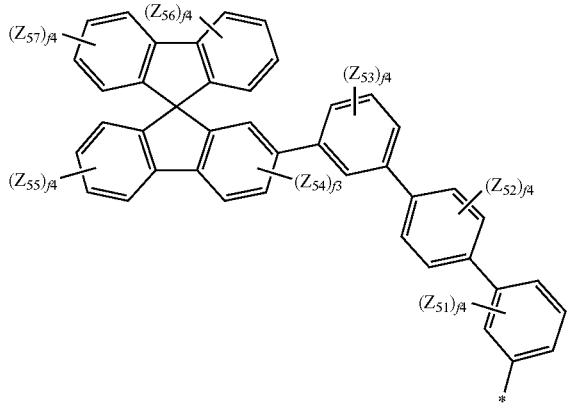

wherein, in Formulae 5-1 to 5-22,
$Y_{51}$ is $C(Z_{58})(Z_{59})$,
$Z_{51}$ to $Z_{59}$ are each independently hydrogen, deuterium, —F, —Cl, —Br, —I, a hydroxyl group, a $C_1$-$C_{20}$ alkyl group, a $C_1$-$C_{20}$ alkoxy group, a phenyl group, or —Si$(Q_{31})(Q_{32})(Q_{33})$,
provided that when the moiety represented by

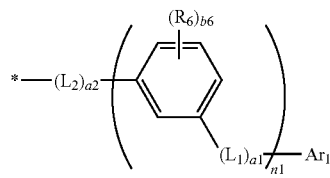

is a group represented by Formula 5-1 and f5 is 1, then $Z_{52}$ is hydrogen, deuterium, —F, a hydroxyl group, a $C_1$-$C_{20}$ alkyl group, a $C_1$-$C_{20}$ alkoxy group, a phenyl group, or —Si$(Q_{31})(Q_{32})(Q_{33})$,
f3 is an integer from 0 to 3,
f4 is an integer from 0 to 4,
f5 is an integer from 0 to 5,
f7 is an integer from 0 to 7,
$Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and
* indicates a binding site to a neighboring atom,
wherein in Formulae 1 and 2,
$L_{11}$ is a single bond, a substituted or unsubstituted $C_5$-$C_{60}$ carbocyclic group, or a substituted or unsubstituted $C_1$-$C_{60}$ heterocyclic group,
a11 is an integer from 1 to 5,
$Ar_{11}$ is a substituted or unsubstituted $C_5$-$C_{60}$ carbocyclic group,
$R_1$ to $R_5$ are each independently a group represented by Formula 2, hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_7$-$C_{60}$ arylalkyl group, a substituted or unsubstituted $C_7$-$C_{60}$ arylalkyloxy group, a substituted or unsubstituted $C_7$-$C_{60}$ arylalkylthio group, a substituted or unsubstituted $C_5$-$C_{60}$ arylalkenyl group, a substituted or unsubstituted $C_5$-$C_{60}$ arylalkynyl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —N$(Q_1)(Q_2)$, provided that $R_3$ and $R_5$ are each not a substituted or unsubstituted $C_6$-$C_{60}$ aryl group or a substituted or unsubstituted $C_1$-$C_{60}$ heteroaryl group,
b3 and b5 are each independently an integer from 0 to 4,
b4 is an integer from 0 to 3,
two adjacent groups of $R_1$, $R_2$, $R_4$(s) in the number of b4, and $R_5$(s) in the number of b5 are optionally linked to form a substituted or unsubstituted $C_5$-$C_{30}$ carbocyclic group or a substituted or unsubstituted $C_1$-$C_{30}$ heterocyclic group,
two adjacent groups of $R_3$(s) in the number of b3 are optionally linked to form a substituted or unsubstituted $C_1$-$C_{30}$ heterocyclic group,
provided that when $R_1$ and $R_2$ are linked to form a substituted or unsubstituted $C_5$-$C_{30}$ carbocyclic group or a substituted or unsubstituted $C_1$-$C_{30}$ heterocyclic group, then the condensed cyclic compound is represented by one of Formulae 1-3 and 1-4:

Formula 1-3

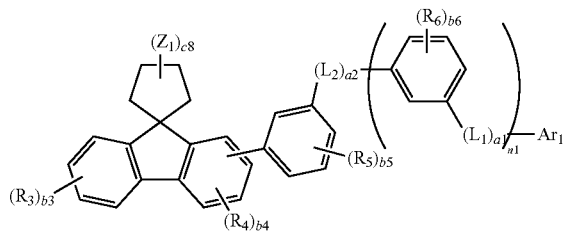

Formula 1-4

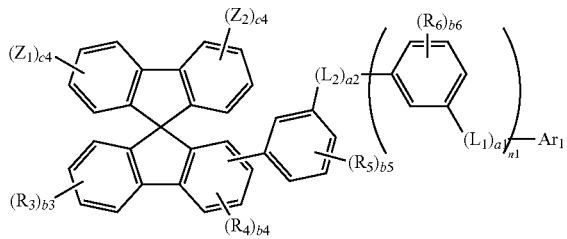

wherein, in Formulae 1-3 and 1-4,
$Z_1$ and $Z_2$ are each independently hydrogen, deuterium, —F, —Cl, —Br, —I, a hydroxyl group, a cyano group, a $C_1$-$C_{20}$ alkyl group, a $C_1$-$C_{20}$ alkoxy group, a phenyl group, or —Si$(Q_{31})(Q_{32})(Q_{33})$,
c4 is an integer from 0 to 4,
at least one substituent of the substituted $C_5$-$C_{60}$ carbocyclic group, the substituted $C_1$-$C_{60}$ heterocyclic group, the substituted $C_1$-$C_{30}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_7$-$C_{60}$ alkylaryl group, the substituted $C_7$-$C_{60}$ arylalkyl group, the substituted $C_7$-$C_{60}$ arylalkyloxy group, the substituted $C_7$-$C_{60}$ arylalkylthio group, the substituted $C_5$-$C_{60}$ arylalkenyl group, the substituted $C_5$-$C_{60}$ arylalkynyl group, the substituted $C_6$-$C_{60}$ aryloxy group, the substituted $C_6$-$C_{60}$ arylthio group, the substituted $C_1$-$C_{60}$ heteroaryl group, the substituted $C_2$-$C_{60}$ alkylheteroaryl group, the substituted $C_1$-$C_{60}$ heteroaryloxy group, the substituted $C_1$-$C_{60}$ heteroarylthio group, the substituted monovalent non-aromatic condensed polycyclic group, and the substituted monovalent non-aromatic condensed heteropolycyclic group is:

deuterium, —F, —Cl, —Br, —I, -$CD_3$, -$CD_2H$, -$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, -$CD_3$, -$CD_2H$, -$CDH_2$, —$CF_3$, —$CF_2H$, —$CFH_2$, —NCS, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, $Si(Q_{11})(Q_{12})(Q_{13})$, —$N(Q_{11})(Q_{12})$, —$C(=O)(Q_{11})$, or any combination thereof;

a $C_3$-$C_{10}$ cycloalkyl group, a $C_1$-$C_{10}$ heterocycloalkyl group, a $C_3$-$C_{10}$ cycloalkenyl group, or a $C_1$-$C_{10}$ heterocycloalkenyl group;

a $C_3$-$C_{10}$ cycloalkyl group, a $C_1$-$C_{10}$ heterocycloalkyl group, a $C_3$-$C_{10}$ cycloalkenyl group, or a $C_1$-$C_{10}$ heterocycloalkenyl group, each substituted with at least one deuterium, —F, —Cl, —Br, —I, -$CD_3$, -$CD_2H$, -$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, —$Si(Q_{21})(Q_{22})(Q_{23})$, —$N(Q_{21})(Q_{22})$, —$C(=O)(Q_{21})$, or any combination thereof, or —$Si(Q_{31})(Q_{32})(Q_{33})$, —$N(Q_{31})(Q_{32})$, or —$C(=O)(Q_{31})$, wherein $Q_1$ to $Q_3$, $Q_{11}$ to $Q_{13}$, $Q_{21}$ to $Q_{23}$, and $Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and

* indicates a binding site to a neighboring atom.

2. The condensed cyclic compound of claim 1, wherein $L_{11}$ is a single bond, a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphenyl group, a hexaphenyl group, a hexacene group, a rubicene group, a trinaphthalene group, a heptaphenyl group, a pyranthrene group, a pyridine group, a pyrazine group, a pyridazine group, a pyrimidine group, a triazine group, a quinoline group, an isoquinoline group, a quinoxaline group, a quinazoline group, a naphthyridine group, an acridine group, a phenazine group, a benzoquinoline group, a benzoisoquinoline group, a phenanthridine group, a phenanthroline group, a benzoquinone group, a coumarin group, an anthraquinone group, a fluorenone group, a furan group, a thiene group, a silole group, a benzofuran group, a benzothien group, a benzosilole group, a dibenzofuran group, a dibenzothiophene group, a dibenzosilole group, a pyrrole group, an indole group, an isoindole group, a carbazole group, a benzocarbazole group, a dibenzocarbazole group, an imidazole group, a benzimidazole group, a pyrazole group, a triazole group, a tetrazole group, an indazole group, an oxazole group, an isoxazole group, a benzoxazole group, a benzisoxazole group, a thiazole group, an isothiazole group, a benzothiazole group, a benzisothiazole group, an imidazopyridine group, an imidazopyrimidine group, an imidazophenanthridine group, a benzimidazophenanthridine group, an azadibenzofuran group, an azacarbazole group, an azadibenzothien group, a diazadibenzofuran group, a diazacarbazole group, a diazadibenzothien group, a xanthonene group, or a thioxanthone group; or a benzene group, a pentalene group, an indene group, a naphthalene group, an anthracene group, an azulene group, a heptalene group, an acenaphthalene group, a phenalene group, a fluorene group, a spiro-bifluorene group, a benzofluorene group, a dibenzofluorene group, a phenanthrene group, a biphenyl group, a terphenyl group, a triphenylene group, a fluoranthene group, a pyrene group, a chrysene group, a picene group, a perylene group, a pentaphene group, a pentacene group, a tetraphenyl group, a hexaphenyl group, a hexacene group, a rubicene group, a trinaphthalene group, a heptaphenyl group, a pyranthrene group, a pyridine group, a pyrazine group, a pyridazine group, a pyrimidine group, a triazine group, a quinoline group, an isoquinoline group, a quinoxaline group, a quinazoline group, a naphthyridine group, an acridine group, a phenazine group, a benzoquinoline group, a benzoisoquinoline group, a phenanthridine group, a phenanthroline group, a benzoquinone group, a coumarin group, an anthraquinone group, a fluorenone group, a furan group, a thiene group, a silole group, a benzofuran group, a benzothien group, a benzosilole group, a dibenzofuran group, a dibenzothiophene group, a dibenzosilole group, a pyrrole group, an indole group, an isoindole group, a carbazole group, a benzocarbazole group, a dibenzocarbazole group, an imidazole group, a benzimidazole group, a pyrazole group, a triazole group, a tetrazole group, an indazole group, an oxazole group, an isoxazole group, a benzoxazole group, a benzisoxazole group, a thiazole group, an isothiazole group, a benzothiazole group, a benzisothiazole group, an imidazopyridine group, an imidazopyrimidine group, an imidazophenanthridine group, a benzimidazophenanthridine group, an azadibenzofuran group, an azacarbazole group, an azadibenzothien group, a diazadibenzofuran group, a diazacarbazole group, a diazadibenzothien group, a xanthonene group, and a thioxanthone group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a triphenylenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, a pyridinyl group, a pyrazinyl group, a pyridazinyl group, a pyrimidinyl group, a triazinyl group, a quinolinyl group, an isoquinolinyl group, a quinoxalinyl group, a quinazolinyl group, a naphthyridinyl group, an acridinyl group, a phenazinyl group, a benzoquinolinyl group, a benzoisoquinolinyl group, a phenanthridinyl group, a phenanthrolinyl group, a benzoquinonyl group, a cumarinyl group, an anthraquinonyl group, a fluorenonyl group, a furanyl group, a thienyl group, a silolyl group, a benzofuranyl group, a benzothienyl group, a benzosilolyl group, a dibenzofuranyl group, a dibenzothiophenyl group, a dibenzosilolyl group, a pyrrolyl group, an indolyl group, an isoindolyl group, a carbazolyl group, a benzocarbazolyl group, a dibenzocarbazolyl group, an imidazolyl group, a benzimidazolyl group, a pyrazolyl group, a triazolyl group, a tetrazolyl group, an indazolyl group, an oxazolyl group, an isoxazolyl group, a benzoxazolyl group, a benzisoxazolyl group, a thiazolyl group, an isothiazolyl group, a benzothiazolyl group, a benzisothiazolyl group, an imidazopyridinyl group, an imidazopyrimidinyl group, an imidazophenanthridinyl group, a benzimidazophenanthridinyl group, an azadibenzofuranyl group, an azacarbazolyl group, an azadibenzothienyl group, a diazadibenzofuranyl group, a diazacarbazolyl group, a diazadibenzothienyl group, a xanthonenyl group, a thioxanthonyl group, or any combination thereof.

3. The condensed cyclic compound of claim 1, wherein $L_{11}$ is: a single bond, a benzene group, a biphenyl group, a terphenyl group, or a tetraphenyl group; or
a benzene group, a biphenyl group, a terphenyl group, or a tetraphenyl group, each substituted with at least one deuterium, —F, —Cl, —Br, —I, a hydroxyl group, a cyano group, a nitro group, an amino group, an amidino group, a hydrazine group, a hydrazone group, a $C_1$-$C_{30}$ alkyl group, a $C_1$-$C_{30}$ alkoxy group, a phenyl group, a biphenyl group, a terphenyl group, or any combination thereof.

4. The condensed cyclic compound of claim 1, wherein $L_{11}$ is a single bond or a group represented by Formulae 3-1 to 3-7 below:

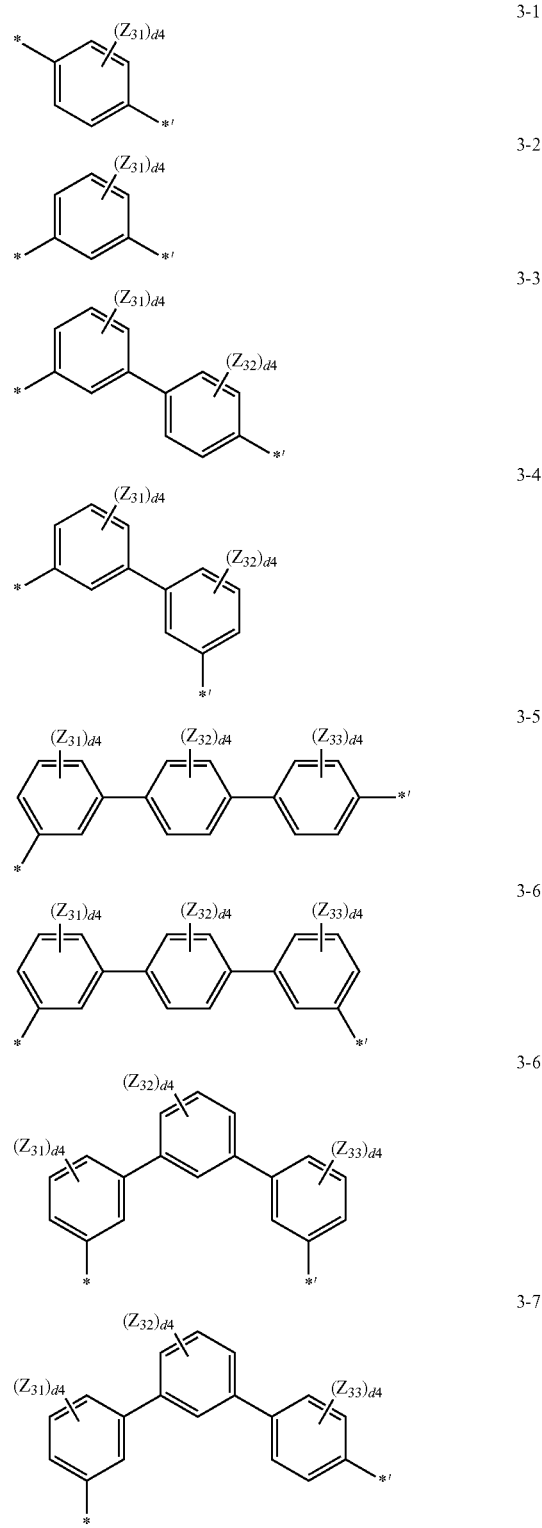

wherein in Formulae 3-1 to 3-7,
$Z_{31}$ to $Z_{33}$ are each independently hydrogen, deuterium, —F, —Cl, —Br, —I, a hydroxyl group, a cyano group, a C$_1$-C$_{20}$ alkyl group, a C$_1$-C$_{20}$ alkoxy group, a cyclopentyl group, a cyclohexyl group, a cycloheptyl group, a cyclopentenyl group, a cyclohexenyl group, or —Si(Q$_{31}$)(Q$_{32}$)(Q$_{33}$), d4 is an integer from 0 to 4, Q$_{31}$ to Q$_{33}$ are each independently hydrogen, deuterium, a C$_1$-C$_{20}$ alkyl group, a C$_1$-C$_{20}$ alkoxy group, a phenyl group, or a biphenyl group, and

* and *' each indicate a binding site to a neighboring atom.

5. The condensed cyclic compound of claim 1, wherein Ar$_{11}$ is:

a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, or a pyranthrenyl group; or a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, or a pyranthrenyl group, each substituted with at least one deuterium, —F, —Cl, —Br, —I, a hydroxyl group, a cyano group, a nitro group, an amino group, an amidino group, a hydrazine group, a hydrazone group, a C$_1$-C$_{30}$ alkyl group, a C$_1$-C$_{30}$ alkoxy group, a phenyl group, a pentalenyl group, an indenyl group, a naphthyl group, an anthracenyl group, an azulenyl group, a heptalenyl group, an acenaphthyl group, a phenalenyl group, a fluorenyl group, a spiro-bifluorenyl group, a benzofluorenyl group, a dibenzofluorenyl group, a phenanthrenyl group, a biphenyl group, a terphenyl group, a fluoranthenyl group, a pyrenyl group, a chrysenyl group, a picenyl group, a perylenyl group, a pentaphenyl group, a pentacenyl group, a tetraphenyl group, a hexaphenyl group, a hexacenyl group, a rubicenyl group, a trinaphthyl group, a heptaphenyl group, a pyranthrenyl group, or any combination thereof.

6. The condensed cyclic compound of claim 1, wherein Ar$_{11}$ is: a phenyl group, a naphthyl group, a fluorenyl group, a spiro-bifluorenyl group, a biphenyl group, a terphenyl group, or a tetraphenyl group; or a phenyl group, a naphthyl group, a fluorenyl group, a spiro-bifluorenyl group, a biphenyl group, a terphenyl group, or a tetraphenyl group, each substituted with at least one deuterium, —F, —Cl, —Br, —I, a hydroxyl group, a cyano group, a nitro group, an amino group, an amidino group, a hydrazine group, a hydrazone group, a C$_1$-C$_{30}$ alkyl group, a C$_1$-C$_{30}$ alkoxy group, a phenyl group, a biphenyl group, a terphenyl group, or any combination thereof.

7. The condensed cyclic compound of claim 1, wherein Ar$_{11}$ is a group represented by Formulae 4-1 to 4-9 below:

4-1
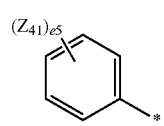

4-2
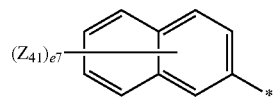

4-3
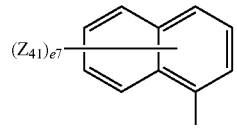

4-4
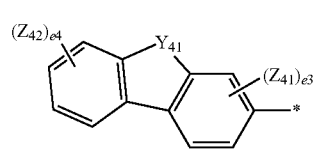

4-5
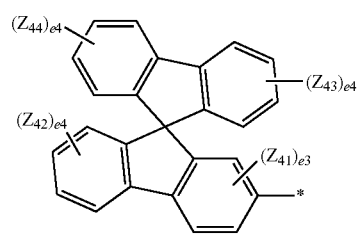

4-6
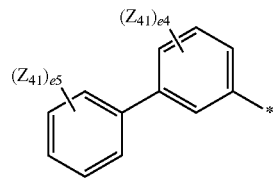

4-7
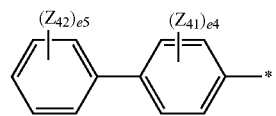

4-8
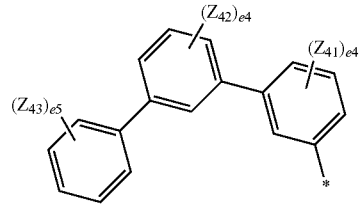

4-9
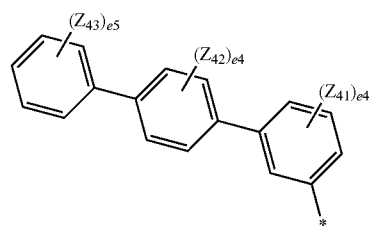

wherein, in Formulae 4-1 to 4-9, $Y_{41}$ is $C(Z_{45})(Z_{46})$, $Z_{41}$ to $Z_{46}$ are each independently hydrogen, deuterium, —F, —Cl, —Br, —I, a hydroxyl group, a cyano group, a $C_1$-$C_{20}$ alkyl group, a $C_1$-$C_{20}$ alkoxy group, a phenyl group, or —Si($Q_{31}$)($Q_{32}$)($Q_{33}$), e3 is an integer from 0 to 3, e4 is an integer from 0 to 4, e5 is an integer from 0 to 5, e7 is an integer from 0 to 7, $Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group, and

* indicates a binding site to a neighboring atom.

8. The condensed cyclic compound of claim 1, wherein $R_1$, $R_2$, and $R_4$ are each independently:

hydrogen, deuterium, —F, —Cl, —Br, —I, a cyano group, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, or a naphthyl group;

a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, or a naphthyl group, each substituted with at least one deuterium, —F, —Cl, —Br, —I, a cyano group, a phenyl group, a biphenyl group, a terphenyl group, or any combination thereof;

$R_3$ and $R_5$ are each independently:

hydrogen, deuterium, —F, —Cl, —Br, —I, a cyano group, a $C_1$-$C_{20}$ alkyl group, a $C_2$-$C_{20}$ alkenyl group, a $C_2$-$C_{20}$ alkynyl group, or a $C_1$-$C_{20}$ alkoxy group;

a $C_1$-$C_{20}$ alkyl group, a $C_2$-$C_{20}$ alkenyl group, a $C_2$-$C_{20}$ alkynyl group, a $C_1$-$C_{20}$ alkoxy group, each substituted with at least one deuterium, —F, —Cl, —Br, —I, a cyano group, a phenyl group, a biphenyl group, a terphenyl group, or any combination thereof.

9. The condensed cyclic compound of claim 1, wherein the condensed cyclic compound is a group represented by Formula 1A below:

Formula 1A

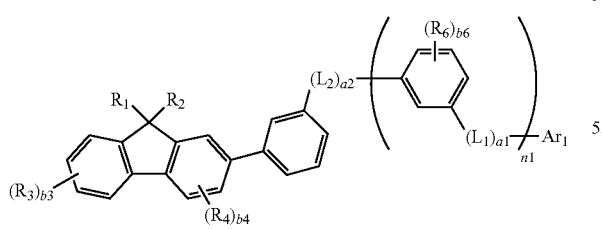

wherein, in Formula 1A, $L_1$, $L_2$, a1, a2, $Ar_1$, $R_1$ to $R_6$, b3 to b6, and n1 are each understood by referring to the description provided in connection with claim 1.

10. The condensed cyclic compound of claim 1, wherein the condensed cyclic compound is represented by one of Formulae 1-1 to 1-8:

Formula 1-1

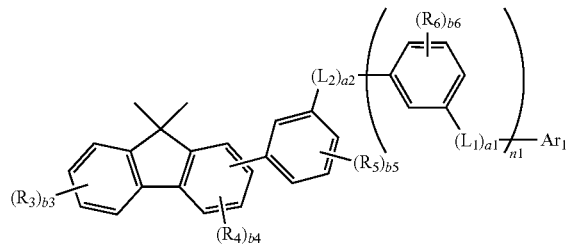

Formula 1-2

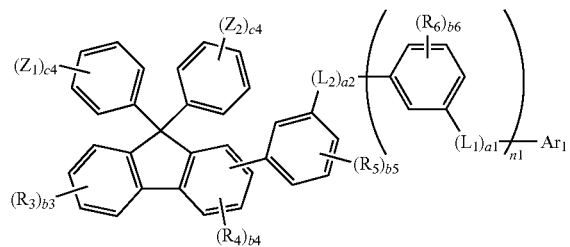

Formula 1-3

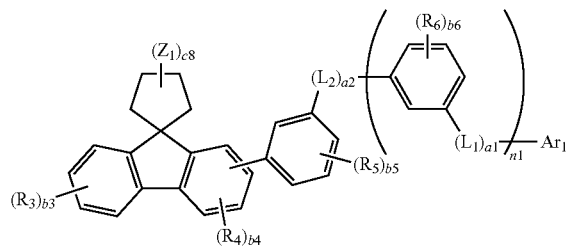

Formula 1-4

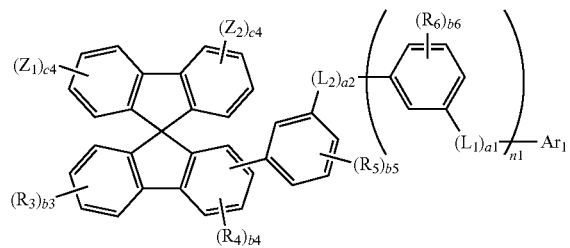

Formula 1-5

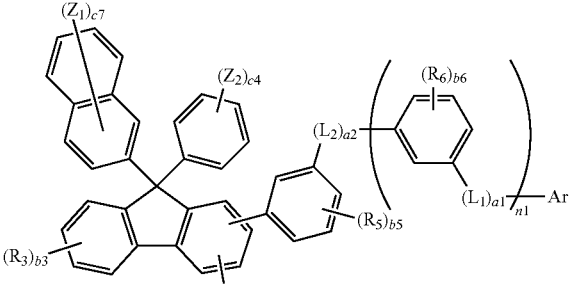

-continued

Formula 1-6
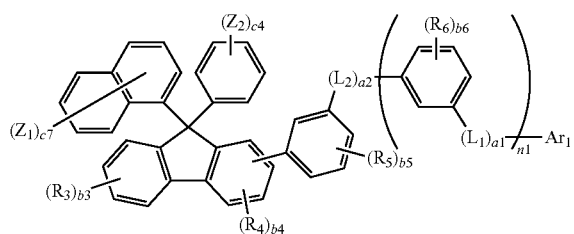

Formula 1-7
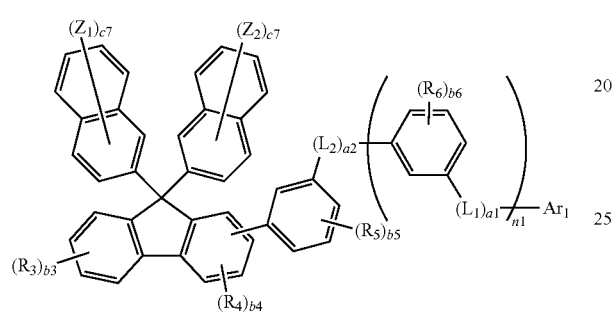

Formula 1-8
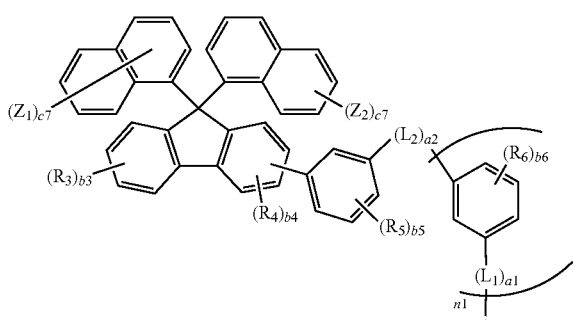

wherein, in Formulae 1-1 to 1-8, $L_1$, $L_2$, a1, a2, $Ar_1$, $R_3$ to $R_6$, b3 to b6, and n1 are each understood by referring to the description provided in connection with claim 1, $Z_1$ and $Z_2$ are each independently hydrogen, deuterium, —F, —Cl, —Br, —I, a hydroxyl group, a cyano group, a $C_1$-$C_{20}$ alkyl group, a $C_1$-$C_{20}$ alkoxy group, a phenyl group, or —Si($Q_{31}$)($Q_{32}$)($Q_{33}$), c4 is an integer from 0 to 4, c7 is an integer from 0 to 7, c8 is an integer from 0 to 8, and $Q_{31}$ to $Q_{33}$ are each independently hydrogen, deuterium, a $C_1$-$C_{20}$ alkyl group, a $C_1$-$C_{20}$ alkoxy group, a phenyl group, or a biphenyl group.

11. The condensed cyclic compound of claim 1, wherein the condensed cyclic compound does not comprise an ortho-phenyl group.

12. The condensed cyclic compound of claim 1, wherein the condensed-cyclic compound is one of Compounds 1 to 60:

1

2
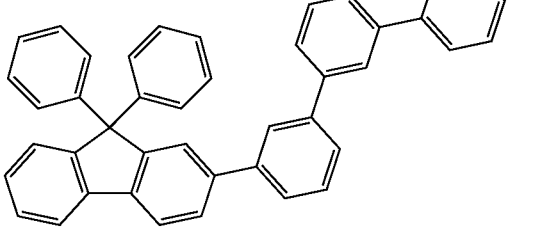

3
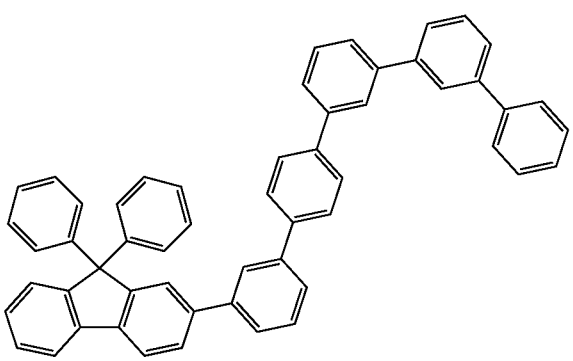

4
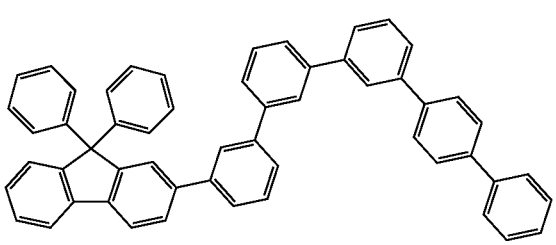
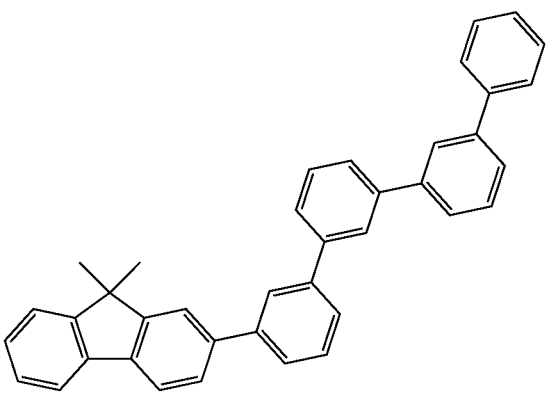

5
6
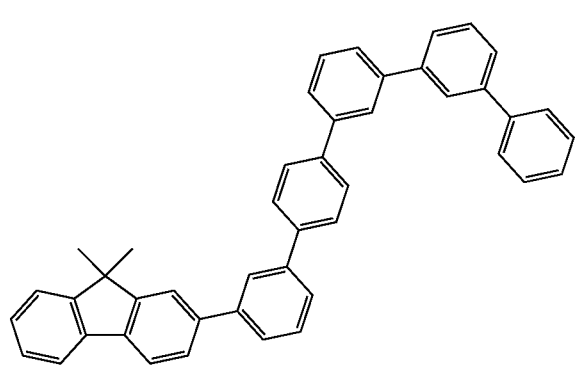
7
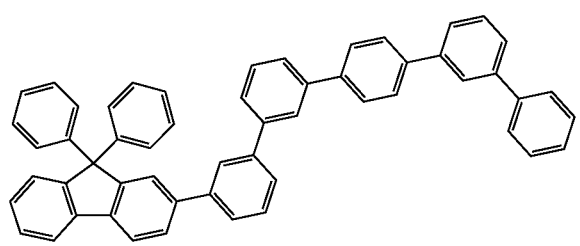
8
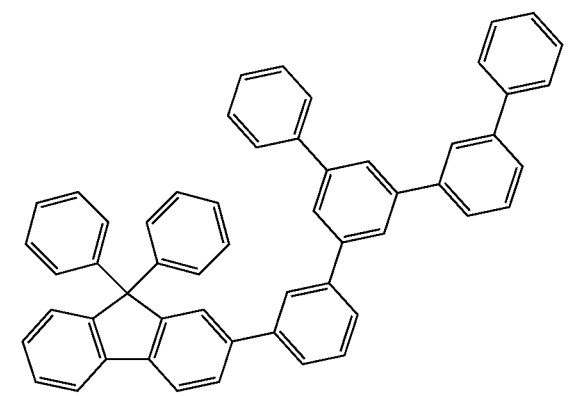
9
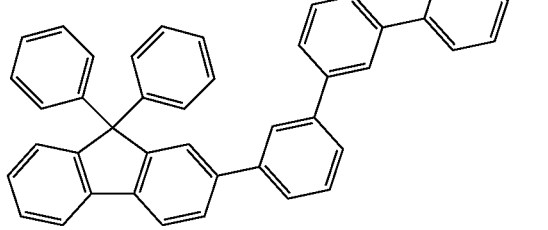
10
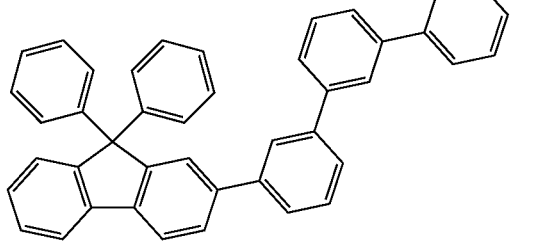
11
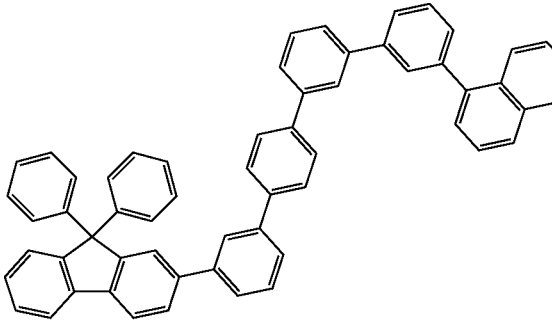
12
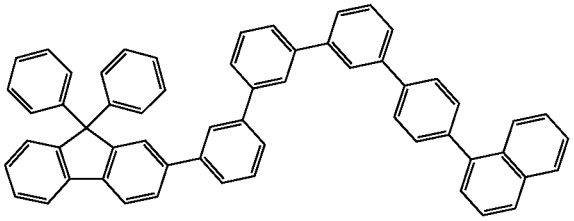
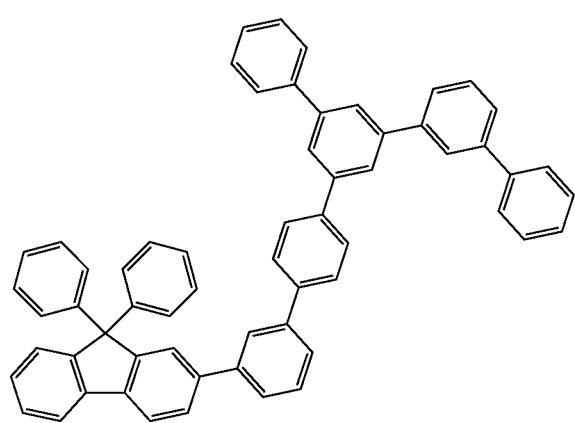

13
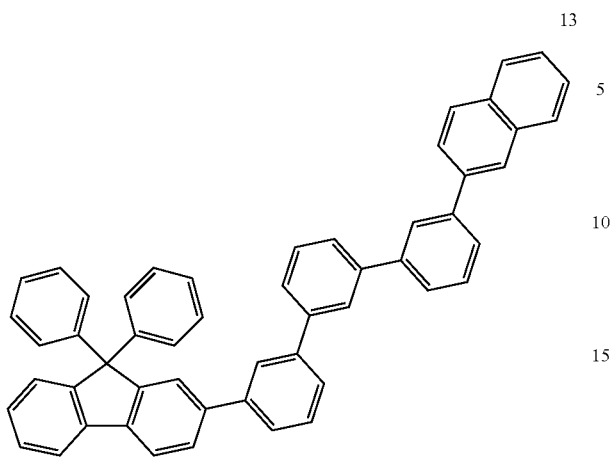
14
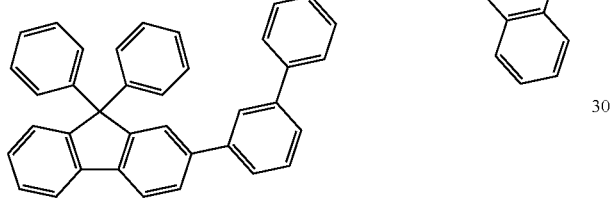
15
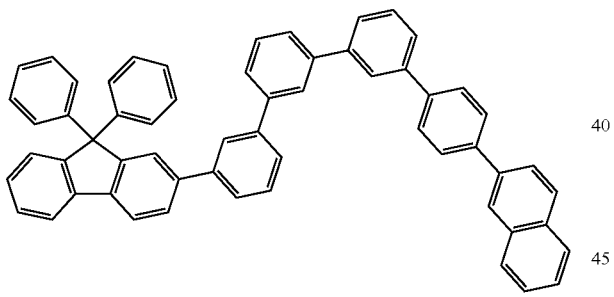
16
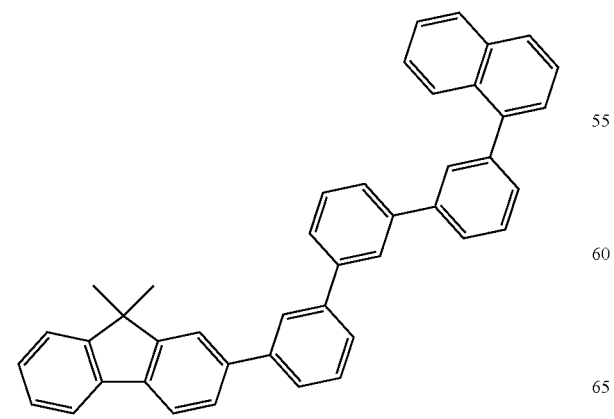
17
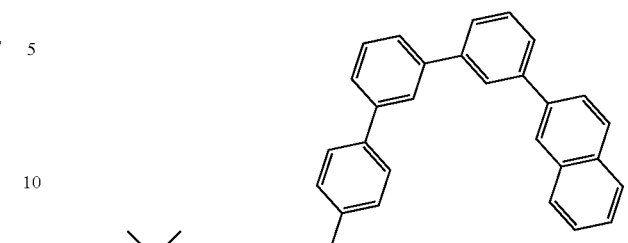
18
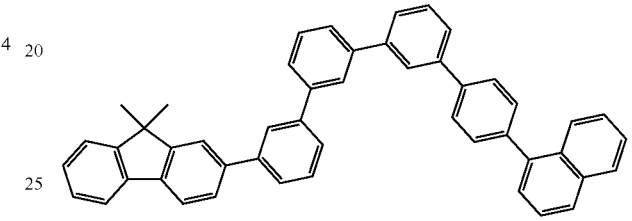
19
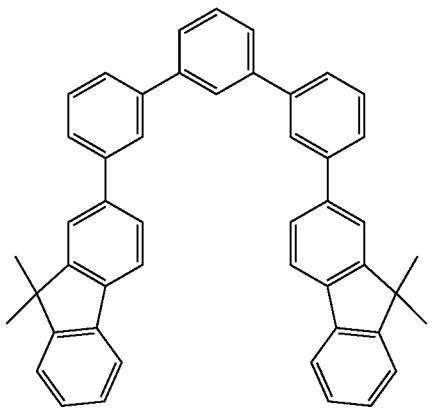
20
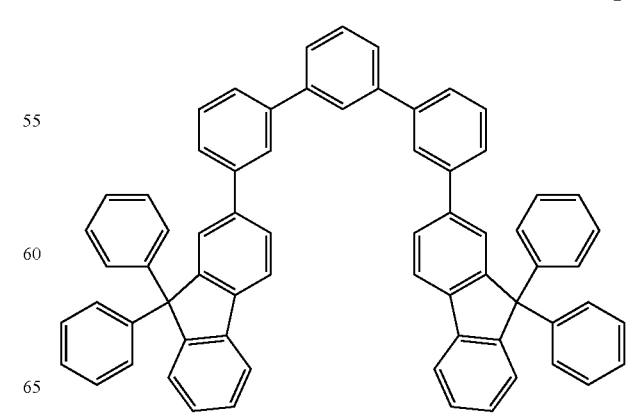

21
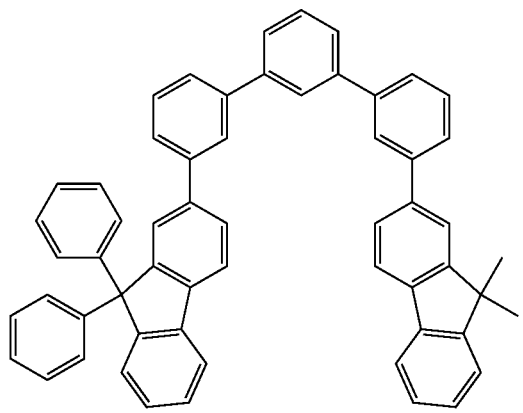
22
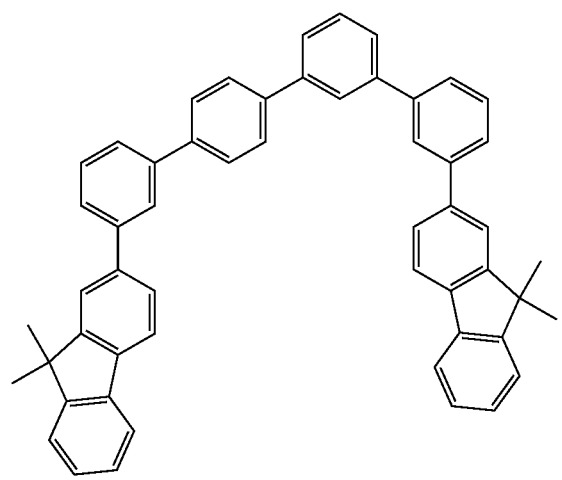
23
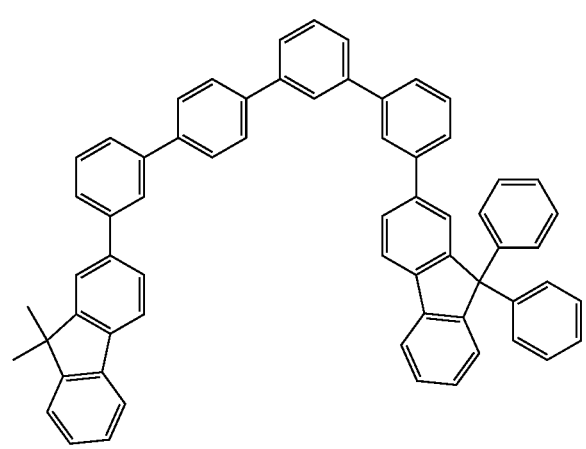
24
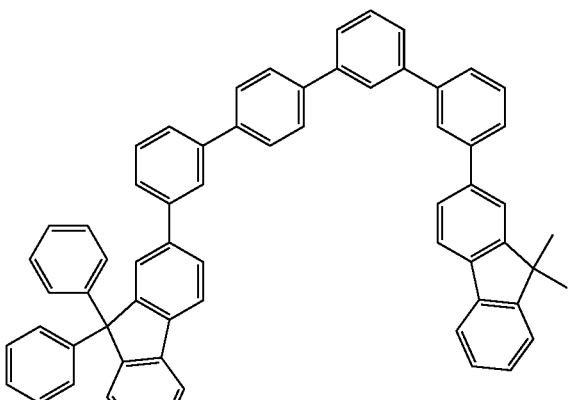
25
26

27
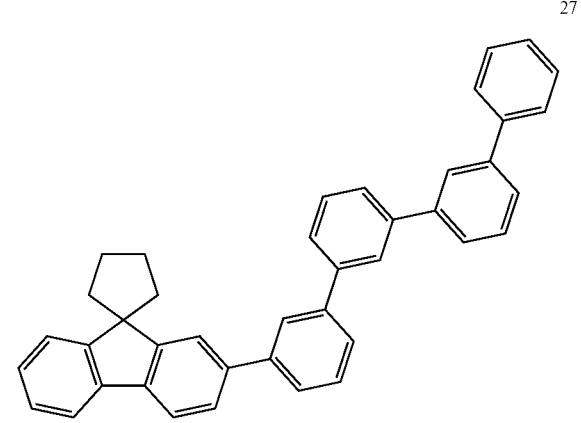
28
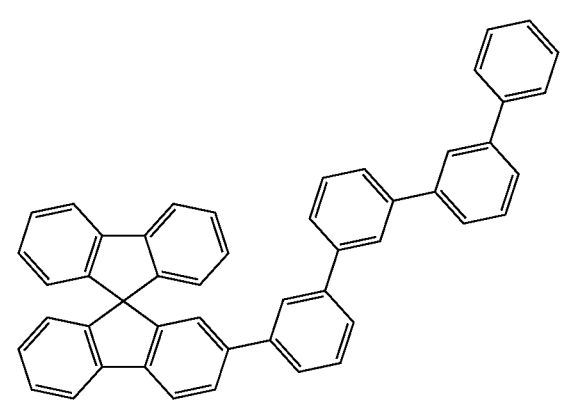
29
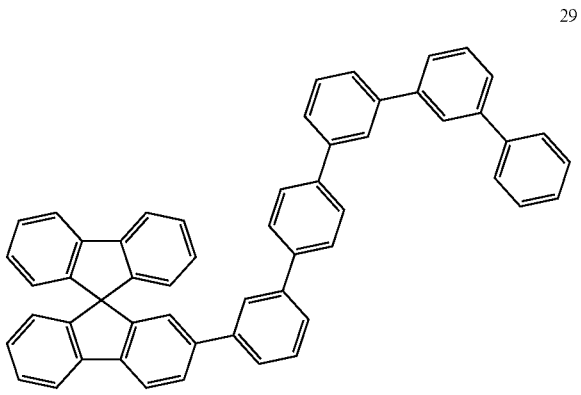
30
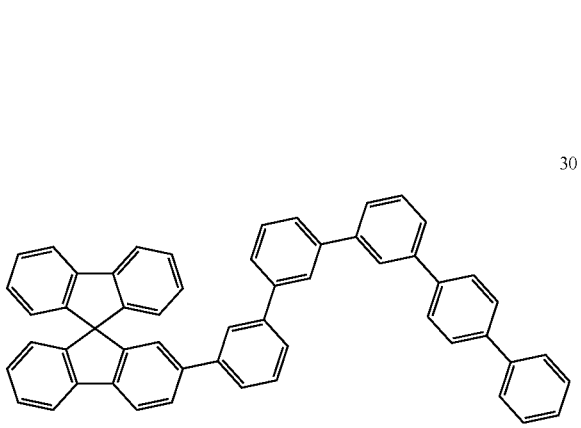
31
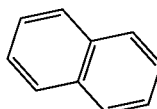
32
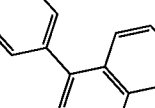
33
34
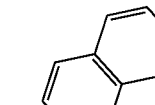

35
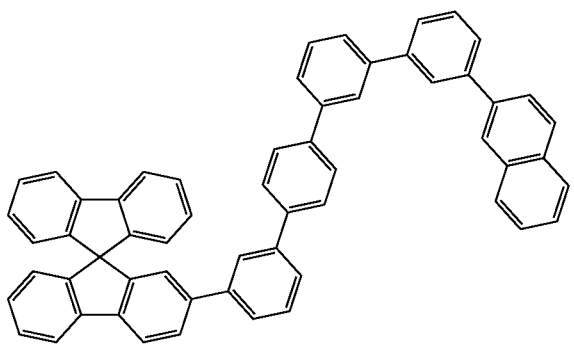
36
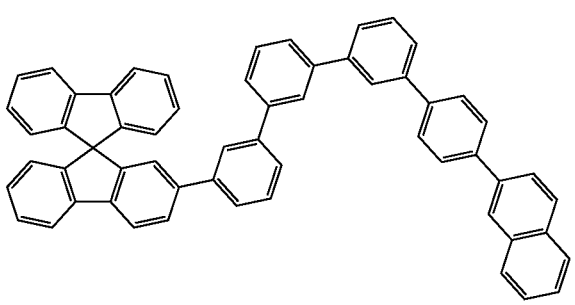
37
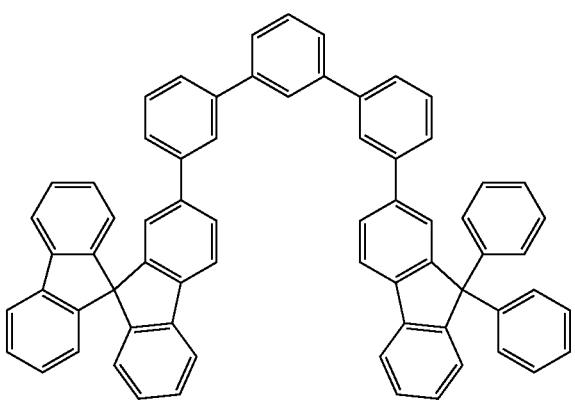
38
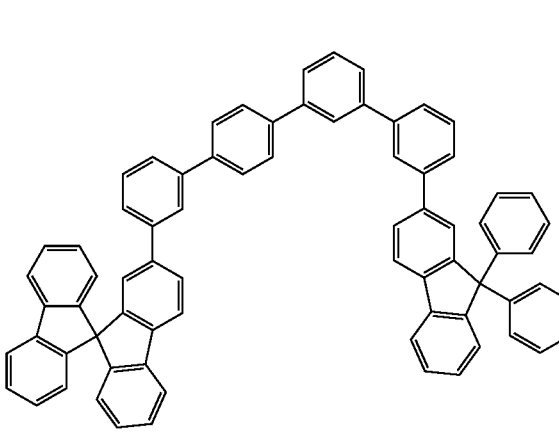
39
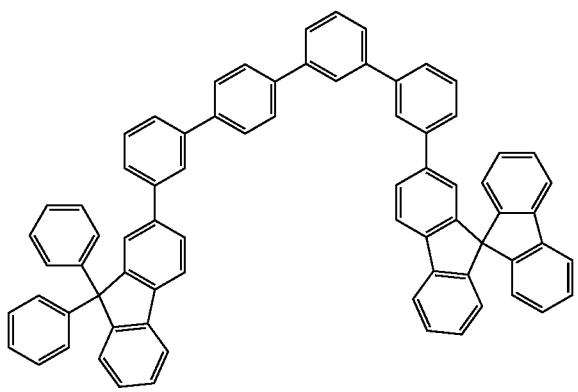
40
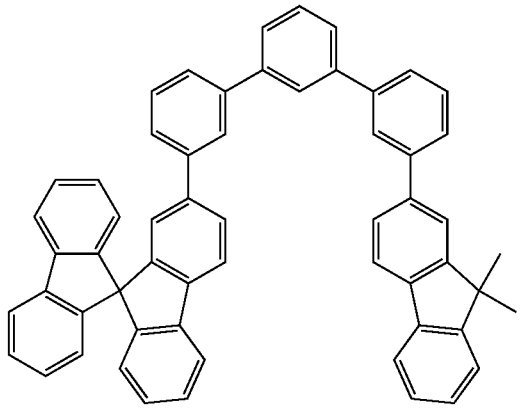
41
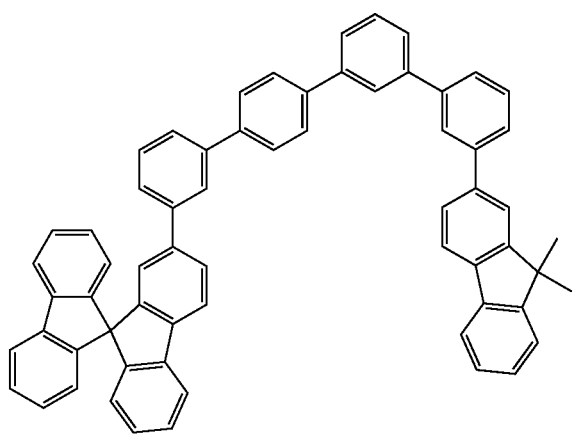

42
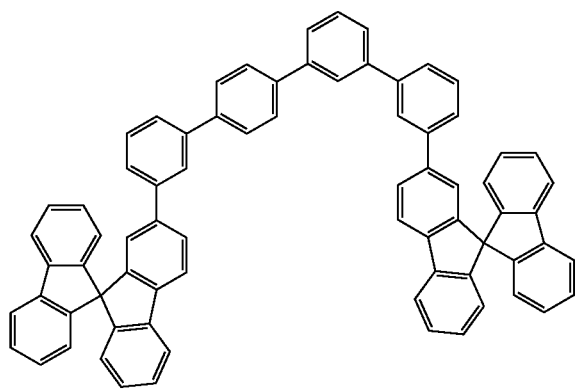
43
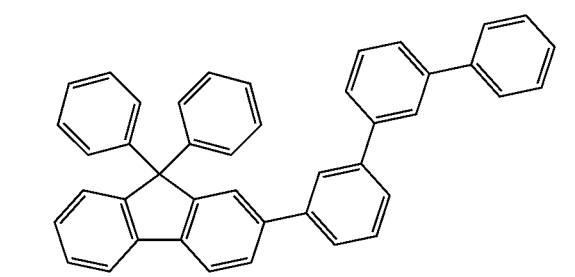
44
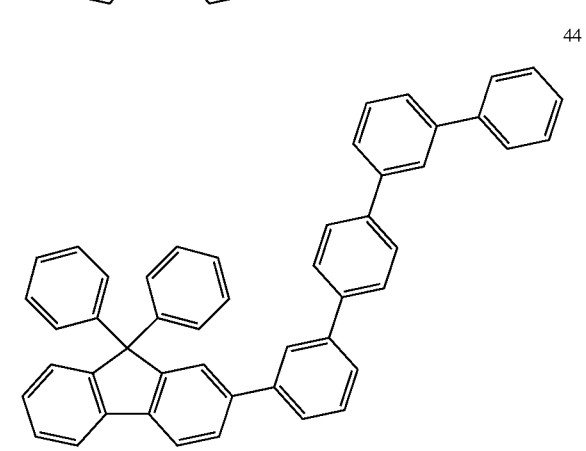
45
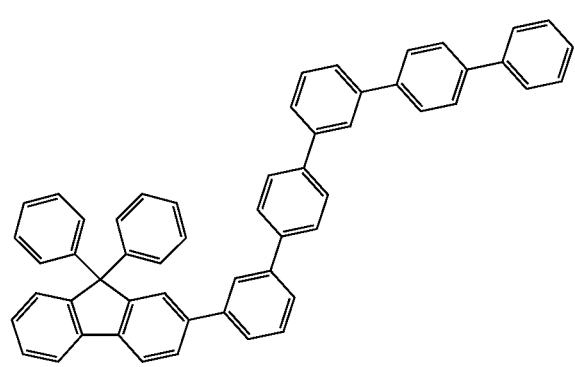
46
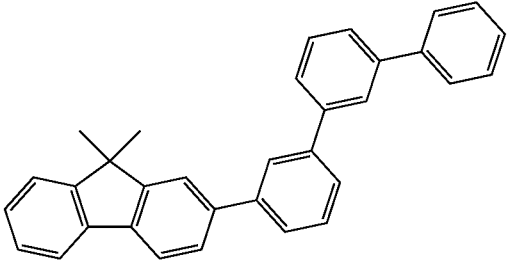
47
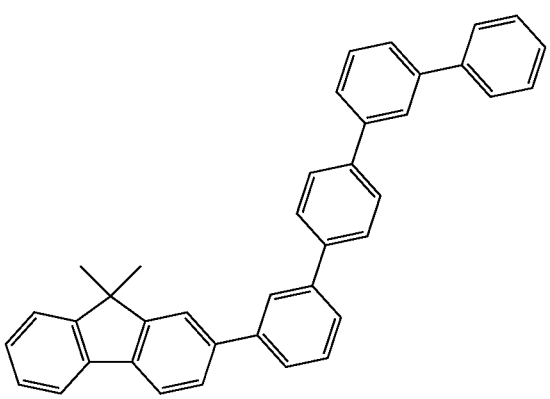
48
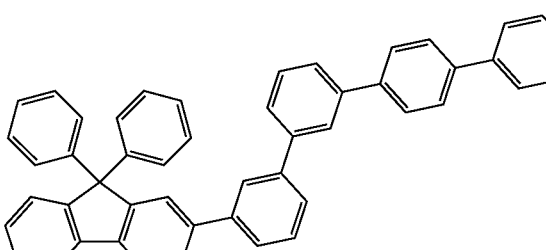
49
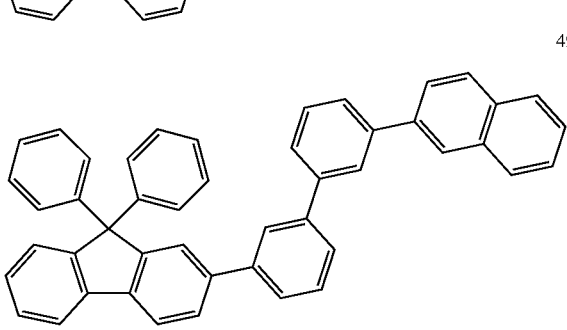
50
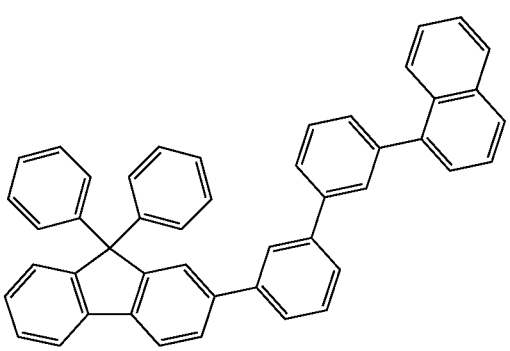

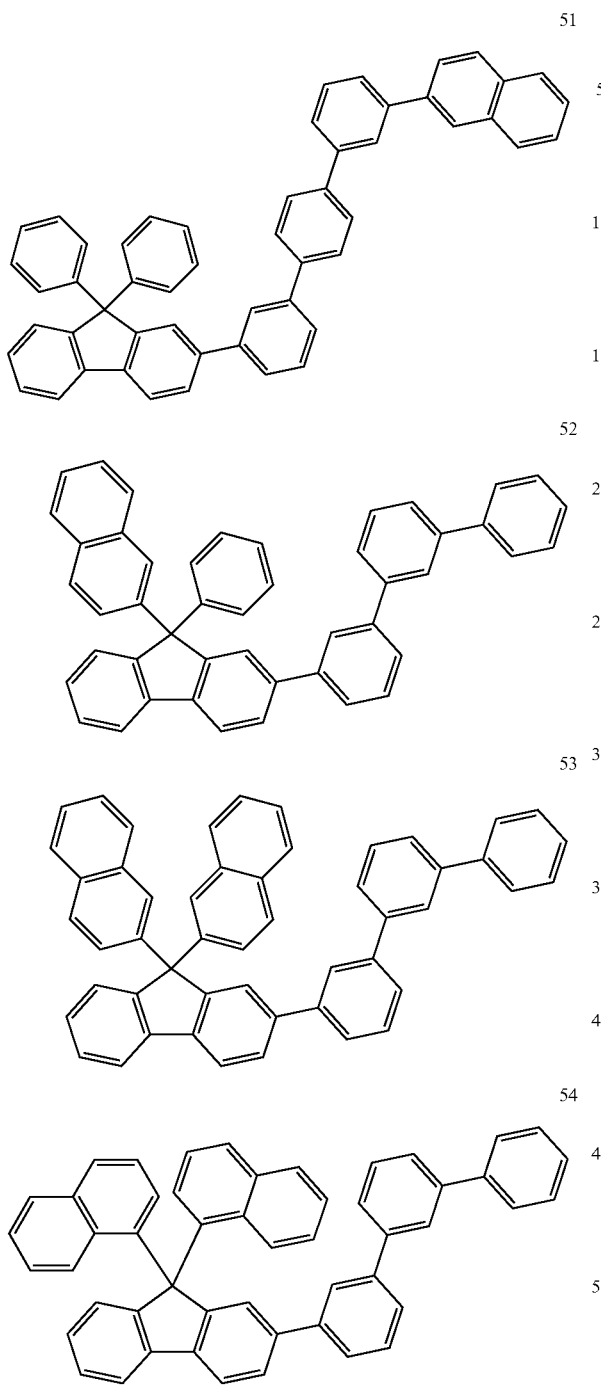
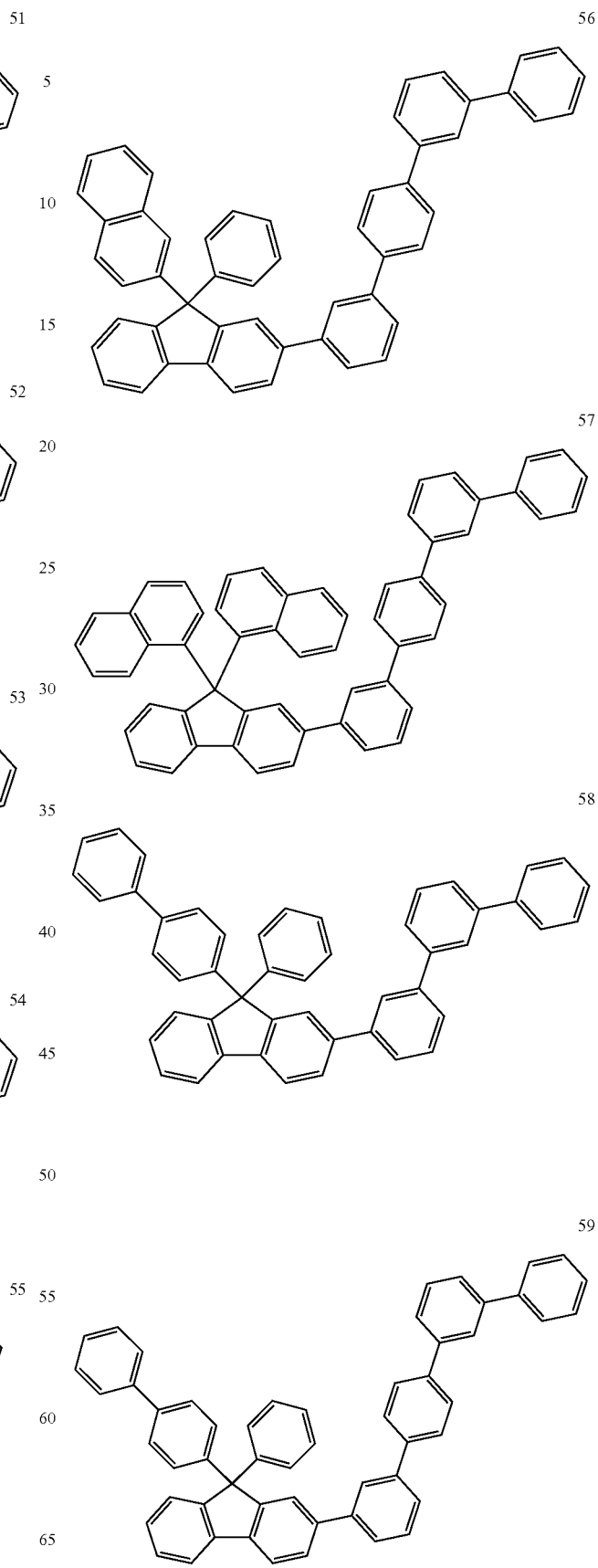

-continued

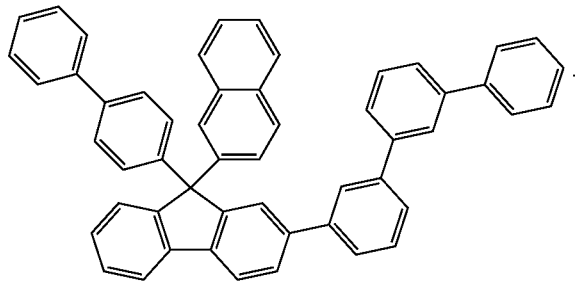

13. A composition comprising at least one condensed cyclic compound represented by Formula 1 of claim 1.

14. The composition of claim 13, further comprising a first compound comprising at least one of a carbazole-based moiety, an m-phenyl moiety, or a combination thereof.

15. The composition of claim 13, further comprising a second compound comprising an azine-based moiety.

16. The composition of claim 13, further comprising a luminescent material.

17. The composition of claim 13, further comprising a solvent.

18. An organic light-emitting device comprising:
a first electrode;
a second electrode; and
an organic layer located between the first electrode and the second electrode and comprising an emission layer, wherein the organic layer comprises at least one condensed cyclic compound represented by Formula 1 of claim 1.

19. The organic light-emitting device of claim 18, wherein the organic layer further comprises a luminescent material, and
the luminescent material emits light from a triplet exciton.

* * * * *